(12) United States Patent
Bteich et al.

(10) Patent No.: US 12,376,754 B2
(45) Date of Patent: Aug. 5, 2025

(54) BIOMARKER MONITORING SENSOR AND METHODS OF USE

(71) Applicant: American University of Beirut, Beirut (LB)

(72) Inventors: Moussa Bteich, Faraya (LB); Joseph Costantine, Albuquerque, NM (US); Rouwaida Kanj, Portland, OR (US); Assaad Eid, Paris (FR); Youssef Tawk, Albuquerque, NM (US); Ali H. Ramadan, Beirut (LB)

(73) Assignee: American University of Beirut, Beirut (LB)

( * ) Notice: Subject to any disclaimer, the term of this patent is extended or adjusted under 35 U.S.C. 154(b) by 930 days.

(21) Appl. No.: 17/409,177

(22) Filed: Aug. 23, 2021

(65) Prior Publication Data

US 2022/0039682 A1  Feb. 10, 2022

Related U.S. Application Data

(63) Continuation of application No. PCT/US2020/020388, filed on Feb. 28, 2020.

(60) Provisional application No. 62/811,760, filed on Feb. 28, 2019.

(51) Int. Cl.
*A61B 5/0507* (2021.01)
*A61B 5/00* (2006.01)
*A61B 5/145* (2006.01)

(52) U.S. Cl.
CPC ........ *A61B 5/0507* (2013.01); *A61B 5/14532* (2013.01); *A61B 5/14546* (2013.01); *A61B 5/6806* (2013.01); *A61B 5/681* (2013.01); *A61B 2562/0228* (2013.01)

(58) Field of Classification Search
CPC .............. A61B 5/0507; A61B 5/14532; A61B 5/14546; A61B 5/6802; A61B 5/6806; A61B 5/681; A61B 2562/0228; G01R 27/06; G01R 27/2623; G01R 27/32; H01P 1/2039
See application file for complete search history.

(56) References Cited

U.S. PATENT DOCUMENTS

| | | | |
|---|---|---|---|
| 6,359,444 B1 | 3/2002 | Grimes | |
| 2004/0246071 A1* | 12/2004 | Rottmoser | H01P 1/2135 333/204 |
| 2006/0273869 A1* | 12/2006 | Jachowski | H01P 1/2039 333/204 |

(Continued)

FOREIGN PATENT DOCUMENTS

GB    2428093 A    1/2007

OTHER PUBLICATIONS

S. R. Choudhury, S. K. Parui and S. Das, "Design of a novel bandstop filter using log periodic based circular split ring slots," 2012 Students Conference on Engineering and Systems, Allahabad, India, 2012, pp. 1-4, doi: 10.1109/SCES.2012.6199062. (Year: 2012 ).*

(Continued)

*Primary Examiner* — Charles A Marmor, II
*Assistant Examiner* — Andrew E Hoffpauir
(74) *Attorney, Agent, or Firm* — J. Peter Paredes; Amin Wasserman Gurnani LLP

(57) ABSTRACT

Provided herein are systems, methods and apparatuses for a Biomarker sensor.

20 Claims, 45 Drawing Sheets

(56) References Cited

U.S. PATENT DOCUMENTS

| | | | |
|---|---|---|---|
| 2008/0319285 A1* | 12/2008 | Hancock | A61B 5/14546 600/430 |
| 2010/0256465 A1 | 10/2010 | Bernstein et al. | |
| 2011/0248899 A1* | 10/2011 | Bourtoutian | H01Q 9/285 343/795 |
| 2012/0310055 A1* | 12/2012 | Jean | A61B 5/0507 600/310 |
| 2013/0181725 A1* | 7/2013 | Mazzaro | G01R 27/2623 324/636 |
| 2013/0252319 A1* | 9/2013 | Jung | G01N 33/54373 216/13 |
| 2015/0099954 A1 | 4/2015 | Achmann et al. | |
| 2016/0338625 A1 | 11/2016 | Min et al. | |
| 2017/0164878 A1* | 6/2017 | Connor | G09B 19/00 |
| 2020/0337610 A1* | 10/2020 | Yu | A61B 5/6829 |

OTHER PUBLICATIONS

Chien et al. "A microwave reconfigurable dielectric-based glucose sensor with 20 mg/dl sensitivity at sub-nL sensing volume in CMOS," 2015 IEEE MTT-S International Microwave Symposium, Phoenix, AZ, USA, 2015, pp. 1-4, doi: 10.1109/MWSYM.2015. 7167141. (Year: 2015).*

European Search Report and Written Opinion issued in corresponding foreign application, EP 20763735.6 dated Oct. 19, 2022, 11 pages.

Ansari M. A. H. et al. "Multi-Band RF Planar Sensor Using Complementary Split Ring Resonator for Testing of Dielectric Materials," IEEE Sensors Journal, vol. 18, No. 16, pp. 6596-6606, Aug. 15, 2018.

Kiani, S et al. "Band-stop filter sensor based on SIW cavity for the non-invasive measuring of blood glucose," IET Wireless Sensor Systems, vol. 9, Issue 1, pp. 1-5, 2019.

Sam, S et al. "Ultra-wideband tunable resonator based on varactor-loaded complementary split-ring resonators on a substrate-integrated waveguide for microwave sensor applications," IEEE Transactions on Ultrasonics, Ferroelectrics, and Frequency Control, vol. 60, No. 4, pp. 657-660, Apr. 2013.

Office Action issued in corresponding foreign application, CN 2020800174505 dated Sep. 20, 2023, 12 pages.

Baghbani, R. et al. "Microwave sensor for non-invasive glucose measurements design and implementation of a novel linear" IET Wireless Sensor Systems, 2015, vol. 5, No. 2, p. 51-57.

Bahar, A. et al. "Analysis of Enhanced Coupling Peripheral Type Ring Resonator Sensor for Liquid," ARPN Journal of Engineering and Applied Sciences, vol. 11, No. 6, Mar. 2016, pp. 3856-3860.

Boybay, M. S. et al. "Material Characterization Using Complementary Split-Ring Resonators," IEEE Trans. Instrum. Meas.,vol. 61, No. 11, Nov. 2012, pp. 3039-3046.

Boybay, M. S. et al. "Non-Destructive Thickness Measurement Using Quasi-Static Resonators," IEEE Microw. Wireless Compon. Lett., vol. 23, No. 4, Apr. 2013, pp. 217-219.

Choudhury, S. R. et al. "Design of a Novel Bandstop Filter Using Log Periodic Based Circular Split Ring Slots," 2012 Students Conference on Engineering and Systems, Allahabad, Uttar Pradesh, 2012, pp. 1-4.

Hsu, C. et al. "Improved Approach Using Multiple Planar Complementary Split-Ring Resonators for Accurate Measurement of Permittivity" 2016 IEEE MTT-S International Wireless Symposium (IWS), Shanghai, 2016, pp. 1-4.

Liu, Y. et al. "Novel Nested Split-Ring- Resonator (SRR) for Compact Filter Application," Progress in Electromagnetics Research (PIER), vol. 136, 2013, pp. 765-773.

Rusni, I.M. et al. "An Aligned-Gap and Centered-Gap Rectangular Multiple Split Ring Resonator for Dielectric Sensing Applications," Sensors 2014, 14, pp. 13134-13148.

International Search Report and Written Opinion issued in corresponding foreign application, PCT/US2020/20388 dated Jul. 16, 2020, 5 pages.

* cited by examiner

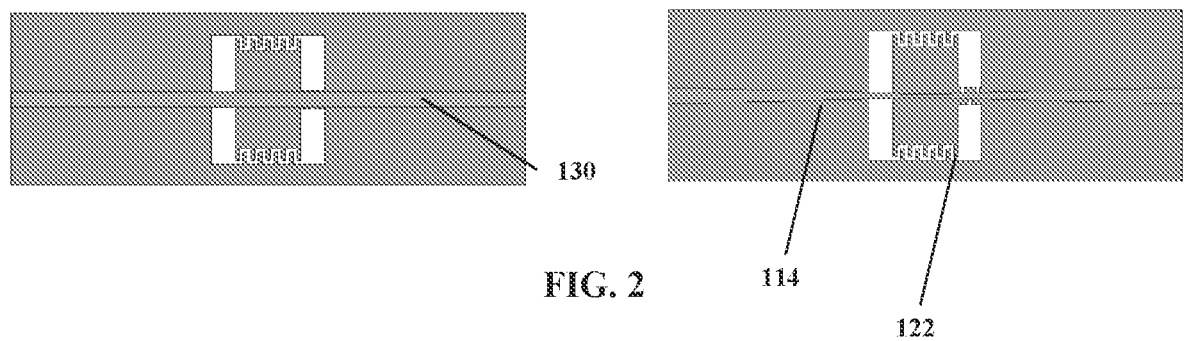
FIG. 2
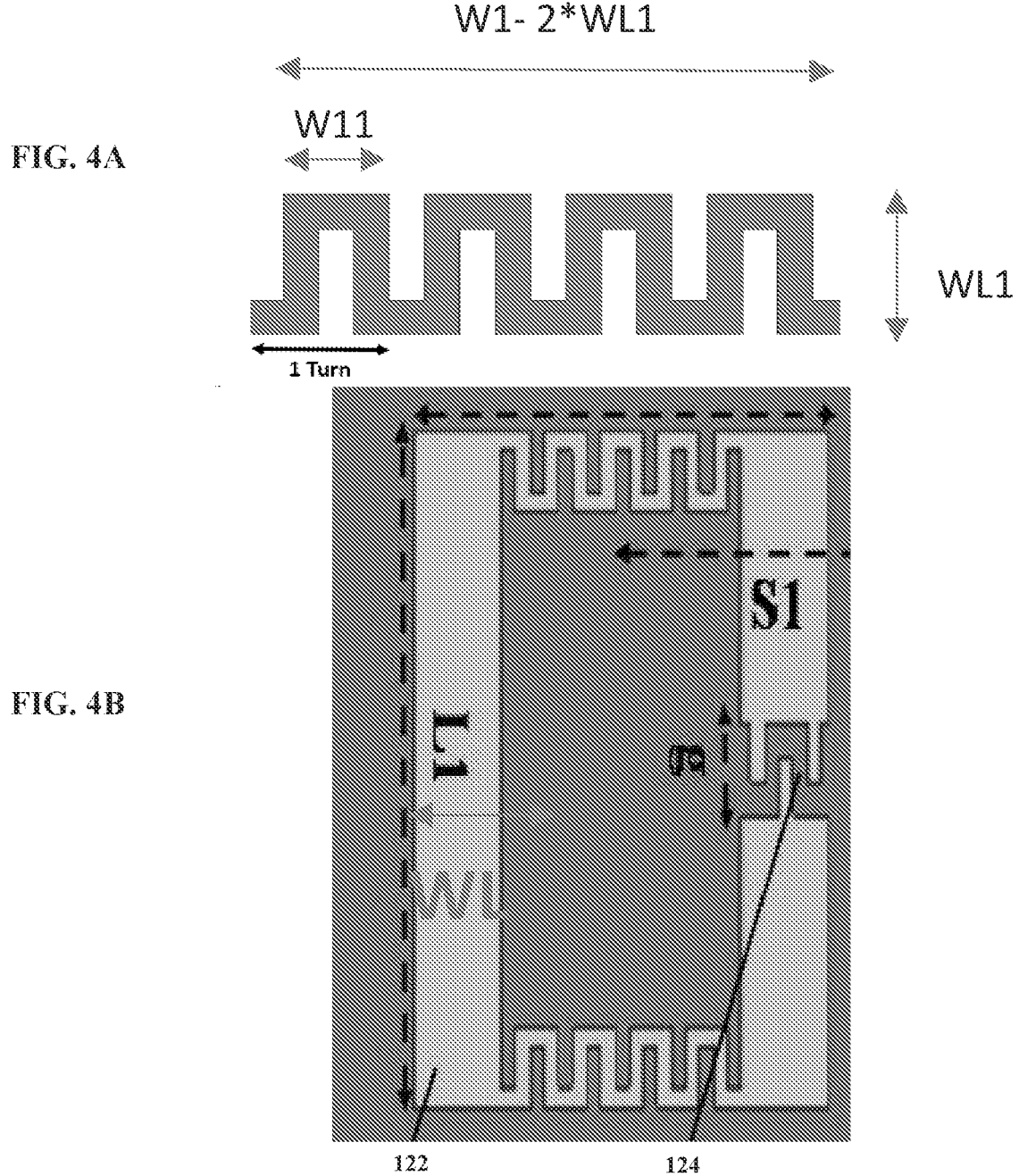
FIG. 4A
FIG. 4B

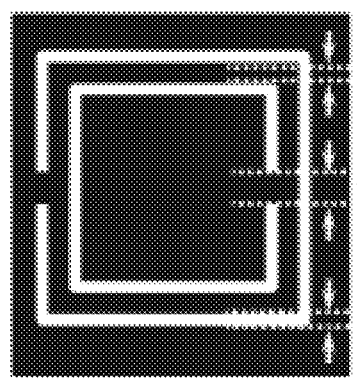
FIG. 5A
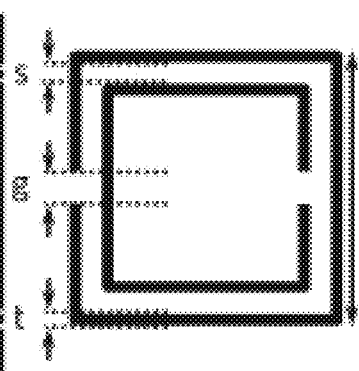
FIG. 5B
FIG. 5D
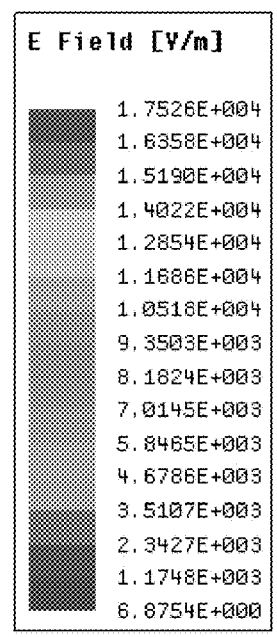
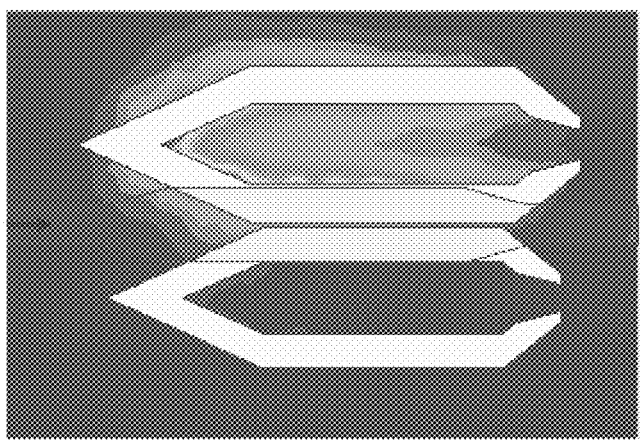
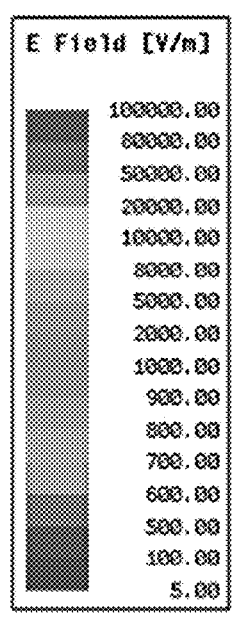
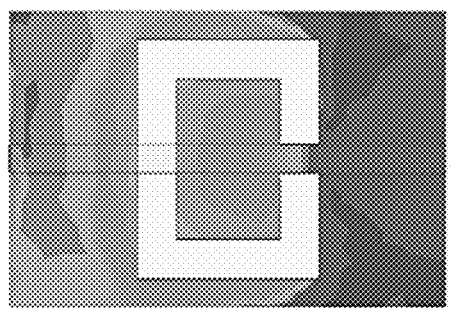
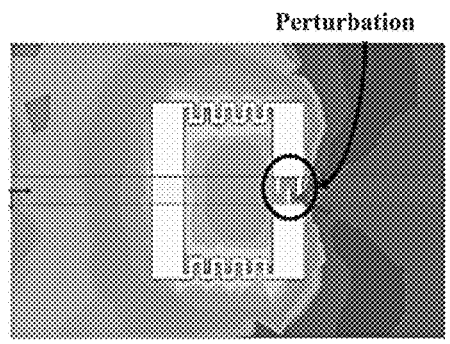
FIG. 6A
FIG. 6B ■ Zone A ■ Zone B ■ Zone C ■ Zone D ■ Zone E

Clarke Error Grid Output (LOO)

■ Zone A ■ Zone B ■ Zone C ■ Zone D ■ Zone E

BIOMARKER MONITORING SENSOR AND METHODS OF USE

CROSS REFERENCE TO RELATED APPLICATIONS

The present application is a continuation application from PCT application serial no. PCT/US2020/020388, filed Feb. 28, 2020, which claims priority from U.S. provisional Ser. No. 62/811,760, filed Feb. 28, 2019, all herein incorporate by reference in their entirety.

Accurate characterization of the dielectric constant of materials is critical and are used to extract dielectric constant of materials, although many methods may be accurate, they are bulky and can impact MUTs. An alternative method to extract the electrical properties of a material is approached by placing MUTs in close proximity to resonators. Such placement perturbs the resonator's S-parameters, in comparison to its free-space operation, and thus helps extract the electrical properties of the loading MUT [1].

Several resonator-based sensors are discussed in the literature for the aim of characterizing materials' dielectric constant variations. However, the focus has always been on designing narrow-band sensors with a high quality factor, in order to increase the sensitivity of the sensor to dielectric constant variations. The use of complementary split ring resonators (CSRRs) with narrow responses has been examined in [2] and [3]. The proposed resonators are able to sense and predict the dielectric constant values of low loss substrates with a percentage error not exceeding 10% [2]. Also, by increasing the number of resonators from two to three, the sensor is able to predict both the dielectric constant and thickness of the substrates with lower error [3].

Log periodic based filter is discussed in S. R. Choudhury, S. K. Parui and S. Das, "Design of a novel bandstop filter using log periodic based circular split ring slots," 2012 *Students Conference on Engineering and Systems*, Allahabad, Uttar Pradesh, 2012, pp. 1-4.

Logarithmically arranged circular split ring slots were used to build a filter. The filter has a center frequency of 5.1 GHz and a bandwidth of 1.02 GHz. The scale factor is 0.98 (almost uniform distribution). The fractional bandwidth is 20% in this paper.

Filter used as glucometer is discussed in Baghbani, R., Rad. M. A., Pourziad, A. Microwave sensor for non-invasive glucose measurements design and implementation of a novel linear. HET Wireless Sensor Systems, 2015, vol. 5, no. 2, p. 51-57. A planar band pass filter operating at 1.9 GHz was designed to perform as a glucometer. Some tests showed some correlation between the response of the filter and the levels of blood glucose. The authors of this paper did not proceed further in this work in terms of predicting actual glucose levels. They only showed variability in S-parameters in time based on one patient oral glucose test.

Previous works focused on designing narrow band sensors to detect changes in permittivity. The present invention attempts to solve these problems as well as others.

SUMMARY OF THE INVENTION

Provided herein are systems, methods and apparatuses for a Biomarker Sensor for Biomarker Monitoring.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2 is a comparison between regular feeding line and tapered line feeding. Advantage of applying a tapered transmission line. Without loss of generality, example demonstrates case of one element.

FIGS. 4A-4B are schematic diagrams showing meandering lengths.

FIG. 5A is a schematic diagram showing the complementary resonator; FIG. 5B is a schematic diagram showing the regular resonator; FIGS. 5D-5E are graphs showing the E fields magnitude and distribution for one resonance frequency for the biomarker sensor 100$b$.

FIG. 6A is a graph of the electric field intensity distributed over the bottom layer of a regular open loop resonator; FIG. 6B is a graph showing the Electric field intensity distributed over the bottom layer of a modified complementary open loop resonator.

In addition, the dielectric constant of the MUT is swept from 60 to 75 to reflect some realistic dielectric values that relate to human organs or blood.

DETAILED DESCRIPTION OF THE INVENTION

Figure 1A:
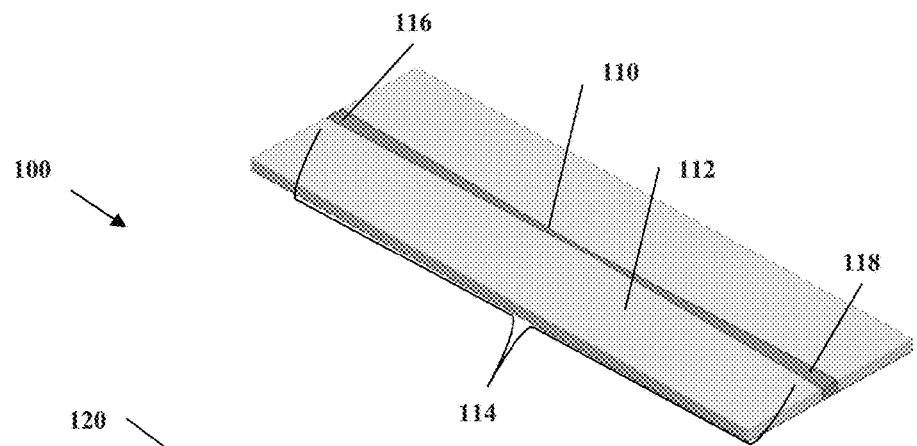
FIG. 1A is an exploded perspective view of the top and bottom layers of the biomarker sensor, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the monitored area of a patient's body or material under test.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising." "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein "filter" and "sensor" are synonymous and interchangeable in meaning, i.e. filtering signals and sensing signals or an electrical property for biomarker detection.

The Biomarker sensor measures biological and chemical markers, concentration information, and tracers in blood including glucose concentration without any extraction of blood. A device for continuously measuring biological, chemical markers and tracers in the blood stream for physiological and pathophysiological screening in health and in disease in a non-invasive manner. Biological markers can include novel/foreign/malignant or non-malignant cells or other newly developed molecules that may not be part of the typical constituents of the biological system.

Markers and concentration information can also be traced not only in blood, but in the rest of the biological system, such as saliva, tissue, bodily fluids, and the like. Bodily fluids may include, but are not limited to: Amniotic fluid, Aqueous humour and vitreous humour, Bile, Blood, Blood plasma, Blood serum, Cerebrospinal fluid, Cerumen (earwax), Chyle, Chyme, Endolymph and perilymph, Exudates, Feces, ejaculate, Gastric acid, Gastric juice, Lymph, Mucus (including nasal drainage and phlegm), Pericardial fluid, Peritoneal fluid, Pleural fluid, Pus, Rectal discharge, Rheum, Saliva, Sebum (skin oil), Serous fluid, Semen, Serum, Smegma, Sputum, Synovial fluid, Sweat, Tears, Urine, Vaginal secretion/discharge, Vomit, Intra- and extracellular fluid contents, Intracellular fluid, Extracellular fluid, Intravascular fluid (blood plasma), Interstitial fluid, Lymphatic fluid (sometimes included in interstitial fluid), or Transcellular fluid.

2. An example of pathophysiological alteration leading to diseases include hyperglycemia/diabetes, cholesterolemia, heart disease markers as well as other biological alterations that involve measuring variations of glucose level, cholesterol levels, Pro-BNP and troponin levels, etc. in living tissue.

The Biomarker sensor comprises a non-invasive method and is a wearable device that can be a glove, semi-glove, or sock, or any similar wearable device that can non-invasively measure these blood physiological Biomarker, such as glucose levels in an instantaneous manner and continuous manner.

A Biomarker sensor for continuously measuring biological, chemical markers and other tracers in the blood stream for physiological and pathophysiological screening in health and in disease in a non-invasive manner. Biomarkers can include novel/foreign/malignant or non-malignant cells or other newly developed molecules that may not be part of the typical constituents of the biological system. Biomarkers can also be traced not only in blood, but in the rest of the biological system, such as saliva, tissue, and the like.

Biomarkers as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed.

Biomarkers can include naturally occurring substances, artificial substances, metabolites, and/or reaction products. In some embodiments, the Biomarkers for measurement by the sensor heads, devices, and methods is a Biomarker. However, other Biomarkers are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; dipthelia/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactoselgal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), BIA-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cnizi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute Biomarkers in certain embodiments. The Biomarkers can be naturally present in the biological fluid, for example, a metabolic product, a hormone, an antigen, an antibody, and the like. Alternatively, the Biomarkers can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated Biomarkers. Biomarkers such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

An example of pathophysiological alteration leading to diseases include, but are not limited to, hyperglycemia/diabetes, cholesterolemia, heart disease Biomarkers as well as other biological alterations that involve measuring variations of glucose level, cholesterol levels, Pro-BNP (pro-Brain Natriuretic peptide) and troponin levels, and other molecular Biomarkers in living tissue. For example in diabetes, the proposed prototype is envisioned to help monitor instantaneous glucose levels to be used: to determine the alteration in glycemia and variations from norm; and for autonomous interventions such as insulin injections; and to offer diabetic patients an improved and self-constrained control of the disease. Thus, along with an estimate of the bulk concentration, the device monitors the rate of change of concentrations to predict possible hyperglycemia and hypoglycemia early.

The Biomarker sensor 100 comprises a sensor 100 including a top layer 110 operably coupled with a bottom layer 120, as shown in FIG. 1A, which measures blood constituents such as glucose concentration in blood without direct contact. The biomarker sensor can be integrated in wearable devices such as a watch, a bracelet, a necklace, an anklet, a glove, a sleeve, or a sock that can non-invasively measure blood glucose levels in an instantaneous and continuous manner. This Biomarker sensor has several features that allow enhanced sensitivity of the sensor to glucose measurements, according to one embodiment. However, other biomarkers may be detected as indicated above.

In one embodiment, the biomarker sensor comprises a Log-periodic based filter. The biomarker sensor includes a Broadband or a wideband operation and that can be made reconfigurable to allow for adjustable response in terms of the Broadband response, Capability to shift between broadband and multi-narrowband responses, and Capability to adjust its resonance frequencies. The biomarker sensor includes sensitivity to permittivity variations characterized by High concentration of fields within small areas and an open loop resonator allows large surface of interaction between fields and Material Under test. The biomarker sensor includes a compact size, a microwave circuitry, and a magnitude converter, where miniaturization techniques were employed to enable compact feature sizes and detect the microwave spectrum including phase and magnitude parameters.

In one embodiment, the biomarker sensor is a broadband reject filter for dielectric constant characterization. In one embodiment, at least four complementary Open Loop Resonators (OLRs), which follow a modified log-periodic distribution, are etched beneath a tapered feed line to achieve a broadband rejection response for the proposed filter. The configuration of the embedded log-periodic resonators is designed to attain high sensitivity to lossy material over the about 1.25-2.25 GHz frequency span. The biomarker sensor is tested to validate its sensitivity and performance in differentiating among various dielectric constant levels for a material under test (MUT), where an average sensitivity of about 0.42 dB/$\varepsilon_r$ and about 3.65°/$\varepsilon_r$ is achieved at f=2.25 GHz.

The biomarker sensor comprises a broadband reject filter design that employs log-periodic distributed complementary (OLRs). The biomarker sensor is implemented as a sensitive, non-destructive and compact sensor for dielectric constant characterization over a broadband frequency range. The biomarker sensor estimates the dielectric constant using a plurality of features, which leads to a low prediction error.

Figure 1C:
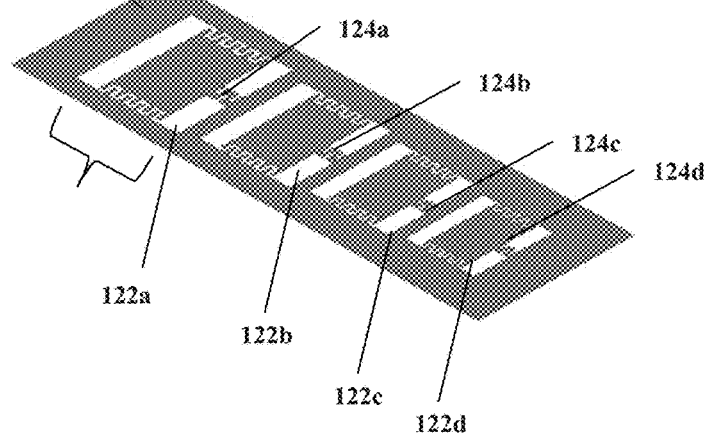
FIG. 1C is a simulated embodiment of the biomarker sensor.
Figure 1C:
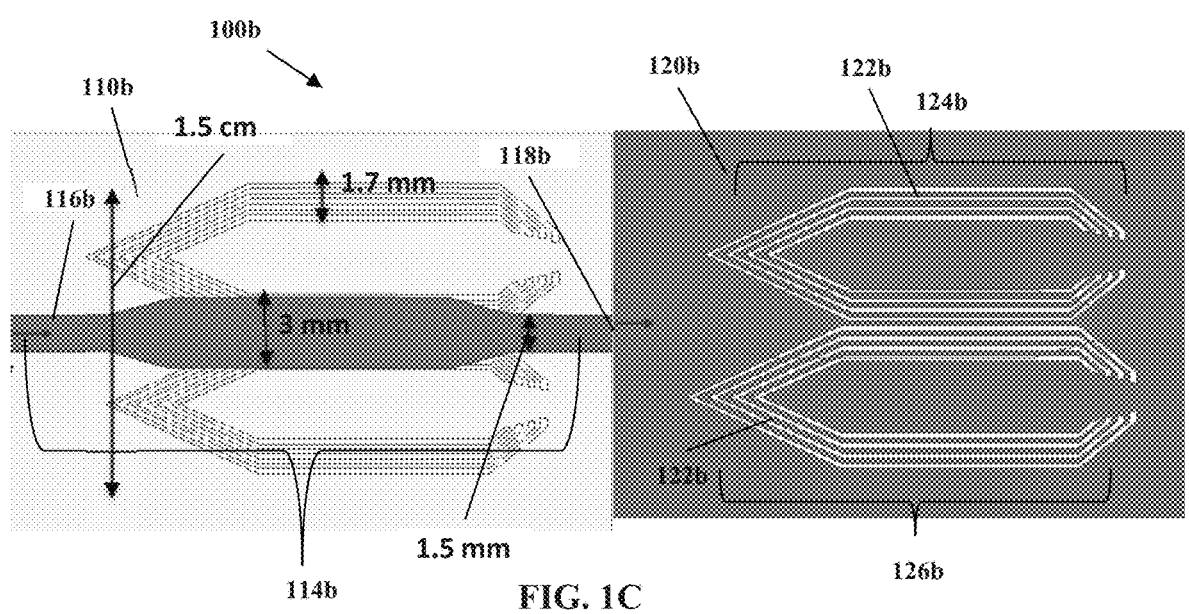
Figure 1B:
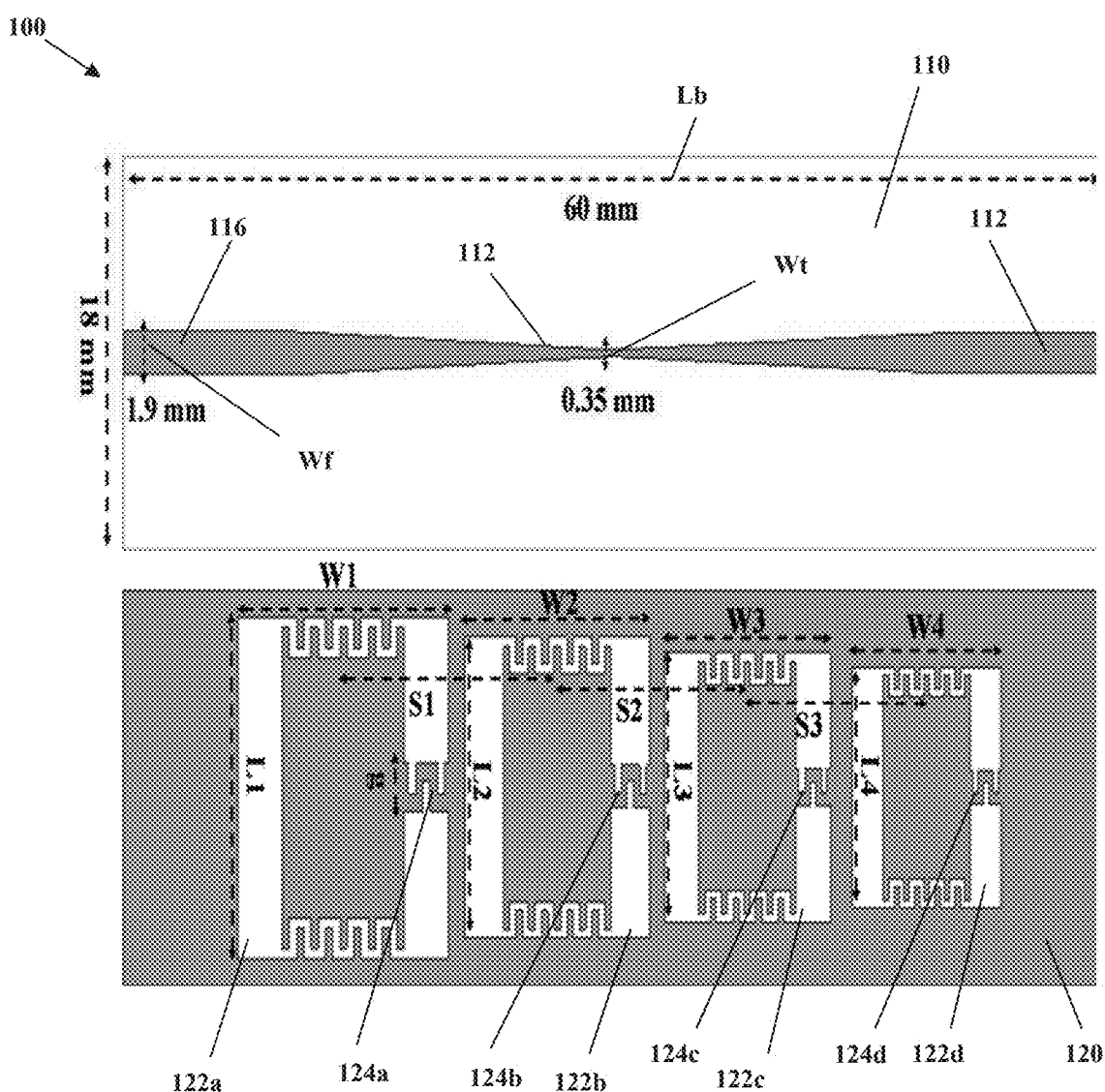
FIG. 1B is a top view of the top layer and bottom layers, according to one embodiment.
Figure 1D:
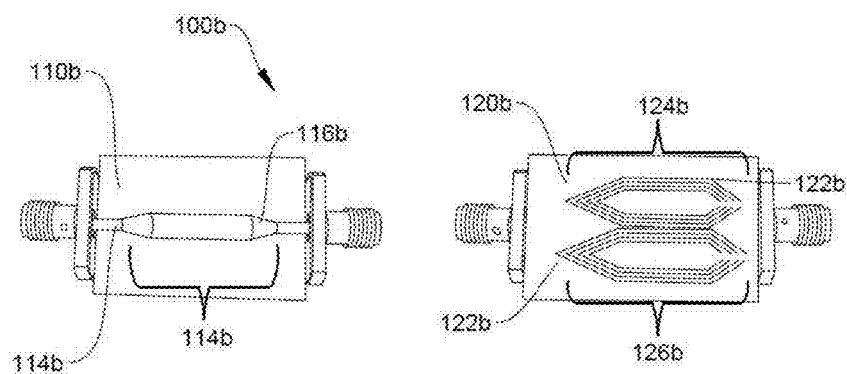
FIG. 1D is the fabricated prototype of the biomarker sensor, according to one embodiment.

In another embodiment, the biomarker sensor 100b is shown in FIGS. 1C-1D. The biomarker sensor comprises a top layer 110b and a bottom layer 120b, wherein the top layer 110b includes a feeding line 114b with a first port 116b and a second port 118b and the bottom layer 120b includes an octa-band electromagnetic two port network and eight open loop resonators 122b (OLRs). Four resonators 122b form first set 124e and another four resonators 122b form a second set 126b, wherein the first set 124e and the second set 126b include a generally hexagonal configuration following the distribution of arteries and veins in a human arm. The first set 124e includes first opening 128b in the hexagonal configuration and the second set 126b includes a second opening 128c in the hexagonal configuration. Each adjacent hexagonal resonator 112b is separated by a distance D. In one embodiment, the distance D is about 0.2 mm but can be adjusted according to the reconfigurable requirements. The width of the hexagonal configuration of the first set 124e and the second set 126b is about 1.7 mm. The biomarker sensor 100b detects non-invasively and continuously the concentration of blood constituents in a human blood stream.

In one embodiment, the lengths of the resonators 122b are equivalent to $\lambda/2$ at the resonance frequency. The width of each set of resonators 122b is relative to the width of the ulnar arteries, as shown in Table 2a. In one embodiment, the width of the resonators 122b approximates the right ulnar artery between 1.3 mm and 3.7 mm and approximates the left ulnar artery between about 1.5 mm and about 3.1 mm. The width of each resonator is about 0.2 mm. In one embodiment, the width of each resonator is dictated by the accuracy of the milling machine.

TABLE 2a

Table-2: Descriptive Statistics of 251 Patients.

| Variable | Minimum | Maximum | Mean ± S.D |
|---|---|---|---|
| Age (Years) | 32 | 75 | 51.9 ± 9.8 |
| Height (cms) | 140 | 182 | 160.7 ± 7.98 |
| Weight (kg) | 40 | 107 | 66.6 ± 10.4 |
| BSA | 1.22 | 2.8 | 1.7 ± 0.18 |
| EMI | 14.2 | 39.3 | 25.8 ± 3.8 |
| Right Radial artery diameter (mm) | 1.4 | 3.6 | 2.3 ± 0.4 |

TABLE 2a-continued

Table-2: Descriptive Statistics of 251 Patients.

| Variable | Minimum | Maximum | Mean ± S.D |
|---|---|---|---|
| Left Radial Artery Diameter (mm) | 1.2 | 3.1 | 2.2 + 0.4 |
| Right Ulnar Artery (mm) | 1.3 | 3.7 | 2.4 ± 0.4 |
| Left Ulnar Artery (mm) | 1.5 | 3.1 | 2.3 ± 0.3 |

Figure 3B:
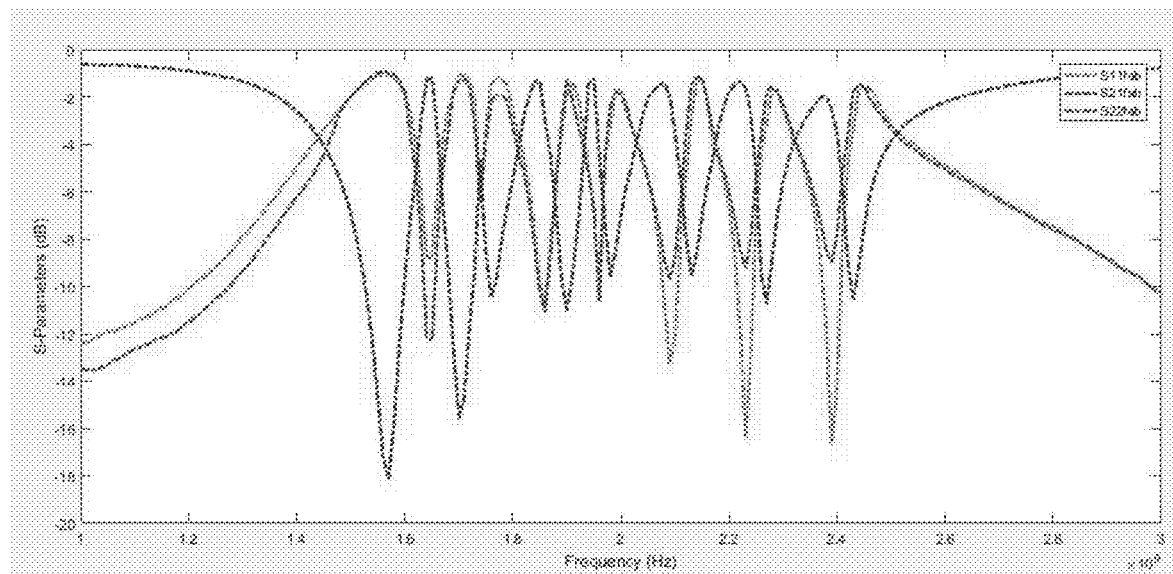
FIG. 3B is a graph showing the measured S-Parameters of the biomarker sensor 100$b$.

The biomarker sensor 110b is a multi-band sensor that allows some frequencies of the signal to pass from the first port 114b through the second port 116b, while the biomarker sensor 110b stops the passage of other frequencies. The biomarker sensor 110b does not radiate energy to the human body, but rather sees the multi-layers of the human tissues as a load that affects the response of the biomarker sensor 110b. The biomarker sensor 110b includes eight stop bands ranging between about 1.5 GHz and about 2.5 GHz. These stop bands are separated by seven pass bands as shown in FIG. 3B.

In one embodiment, the biomarker sensor 110b is a planar double-layered micro-strip two port network. The top layer 110b consists of the feeding network, and the bottom layer 120b is the sensing area. The top layer 110b and the bottom layer 120b are conductive paths or conductive layers are separated by a dielectric material. In one embodiment, biomarker sensor 110b comprises a variety of substrates with different dielectric materials and/or different thicknesses. The biomarker sensor 100b includes a variety of substrates, different materials including, but not limited to silicon, PET, Polyimide; different permittivity; and different thickness including about 0.05 mm, about 0.13 mm, and about 1.28 mm, detailed further in Table 3a.

TABLE 3a

| Substrate | Thickness (μm) | Permittivity | Tan (δ) |
|---|---|---|---|
| Ceramic-filled PTFE composites (Rogers 3006) | 1.28 | 6.15 | 2e-3 |
| Ceramic-filled PTFE composites (Rogers 3003) | 0.25 | 3 | 1e-3 |
| PET | 0.136 | 2.99 | 5.7e-3 |
| Polyimide | 0.05 | 3.5 | 8e-3 |

Figure 4C:
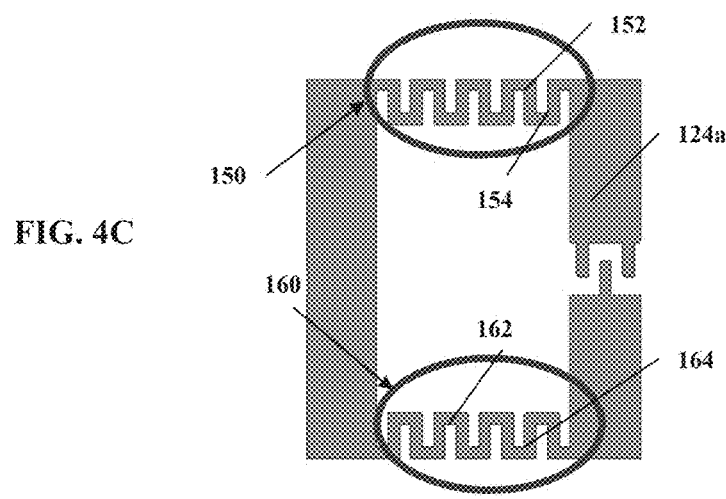
FIG. 4C is a schematic diagram showing the Miniaturization—Meandering.
Figure 4D:
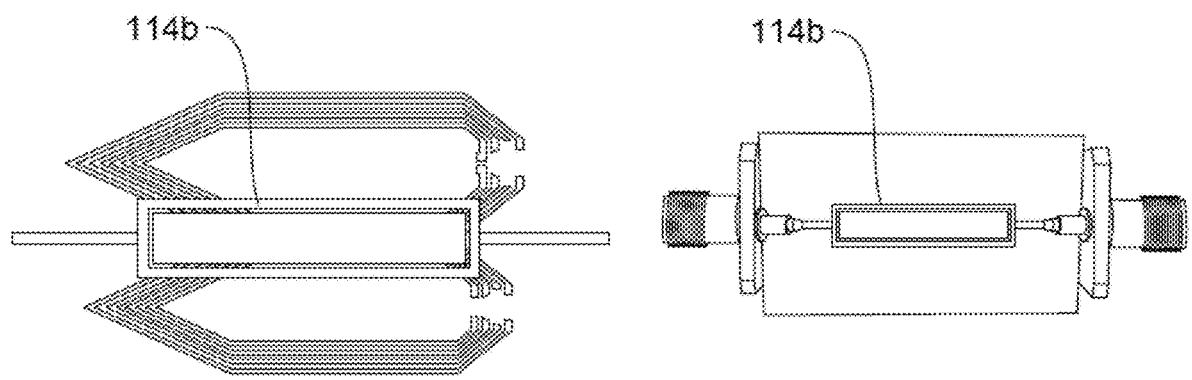
FIG. 4D is simulated and fabricated structure of an alternative embodiment of the feeding line.

In one embodiment, the top layer 110b is comprised of a conductive path or conductive trace connecting the first port 116b and the second port 118b. In one embodiment, the feeding line 114b is tapered for more coverage and includes a middle portion with a width of about 3 mm and the first port 116b and the second port 118b is about 1.5 mm. The tapering provides for more coupling and the widths of the middle portion and the first and second port may be adjusted. In another embodiment, the feeding line 114b includes a non-tapered design, as shown in FIG. 4D. The feeding line 114b includes a general rectangular network with an inner rectangular gap that can be used for the same purpose. To increase the coupling of the slots two topologies are considered. These were implemented on two different substrates. One method consists of increasing the width of the transmission line to cover all the slots Another method consists of using an additional rectangular resonator to cover all the slots In one embodiment, the bottom layer 120b is comprised of a ground plane. Eight slots are etched from the ground plane that represents the eight resonators 122b. These resonators 122b have different lengths, and the resonators 122b operate at different frequencies, leading to the multi-band response. The lengths of resonators are detailed below in Table 4a.

TABLE 4A

| | Largest resonators | | | Smallest resonators |
|---|---|---|---|---|
| Upper batch Length (mm) | 45.4 | 41.2 | 35.45 | 31.75 |
| Lower batch Length (mm) | 49 | 43.5 | 38.1 | 33.1 |

Figure 5C:
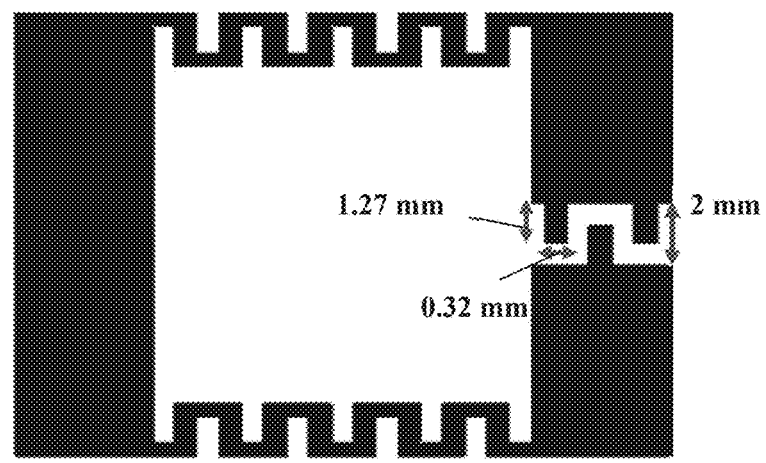
FIG. 5C is a schematic diagram showing the largest resonator.
Figure 5E:
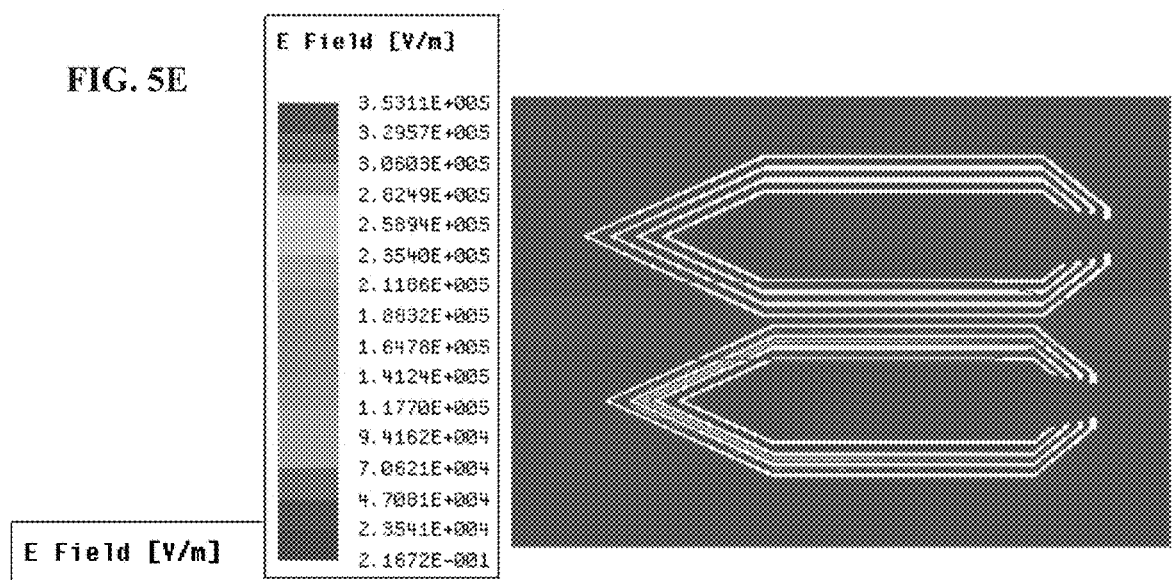

In one embodiment, the bottom layer 120 represents the sensing area. The method of sensing comprises placing one OLR 122b near the material of interest or blood stream to cause a specific shift in frequency and quality factor. This shift the EM properties enable the resonator 122b to monitor and detect the variation of the concentration of the blood constituent. In one embodiment, placing eight resonators increases the number of resonance frequencies and hence increase the sensitivity to the changes and variations. This increase in resonance frequencies and increase in sensitivity is shown in FIG. 5D-5E, by increasing the number of slots, the fields magnitude increases, leading to a better sensitivity. For one embodiment, frequency f is about 2.1 GHz the maximum E Field attained is increased from about 17.5 KV/m to about 697 KV/m In one embodiment, the OLRs 122b include the slots (resonators) follow the distribution of the veins and arteries; enhance the detection of variation of the concentration of the blood constituent compared to other embodiments that do not follow the structures of interest. In one embodiment, the biomarker sensor 100b is a multi-band reject sensor, where each slot covers a section of the ulnar veins and/or arteries. In another embodiment, the resonators are designed to follow other veins and arteries located at different positions in the body.

Figure 6C:
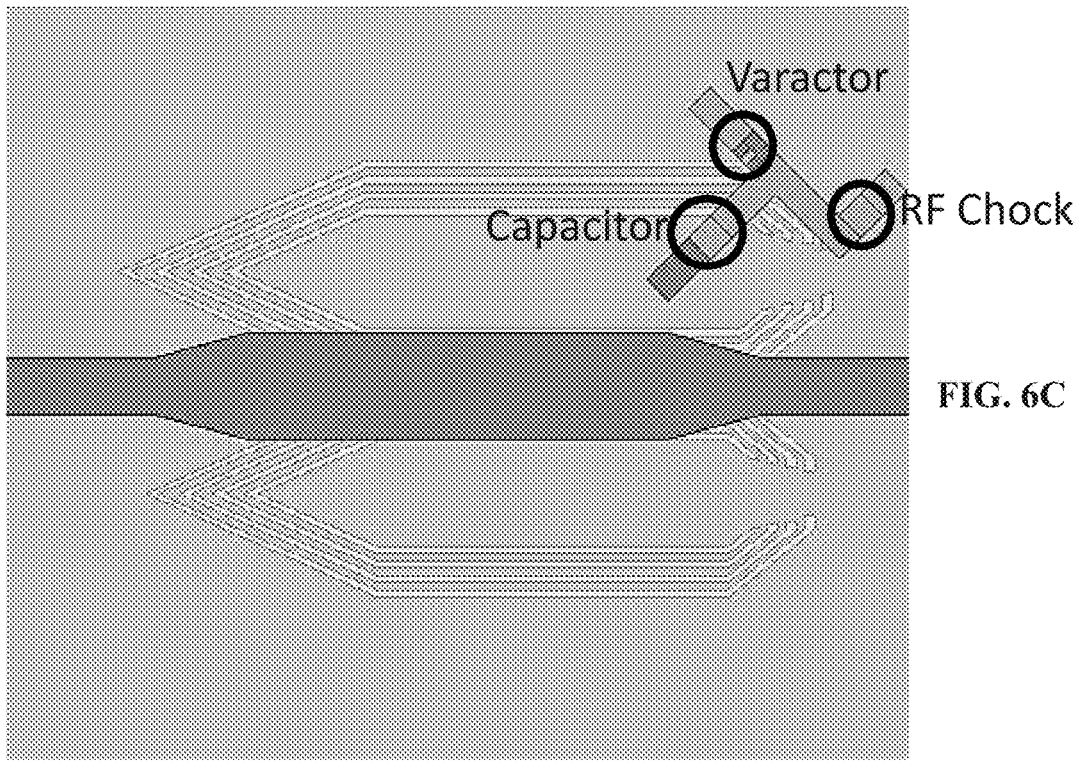
FIGS. 6C-6D are simulated and fabricated structure with reconfiguring components.
Figure 6D:
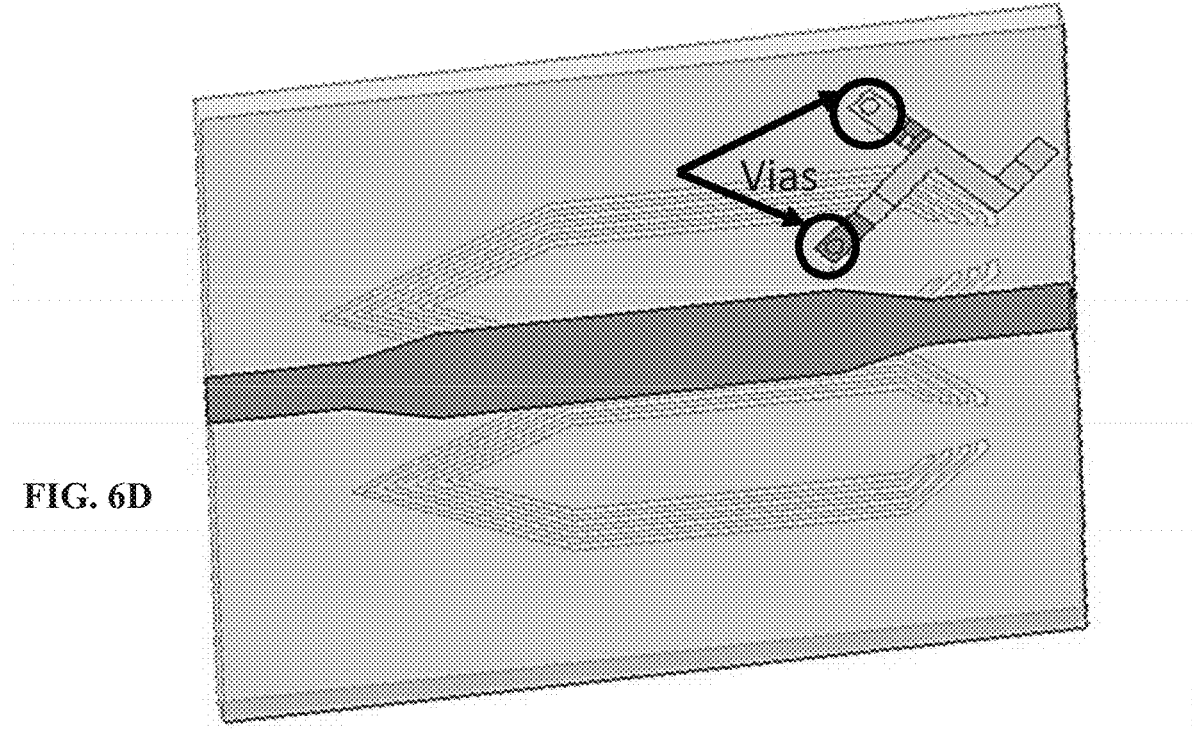

In one embodiment, the biomarker sensor 110b includes a reconfigurable frequency, which allows the sensor to continuously cover all the frequencies between about 1.5 GHz and about 2.5 GHz. In one embodiment, the reconfiguration of the biomarker sensor 110b is controlled by a plurality of varactors and/or digitally tunable capacitors with a maximum applied voltage of about 5 volts. In one embodiment, the plurality of varactors and/or digitally tunable capacitors are placed at the top layer 110b of the biomarker sensor 110b. The plurality of varactors and/or digitally tunable capacitors are separated from the sensing area on the bottom layer 120b and do not affect the sensitivity of the biomarker sensor 110b. In one embodiment, the reconfiguring components in claim 13 can be placed as in FIGS. 6C-6D. The varactor controls the resonators frequency of operation through two vias located in strategic positions. The capacitor used is a DC block, and the inductor is an RF chock. A varactor is a varicap diode, varactor diode, variable capacitance diode, variable reactance diode or tuning diode is a type of diode designed to exploit the voltage-dependent capacitance of a reverse-biased p-n junction.

In one embodiment, when the feeding topology changes or upon reconfiguration, the sensor performance changes. An attached circuit to the device can detect the response at a sweep of different frequency over the pre-defined range of operation. The response at the different frequency ranges is then used to develop a model to predict glucose levels.

In one embodiment, the signal measured from the biomarker sensor 100b is converted using a computer program that allows the transformation of the magnitude and the phase of the reflected and/or transmitted signals into concentration of the blood constituents via trained models.

The response of the sensor is expected to change from one patient to another depending on many criteria, including, but not limited to: Skin thickness, color, type; Skin perfusion, hydration; Sweating; Patient metabolism and body mass index; and other medical conditions such as cholesterol, diabetes. Multiple resonances will help increasing the number of features, and hence will increase the sensitivity. The reconfiguration method will further improve the sensitivity of the sensor and make it more adaptable and personalized for different patients. The RF sensor is intended to be mounted along with different sensors (humidity, sweat, temperature . . . ), to reduce the effect of some undesired signals In one embodiment, the biomarker sensor 100b can detect the variation of permittivity hence it can be used in different applications including, but not limited to: Blood Glucose detection and any other blood markers, hydration monitoring/blood flow, Cholesterol, Bone fracture healing monitoring, Cardiac activity: heart rate, blood pressure; and material characterization.

The biomarker sensor 100b is connected to a wearable Vector Network Analyzer to detect the RF energy and convert it into phase and magnitude. For this biomarker sensor 100b, the measured metrics are the S11, S21, and S22. These parameters are recorded in the following forms: Magnitude, Phase, Impedance, Smith chart.

A method of predictive modeling for selection of critical features comprises connected the biomarker sensor 100b to a signal processing system to convert the magnitude and/or the phase into concentration of the blood constituents; using the biomarker sensor to measure the S-parameter; preprocessing the S-parameter data for outlier and noise removal using techniques selected from the group consisting of wavelet, moving average filters and other types of filters; extracting features by sampling S-parameters into different frequency components and normalizing the features between −1 and 1; removing the reference value, removing the mean of each metric, dividing by the maximum of each metric; modeling, calibrating and tuning by using regularized regression to predict the glucose concentrations selected from the group consisting of Lasso, PLS, and Hybrid models; preparing single feature model and multiple-feature model, time based models; and recalibrating the models for enhanced accuracy.

Figure 7A:
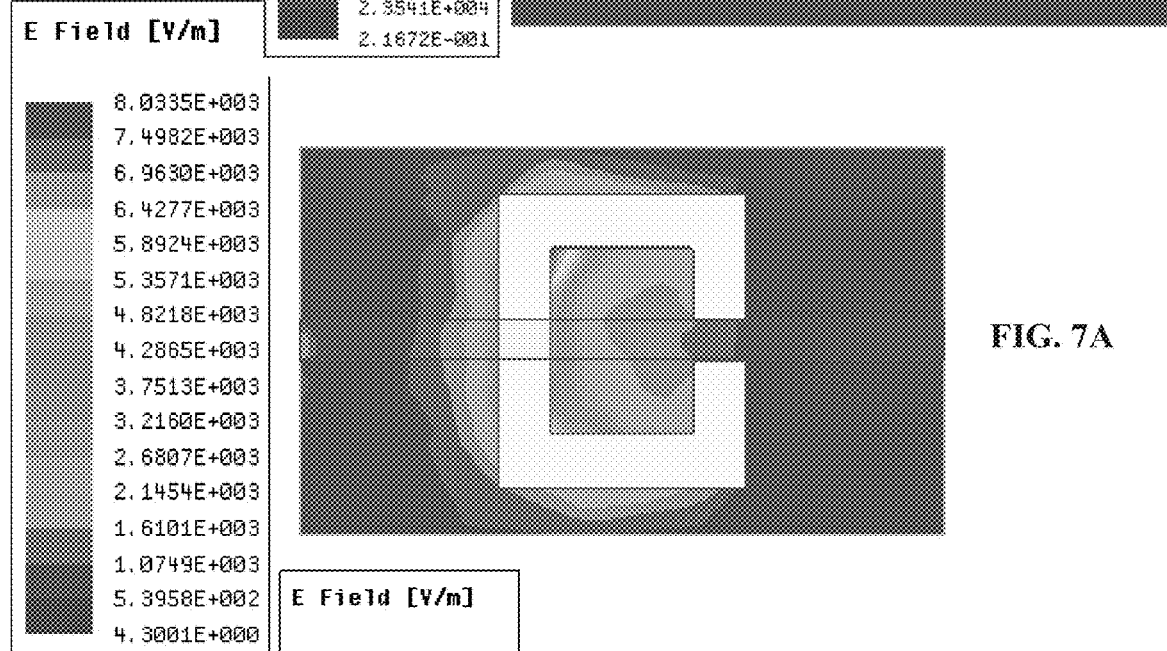
FIG. 7A is a graph showing the Electric field intensity showing the sensitivity of high magnitude fields within small areas of a regular open loop resonator.
Figure 7B:
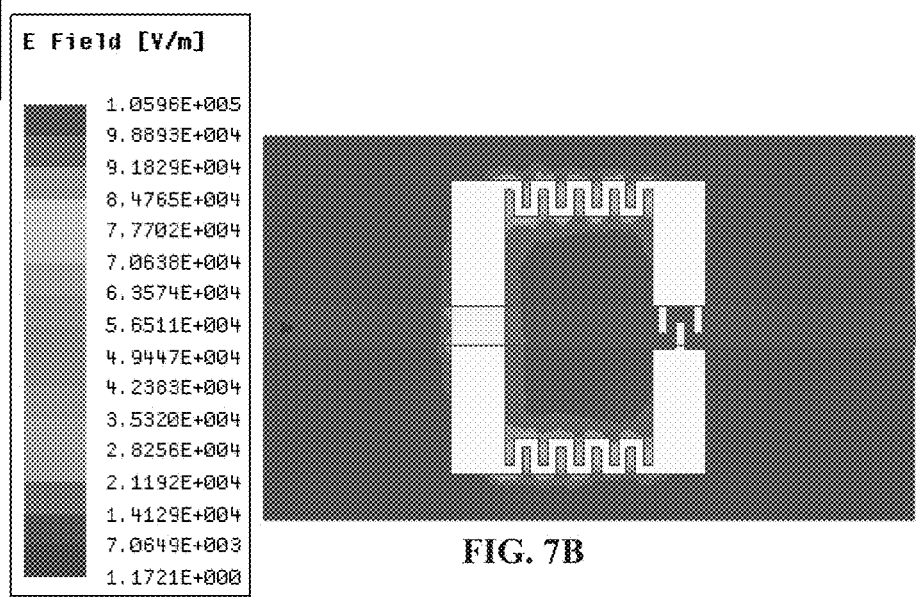
FIG. 7B is a graph showing the Electric field intensity showing the sensitivity of high magnitude fields within small areas of a meandered and perturbed open loop resonator.
Figure 7C:
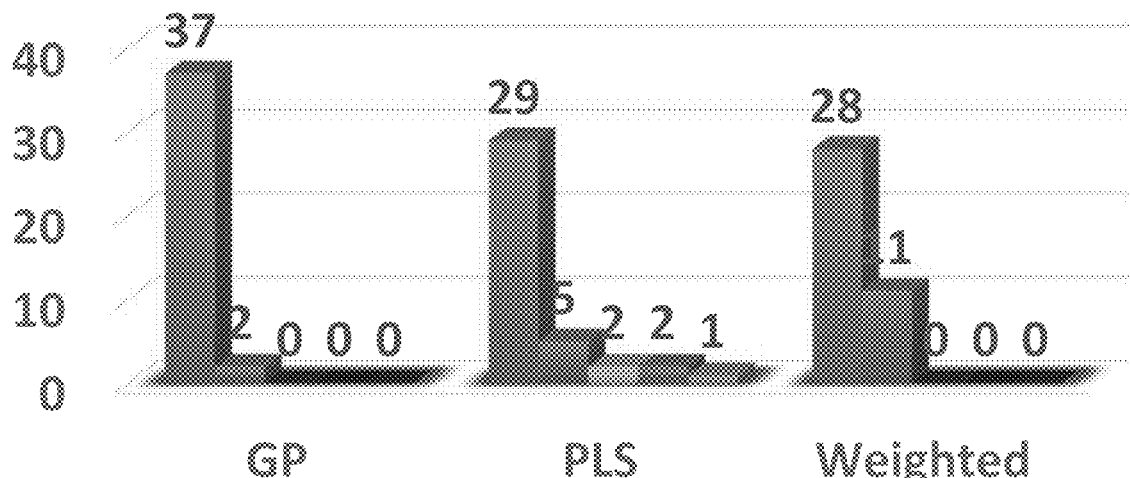
FIGS. 7C-7D are graphs for the Clarke Error Grid Output and the Clarke's Error Grid Analysis for the serum measurements for the biomarker sensor 100$b$ with a rigid substrate for the GP, PLS< and weighted PLS models.
Figure 7D:
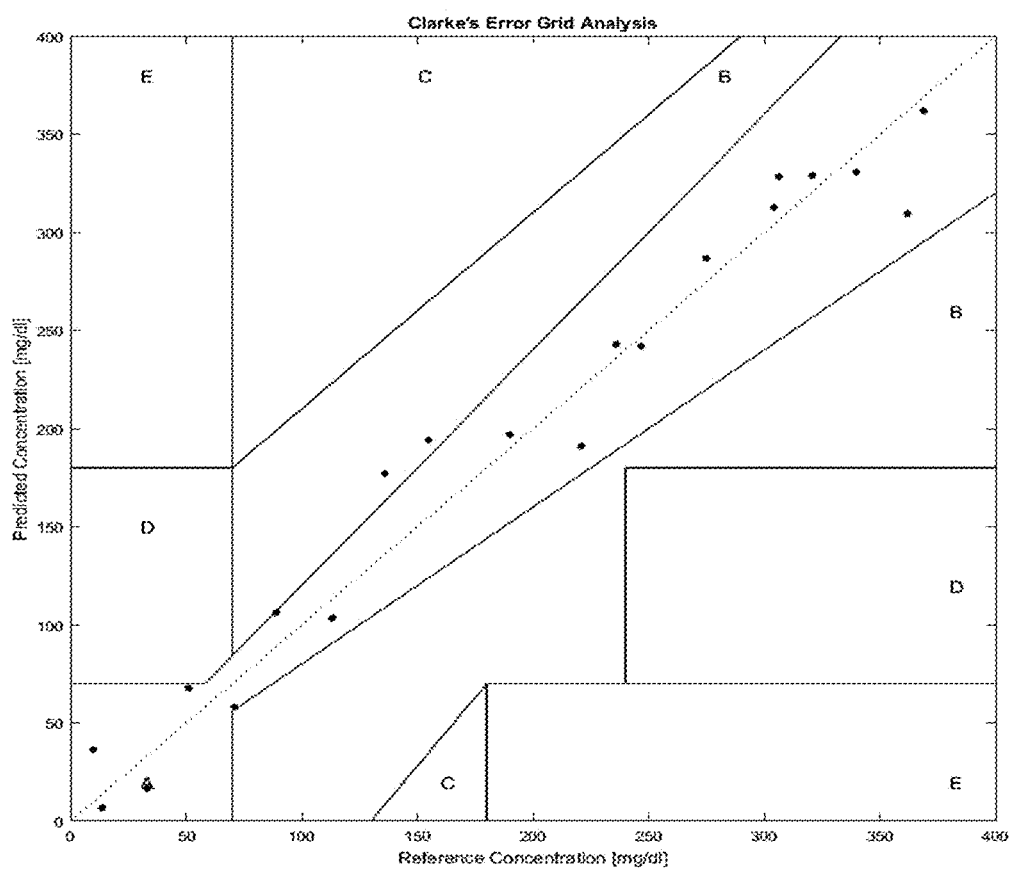
Figure 7E:
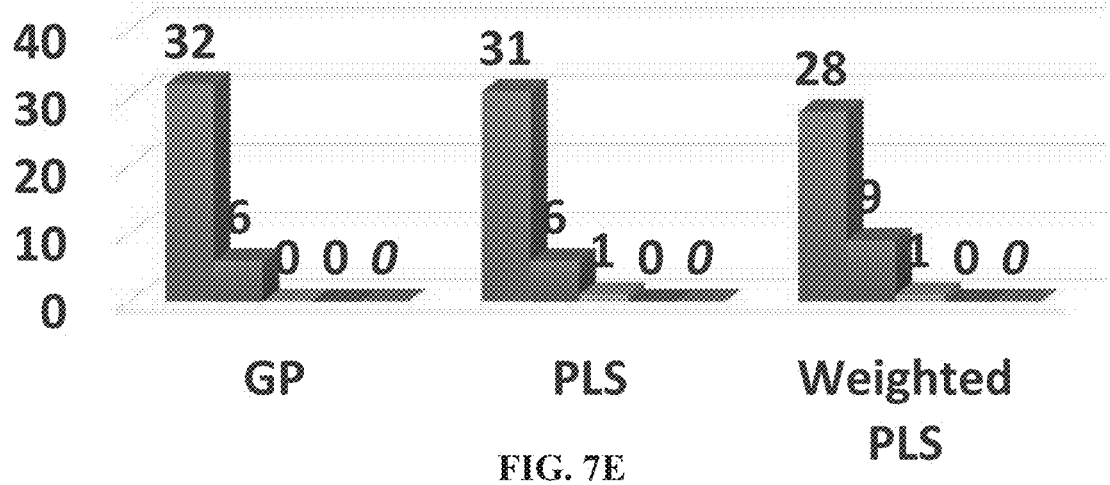
FIGS. 7E-7F are graphs for the Clarke Error Grid Output and the Clarke's Error Grid Analysis for the serum measurements for the biomarker sensor 100$b$ with a flexible substrate for the GP, PLS< and weighted PLS models.
Figure 7F:
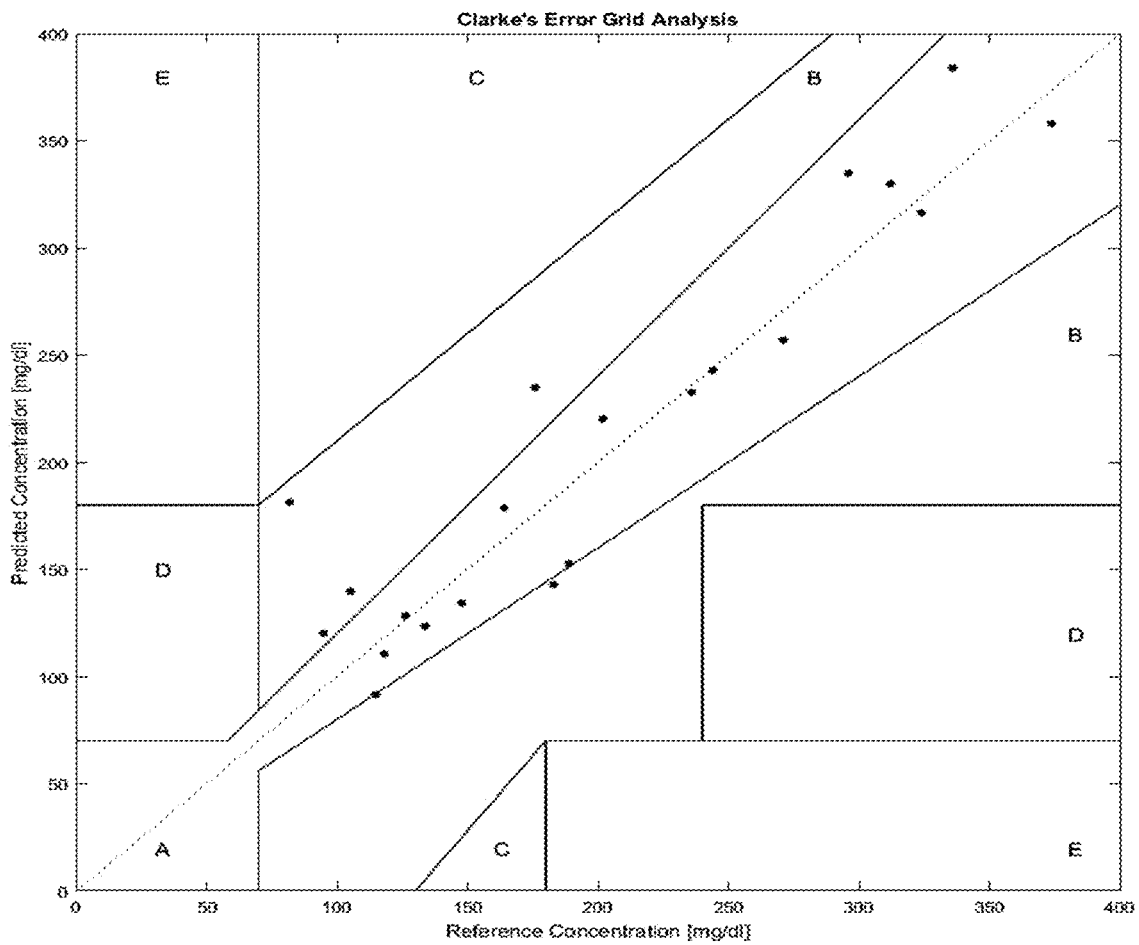

The serum measurements for the biomarker sensor 100b with a rigid substrate are shown in FIGS. 7C-7D for the GP, PLS, and weighted PLS models. The serum measurements for the biomarker sensor 100b with a flexible substrate are shown in FIGS. 7E-7F for the GP, PLS, and weighted PLS models.

The design features of the biomarker sensor 100b include Biologically inspired for higher sensitivity; tunable reconfigurable frequency; better S-parameters levels than any other multiband sensor in the literature with smaller size and the least required number of resonators; octa-band resonator (the most number of bands in the literature)→Better sensitivity for permittivity characterization.

The design features of the biomarker sensor 100b are tuned to adapt to the topology of the sensing structure to enhance its sensitivity; slots become more affected by changes within veins and arteries, and less affected by other neighboring variations. The shape of the slots follows the arms ulnar veins and arteries. This slot distribution increases the sensitivity of the biomarker sensor to the variation of the blood constituents' levels flowing in the veins and arteries. The multiple slots make the biomarker sensor 100b operational at eight frequencies between about 1.5 and about 2.5 GHz. These eight frequencies provide a practical window to detect the variation of the blood glucose level at different frequencies. Tunable frequency provides a practical window to detect the variation of the blood glucose level for different patients.

Broadband Response

The biomarker sensor as a broadband sensor allows measurements over wide frequency range and enable measuring the sensitivity, calibration and modeling over multiple frequencies using the same device thereby allowing model development to have a larger pool of candidate features to select among.

Furthermore, different patients will load the biomarker sensor differently, and the broadband sensor will be used on different patients. Consequently, the sensitivity of the response of the sensor would vary for different body compositions based on age, gender, weight as function of frequency. Therefore, there is need for a device capable of monitoring the shifts at a wide frequency range.

In order to ensure broadband behavior, two techniques were applied on the biomarker sensor 100. The biomarker sensor 100 includes a tapering 112 of the feeding line 114 which is present on the top layer 110. The first end 116 and the second end 118 of the feeding line 114 includes a width Wf wider than the width Wt of the tapering middle portion 112 of the feeding line 114, as shown in FIG. 1B. In one embodiment, the width Wf is about 1.9 mm and the width Wt is about 0.35 mm. A range for the width Wf and Wt may be varied between the middle tapered portion, as detailed in step 9 below.

Determining the total length of the substrate is governed by the topology of the human arm where the filter will be placed as well as the dimension of the resonators and the number of resonators N. In one embodiment, the width of the substrate to be about 18 mm. Governed by this width, the substrate length ($L_{sub}$) is determined as follows (in the embodiment of about 60 mm) based on the number of resonators.

1. Compute as discussed below based on the desired band, N, the number of resonators.
2. Determine from the wavelength of the lower frequency band, the total electrical length of the largest resonator $L_R=\lambda/2$ (eqn 4). Based on this length, we determined the length of the remaining resonators using equation (3).
3. All the resonators are centered in the middle of ground plane equidistant from both edges.
4. For the largest resonator, L1 is determined to be slightly smaller than width of the ground plane, and the remaining dimensions (W1) are determined such that the perimeter of the resonator is equal to $L_R$. In order to shrink the required length of the substrate, meandering is employed as a miniaturization technique as explained later.
5. The remaining resonators scale accordingly.
6. The total of the substrate $L_{sub}$ is determined from the different resonator dimensions Wi, and the spacing between the resonators. For better coupling it is desired to have the smallest possible spacing satisfying the fabrication limit, and a logarithmic scale as per equation 3. As such, we expect the spacing between the two smallest resonators to determine the rest.
7. We define $L=L_{sub}/2$,
8. We also define $Z_1$ according to equation (2new).

$$\Gamma = \frac{\ln\left(\frac{Z_l}{Z_0}\right)}{2} e^{-j\beta l} * \frac{\sin(\beta l)}{\beta l} \qquad (2new)$$

*obtained from [Microwave Engineering, by David Pozar, $4^{th}$ edition, Wiley.]

9. As such Wf and Wt can be determined.
10. Wf is determined from initial impedance Z0=50 Ohms. According to equation (3a)

$$Z_0 = \begin{cases} \frac{60}{\sqrt{\varepsilon_e}} \ln\left(\frac{8d}{W} + \frac{W}{4d}\right) & \text{for } \frac{w}{d} \le 1 \\ \frac{120\pi}{\sqrt{\varepsilon_e}\left[\frac{W}{d} + 1.393 + 0.667\ln\left(\frac{W}{d} + 1.444\right)\right]} & \text{for } \frac{w}{d} \ge 1 \end{cases} \qquad (3a)$$

$$\varepsilon_e = \frac{\varepsilon_r+1}{2} + \frac{\varepsilon_r-1}{2} \times \frac{1}{\sqrt{1+12d/W}}$$

d is the substrate thickness

Obtained from the same reference.

1. Wt is determined by Zl using eqn (3new)
2. The tapering, ie the intermediate width is determined by calculating the impedance at a given point from equations (1) and (2), and the intermediate width is determined from (3a).

The values are refined by simulation due to interaction between the line and the underlying structure.

The biomarker sensor includes a logarithmic periodic distribution of a complementary open loop resonators 122, which are located on the bottom layer 120 (as shown in FIG. 1A), with a plurality of slots 140 facing the skin. The order of the filter will vary by the number of open loop resonators, which can vary from one to any number. Given a desired design frequency band Bs for a specific application, the number of resonators is determined according to equation (1a).

$$N = 1 - \frac{\ln(Bs)}{\ln(1/r)}, \qquad (1a)$$

where $\Gamma$ is the logarithmic ratio which should be a number smaller than one, and we choose the value corresponding to the minimum number N of resonators that insures an overall S21 below—10 db over the whole band for the band reject filter.

In one embodiment, tapering increases the bandwidth of each resonator and consequently increases the bandwidth of the whole sensor. The tapering of the line followed an exponential distribution based on Equations (1) and (2):

$$Z(z) = Zoe^{a \times z} \qquad (1)$$

$$a = \frac{1}{L} \times \ln\left(\frac{Zl}{Zo}\right) \qquad (2)$$

Figure 3A:
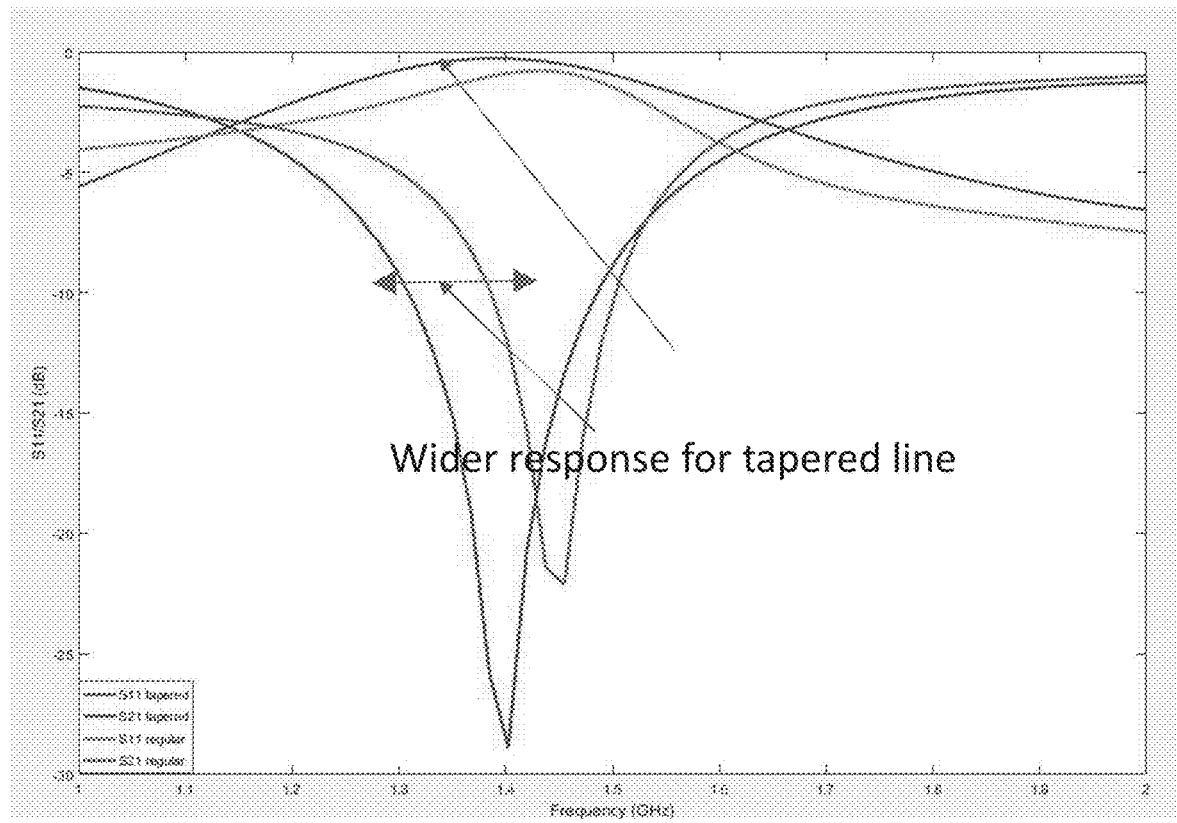
FIG. 3A is a graph showing the tapered transmission line without loss of generality, and a wider response for the tapered transmission line.

FIG. 2 shows comparison between regular feeding line 130 and tapered feeding line 112. Advantage of applying a tapered transmission line is shown in FIG. 3 where the tapered feeding line is without loss of generality, example demonstrates case of one element.

Broadband Response—Logarithmic Scaling

The logarithmic structure includes the elements that are distributed logarithmically in size from small to large. This leads to a creation of frequency resonances that vary from upper to lower frequencies. Hence, a wider operation is achieved. In one embodiment, four, meandered, complementary (slot) open loop resonators 122a, 122b, 122c, 122d that follow a logarithmic distribution are disposed on the bottom layer 120, as shown in FIG. 1B. The first resonator 122a includes a width W1 and a length L1, the second resonator 122b includes a width W2 and a length L2, the third resonator 122c includes a width W3 and a length L3, and the fourth resonator 122d includes a width W4 and a length L4. The distance S1 is between the first resonator 122a and the second resonator 122b, the distance S2 is between the second resonator 122b and the third resonator 122c, the distance S3 is between the third resonator 122c and the fourth resonator 122d. The first resonator 122a includes a distance g1 for first slot 144a. The first resonator 122a includes a first slit 124a, the second resonator 122b includes a second slit 124b, the third resonator 122c includes a third slit 122c, and the fourth resonator 122d includes a fourth slit 122d. The first slit 124a includes a separation distance g1, the second slit 124b includes a separation distance g2, the third slit 124c includes a separation distance g3, and the fourth resonator 124d includes a fourth slit 124d. In one embodiment, the Width W1 is about 20 mm, the length L1 is about 14.7 mm, distance S1 is about 13.15 mm, and the separation distance g1 is about 2 mm. Equations (3) and (4) determine the effective width and length ratios between the different resonators based on the targeted frequencies. Miniaturization techniques as will be discussed next will further help adjust and shrink the physical widths and lengths of the structures. The biomarker sensor 100 includes a length Lb and width Wb. In one embodiment, the length Lb is about 60 mm and the width Wb is about 18 mm. The first slit 124a, second slit 124b, the third slit 124c, and the fourth slit 124d are all perturbed, which includes a forked The dimensions of these resonators are logarithmically dependent on frequency with a scaling factor τ=0.88. The dimensions and spacing of these OLRs follow a log-periodic distribution as given in (3), where τ is a scaling factor that affects the desired impedance bandwidth B for the four required OLRs in the proposed design [5]. Moreover, the electrical length of the largest OLR is taken to be one-half the wavelength of the lowest desired frequency of operation as shown in (4). For τ=0.138 and using (3) and (4), the dimensions of the proposed filter configuration are illustrated in FIG. 1B.

$$\frac{Wn+1}{Wn} = \frac{Ln+1}{Ln} = \frac{1}{\tau} \quad (3)$$

$$L_{max} = \frac{\lambda_{min}}{2} = \frac{v_p}{2 \times f} \quad (4)$$

Broadband Response—Bank of Resonators

In one embodiment, at least four open loop resonators 122a, 122b, 122c, 122d of different dimensions are integrated in the biomarker sensor. For a given application, the number of resonators is determined by the sensitivity of the underlying application, the desired frequency range of operation and the physiological constraints of the human topology and the limitations of the miniaturization techniques. As such, less than four open loop resonators may be used and greater than four open loop resonators may be used, such as 2, 3, 5, 6, 7, 8, 9, or 10 open loop resonators according to one embodiment. By implementing at least four resonators 122a, 122b, 122c, 122d, at least four resonances are introduced to the biomarker sensor. The resonant behavior of the loop is ensured by creating a slit 124a, 124b, 124c, 124d in the loop, as shown in FIG. 1A. These four resonances combined allow achieving the broadband response.

In one embodiment, the biomarker sensor is a double-sided microstrip structure that operates as a broadband reject filter as shown in FIG. 1B. The top layer consists of an exponentially tapered transmission line that couples the magnetic flux density to the underneath resonators. The feed line is optimized based on the tapering techniques discussed by the author in [4] to better enhance the broadband operation of the filter. The bottom layer of the filter is a defected ground plane that includes four complementary OLRs.

Broadband Response—Open Loop Resonator

In an open loop resonator, when the material under test or biomarker is placed near the resonator, a perturbation in the resonant frequency occurs. This translates into a shift in frequency and quality factor of the resonator. Based on the shift in frequency and magnitude of the transmission and the reflection coefficients at different frequencies, the permittivity and the loss tangent of the material can be extracted, and hence the variation in the blood composition in general, and the glucose level in particular.

In one embodiment, the Broadband rigid filter operates with a broadband response between about 1.25 GHz and about 2.25 GHz with a rigid filter top and bottom layer. In the same embodiment, a rigid filter is designed on Roger RT/Duroid 3006 of permittivity ε=6.15 and thickness h=1.27 mm. The rigid material is laminates ceramic-filled PTFE composites for excellent stability of dielectric constant over temperature including the elimination of the step change in dielectric constant and exhibits a low dissipation factor.

In another embodiment, a flexible filter top and bottom layer is designed on Roger RT/Duroid 3003 of permittivity ε=3 and thickness h=0.25 mm. In another embodiment, the flexible filter top and bottom layer can also be made on adhesive-flexible material such as silicon layers and the like.

Miniaturization

In one embodiment, the biomarker sensor may be placed on the human body or an animal for testing purposes. A small compact size ensures patient's comfort and portability. Accordingly, a miniaturization technique was used to decrease the size of the filter. The reduction in size was achieved by adapting meandered lines. For one embodiment, the total are size: is about 6×2×1.27 cm$^3$.

In one embodiment, the length of the resonator is set to be half-wavelength at the operating frequency. Meandering increases the curvature of the lines 150 resulting in an increase in the fringing of fields. FIG. 4C is a schematic diagram showing the Miniaturization—Meandering of the top line 150 and the bottom line 160 on the resonator 124. The meandering of the top line 150 and the bottom line 160 is identical, according to one embodiment. The meandering includes a general S-shape or sinusoidal pattern. The S-shape includes at least three peaks 152, 162 and at least three valleys 154, 164, as shown in FIG. 4. In other embodiments, more than three peaks and more than three valleys may be employed for meandering, alternatively, less than three peaks and less than three valleys may be employed. Consequently, the microstrip would appear electrically longer in length. Accordingly, less physical size would be needed for the same resonance frequency. By using meandering, in one embodiment, a size reduction of up to 60% is achieved.

As shown in FIGS. 4A-4B, Wh be the unmeandered horizontal stretch of the wire. (Wh+L1)*2=resonator length $L_R$. WL1=width of the vertical stretch L1. WL1 determined the height of the turn of a meandered line. Let W11 be minimal realizable width of a turn (due to fab limits). W11 is desired to be as small as possible to maintain high coupling. Then the number of turns can be derived from Wh=2*(W11±WL1)*Number of turns. For our design, the smallest resonator will have the smallest possible W11 which is restricted by fabrication. As such, the other resonators will maintain the same number of turns but will scale W11 according to their respective size ratios.

High Sensitivity

The changes in permittivity relative to changes in the blood glucose levels are limited. Therefore, the biomarker sensor must enhance the sensitivity to these variations in order to ensure correct prediction of the actual glucose levels. This is achieved by concentrating the electric field distribution in strategic locations on the material under test (MUT). To increase the sensitivity of the proposed resonators, two strategies were employed: (1) Use complementary resonators instead of the normal ones [6]; and Perturb the open ends of the resonators [7]-[9].

High Sensitivity—Large Surface of Interaction Between Fields and MUT

For a normal structure of resonators, the electric field is mostly confined between the traces (s, g, t), as shown in FIG. 5B, which has a Low interaction with the material to be tested. By using the complementary structure (introducing slots at the bottom layer), as shown in FIG. 5A, the electric field is spread and is easily affected by the permittivity of the material (more sensitive to permittivity); and a separation between the transmission line and the sensing area is introduced by placing the transmission line on the upper layer (easier to implement on human body).

In one embodiment, high sensitivity can be achieved with a High Magnitude of fields within small areas. Further, by introducing perturbations at the open ends of the resonators, the fields magnitude increases and become stronger within small areas while still spread in the other areas. The width of the fork structure is limited by fabrication; as such at least 3 fork edges may be included in one embodiment. The length is determined by sweeping electromagnetic simulations to allow for proper matching in the presence of the perturbation. The dimensions of the perturbations in the example embodiment are presented in FIG. 5C for the largest OLR, according to one embodiment.

The combination of both meandered lines and perturbed ends increases even more the magnitude of fields allowing enhanced sensitivity to critical areas placed in contact with these regions of the device (such as: main veins). This embodiment improves the sensitivity of the sensor to permittivity variations, where higher fields concentrations is equivalent to better sensitivity, as shown in Table 1.

TABLE 1

| Configuration | E field (V/m) |
| --- | --- |
| 1. Simple | ~8e3 |
| 2. Meandered and perturbed end | ~1e5 |

For dielectric characterization, the sensitivity of the biomarker sensing filter is linked to both distribution and magnitude of the induced electric field across the complementary OLRs. In one embodiment, better sensitivity is achieved by inducing strengthened fields across the largest possible area [6]. To upsurge such distribution, the configuration of the embedded resonators is modified as shown in FIGS. 6A-6B. This helps spread the induced fields across the ground plane, and hence causes a higher interaction with the loading MUT. Furthermore, by perturbing the resonators, the magnitude of the induced fields tends to increase and get confined within small areas thereby leading to enhanced sensitivity levels. In addition, reducing the overall size of the filter requires the implementation of miniaturization techniques such as line meandering. The size of the modified OLR is 30% less than that of the conventional structure at 1.43 GHz.

FIG. 7A is a graph showing the Electric field intensity showing the sensitivity of high magnitude fields within small areas of a regular open loop resonator with a Max E field ~8000 V/m². FIG. 7B is a graph showing the Electric field intensity showing the sensitivity of high magnitude fields within small areas of a meandered and perturbed open loop resonator with a Max E field ~100000 V/m².

In one embodiment, the biomarker sensor includes a high sensitivity with a high concentration of current within small areas. Similarly, the embodiment configuration also improves the current magnitude, as shown in Table 2.

TABLE 2

| Configuration | Current density I (A/m²) |
| --- | --- |
| 1. Simple | ~100 |
| 2. Meandered | 600-1100 |
| 3. Meandered and perturbed end | 3000-6000 |

Figure 8A:
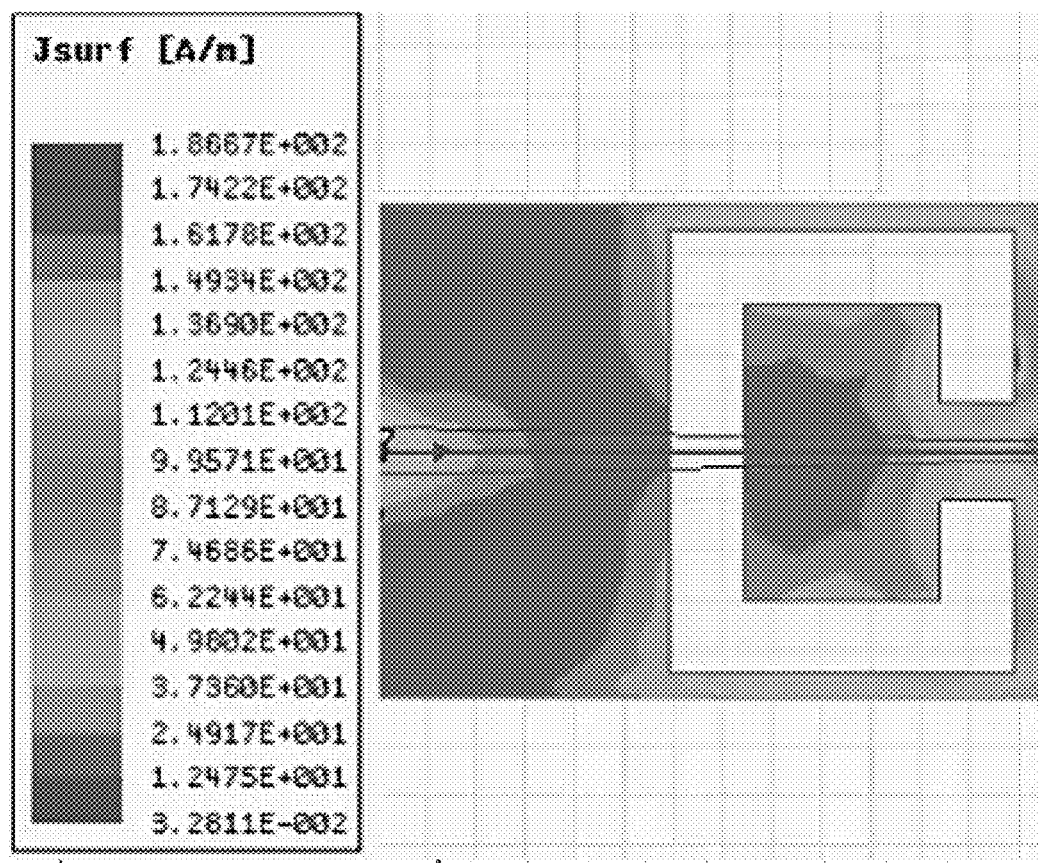
FIG. 8A is a graph showing the current distribution for a simple structure and a Sensitivity with a High Concentration of current within small areas.
Figure 8B:
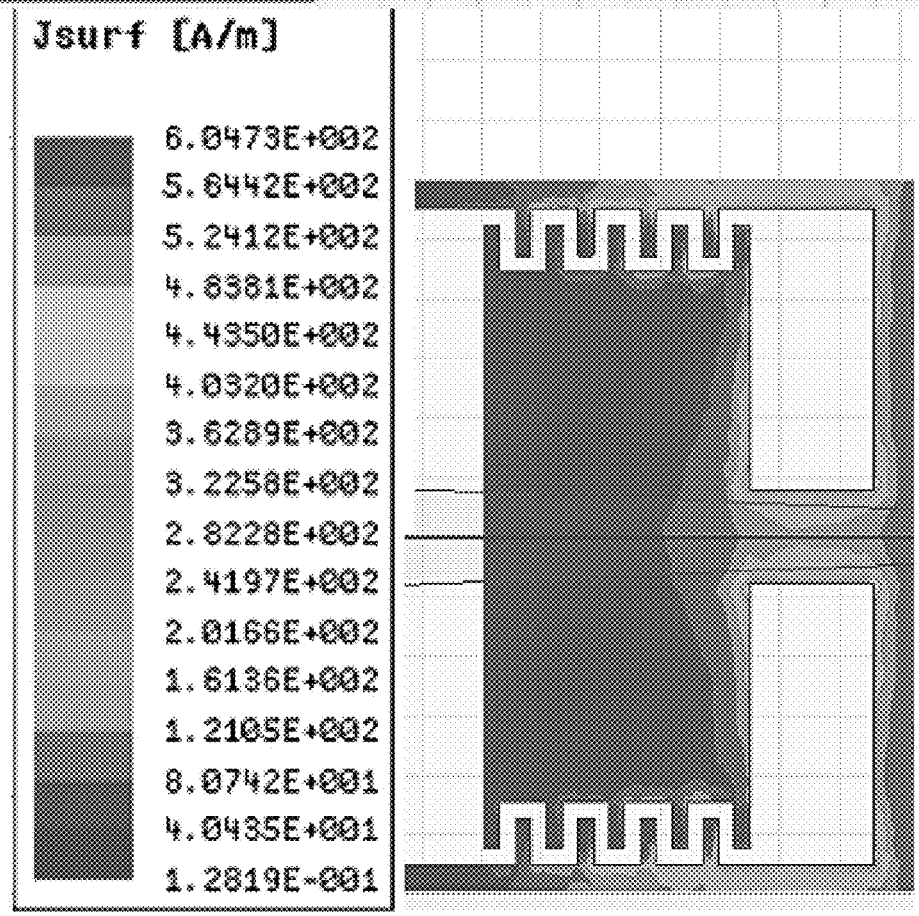
FIG. 8B is a graph showing the current distribution for a meandered only configuration and the Sensitivity with a High Concentration of current within small areas for the Meandered embodiment.
Figure 8C:
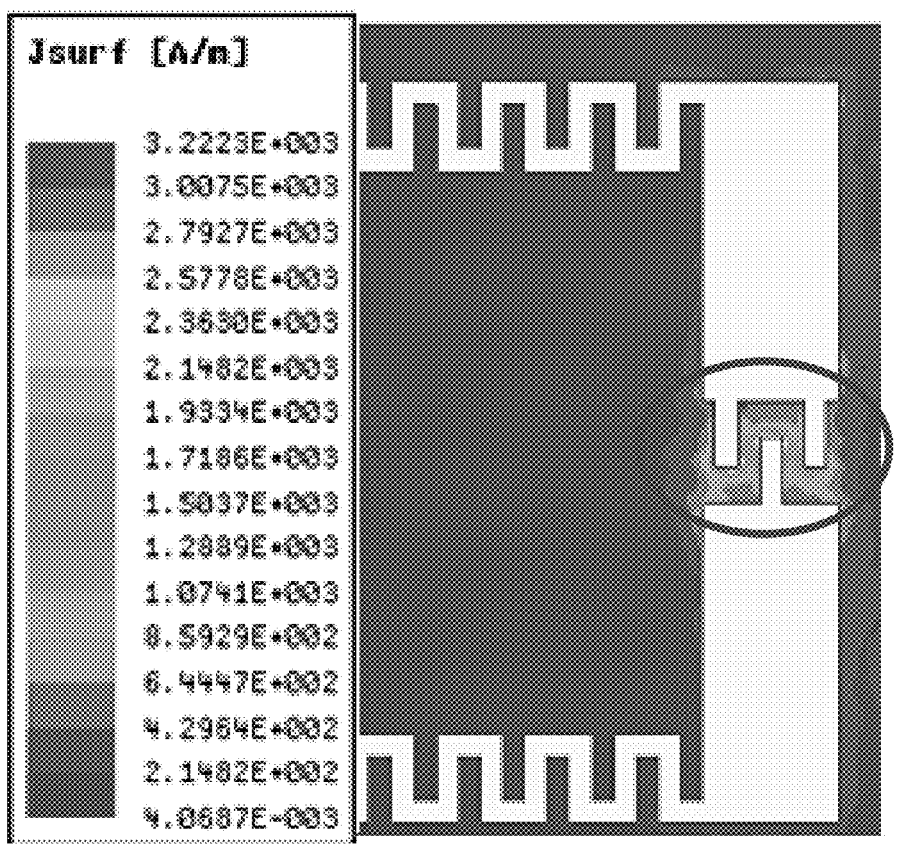
FIG. 8C is a graph showing the current distribution for meandered and perturbed embodiment showing the Sensitivity—High Concentration of current within small areas.

A Sensitivity with a High Concentration of current within small areas with a Simple structure is shown in FIG. 8A for the Current distribution for basic configuration with a Current density ~100 A/m². In one embodiment, the biomarker sensor includes a Sensitivity with a High Concentration of current within small areas for the Meandered embodiment is shown in FIG. 8B for the current distribution for meandered only configuration and a current density increased to ~600 A/m². In one embodiment, the biomarker sensor includes a Sensitivity—High Concentration of current within small areas for the Meandered and Perturbed embodiment is shown in FIG. 8C with a Current distribution for the final configuration and the current density increased to ~3,000 A/m². Current distribution for final configurations is shown in FIG. 8C.

Alternate Application

The biomarker sensor can detect the variation of permittivity. The biomarker sensor can be used to detect not only blood glucose levels, but also for different applications such as: Material/Liquid characterization, Detecting skin cancer and abnormalities, Detecting levels of different blood constituents including Cholesterol and Blood pressure, Monitoring cardiac activity such as Heart rate, EKG, and Blood pressure.

Measured Metrics

In one embodiment, the biomarker sensor is connected to a wearable Vector Network Analyzer to detect the RF energy and convert it into phase and magnitude. For this sensor, the measured metrics are the S11, S21, S12, and S22. These parameters are recorded in the following forms: Magnitude, Phase, Impedance, Smith chart. The RF energy includes an E-field that is disturbed for enhanced sensitivity capabilities.

Alternatively, a reflectometer, a trans receiver, an energy converter, a sensing surface, and an energy source may be used in all embodiments.

Predictive Modeling

In one embodiment, the biomarker sensor is connected to a signal processing system to convert the magnitude and/or the phase into concentration of the blood constituents. The signal processing system comprises measuring S11 and other parameters using the biomarker sensor to collect data; preprocessing of the data; removing the outlier and noise data; extracting features including, but not limited to: S11 Magnitude, S11 phase and/or impedance are sampled into different frequency components (features). The same is repeated for the other S-parameters. The signal processing system normalizes the features (−1 and 1); removes the reference value; centering at 0 (remove the mean of each metric); scaling (divide by the maximum of each metric). The signal processing system further comprises modeling, where one main part of the signal processing system is the predictive model that is used to estimate the levels of the body constituent. The predictive model is based on regularized regression. Both single feature model and multiple-feature model are considered. The signal processing system further comprises testing model accuracy using Performance Metrics.

Figure 9:
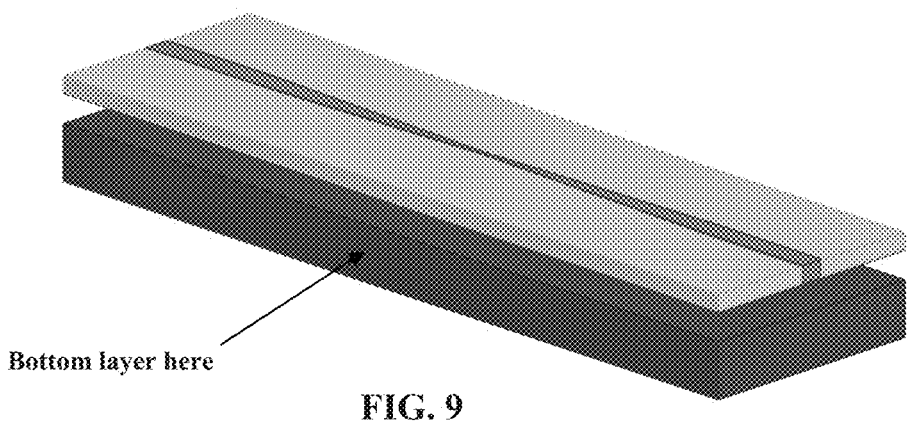
FIG. 9 is a schematic showing the Blood layer of thickness h=4 mm placed 2 mm beneath the filter for the Sensitivity test—simulations for the Rigid Filter embodiment.
Figure 10:
FIG. 10 is a side view of the schematic from FIG. 9.

As shown in FIG. 9-10, the Blood layer of thickness h=4 mm placed 2 mm beneath the filter for the Sensitivity test—simulations Rigid Filter. Variations in the permittivity of blood between 60<ε<75 and S-parameters phase and magnitude were recorded.

Figure 11:
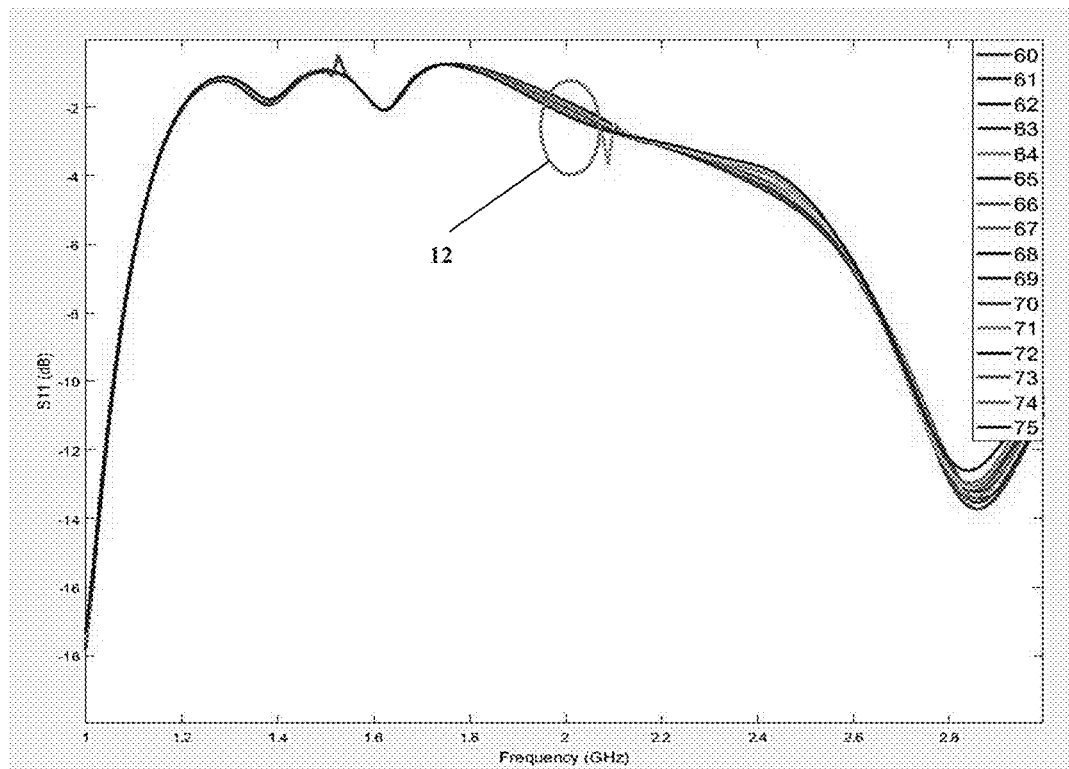
FIG. 11 is a graph of the Sensitivity test for the $S_{11}$ Magnitude is shown FIG. 11, which shows the change in the relative permittivity of blood (corresponding to varying the BGL).
Figure 12:
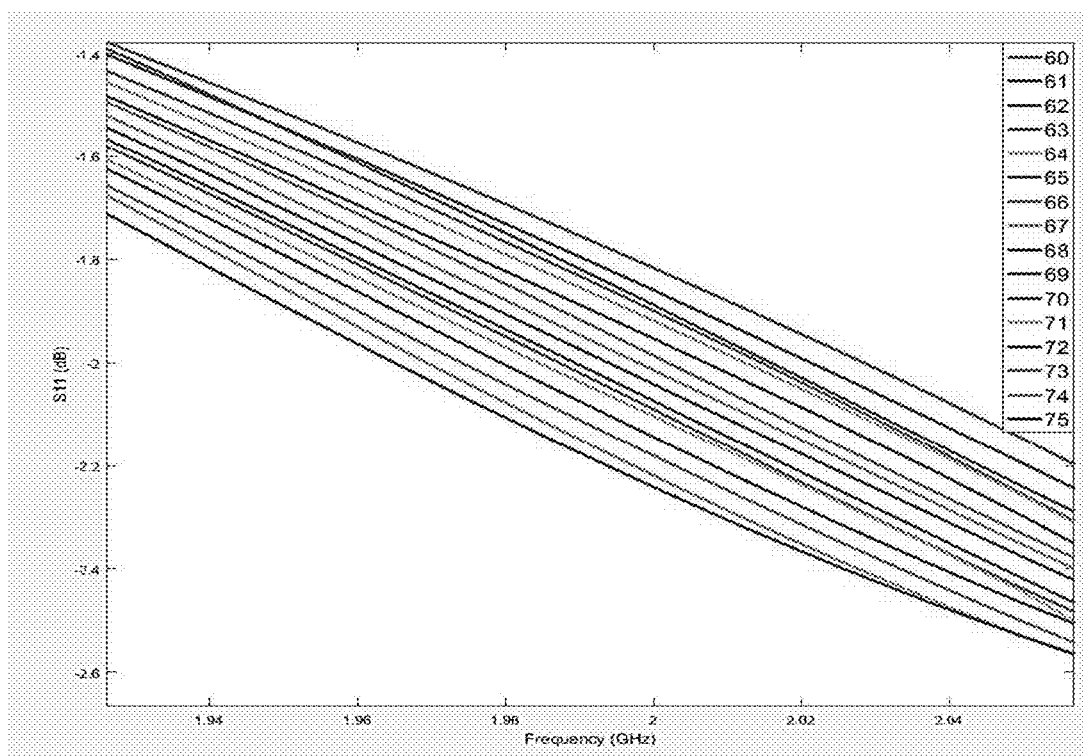
FIG. 12 is a graph of the one linear region from circle 11 in FIG. 11.
Figure 13:
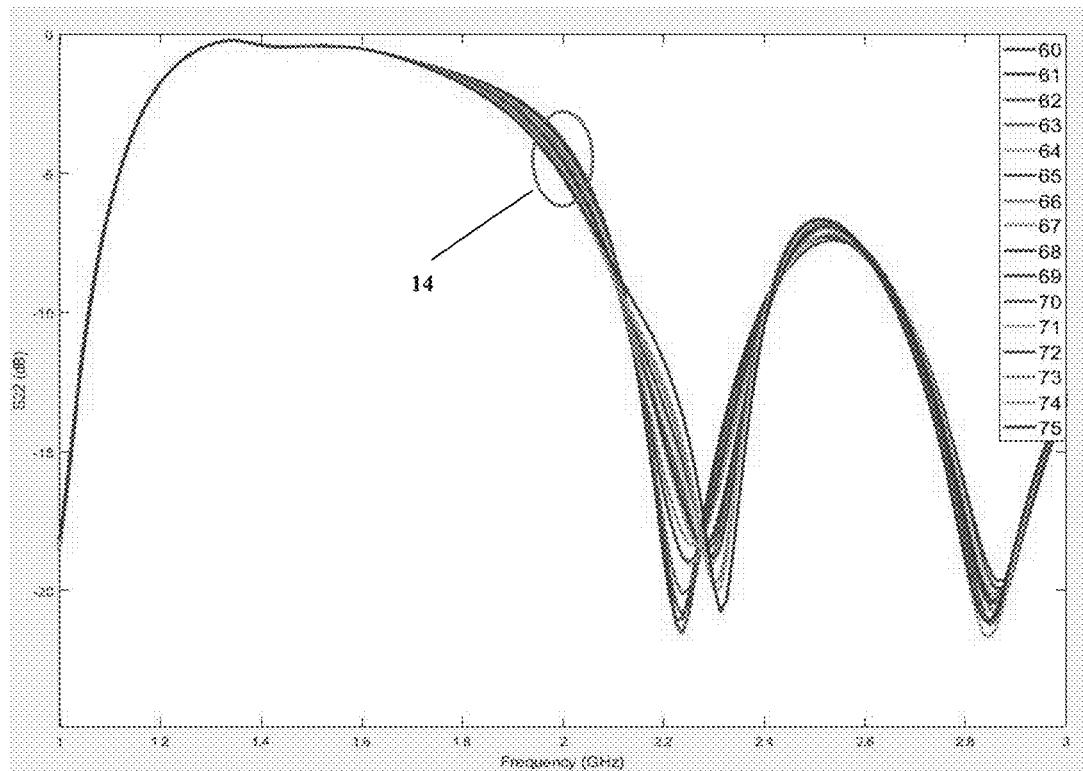
FIG. 13 is a graph of the Sensitivity test for the $S_{22}$ Magnitude, which shows the change in the relative permittivity of blood (corresponding to varying the BGL).
Figure 14:
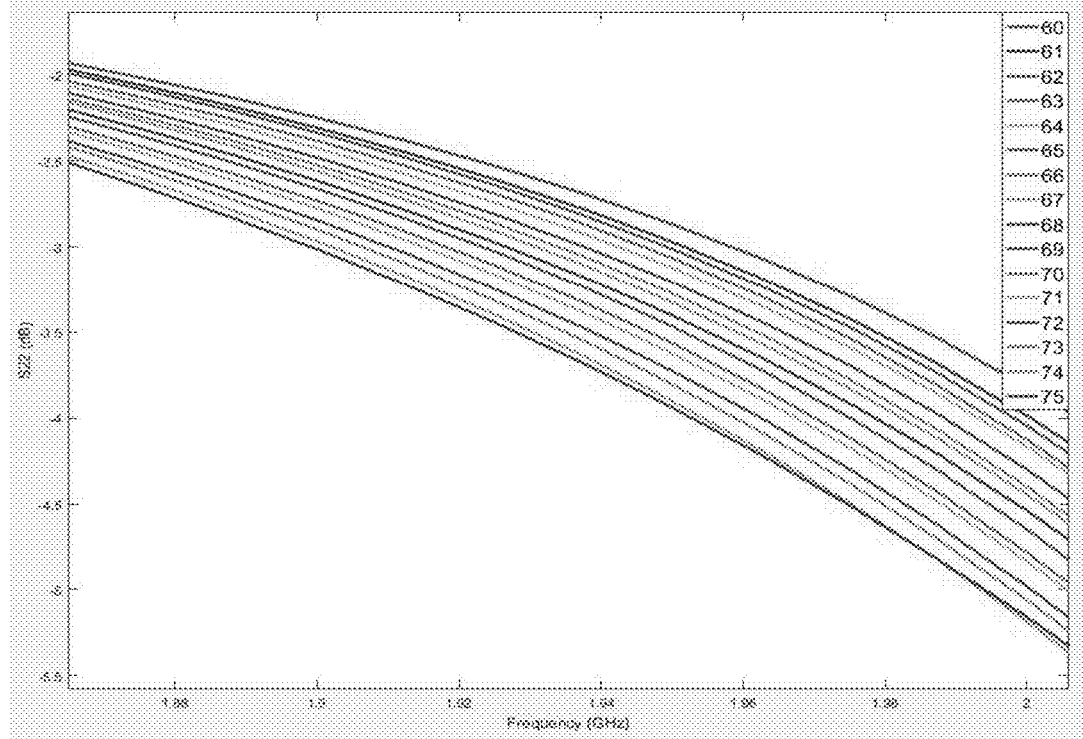
FIG. 14 is a graph of one linear region from circle 14 in FIG. 13.
Figure 15:
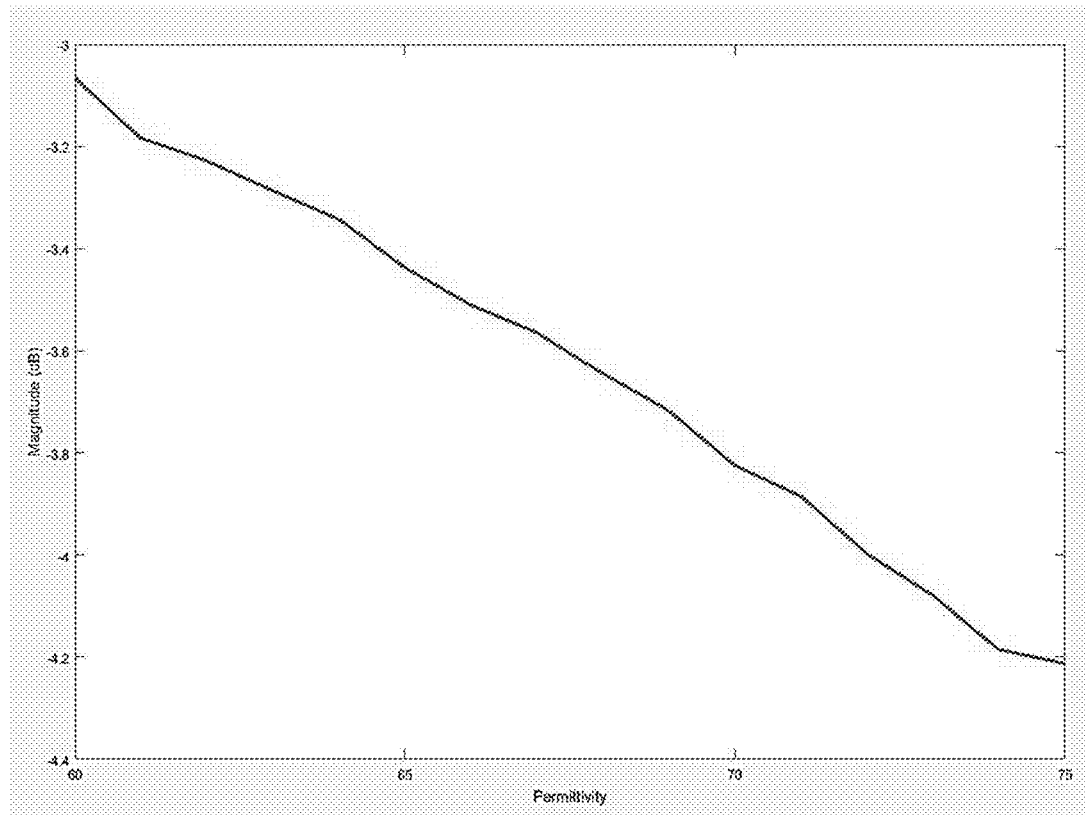
FIG. 15 is a graph showing the Relation between $S_{22}$ Magnitude and ε at 2 GHz, which shows the linear relation between the changes in permittivity and the corresponding shifts.
Figure 16:
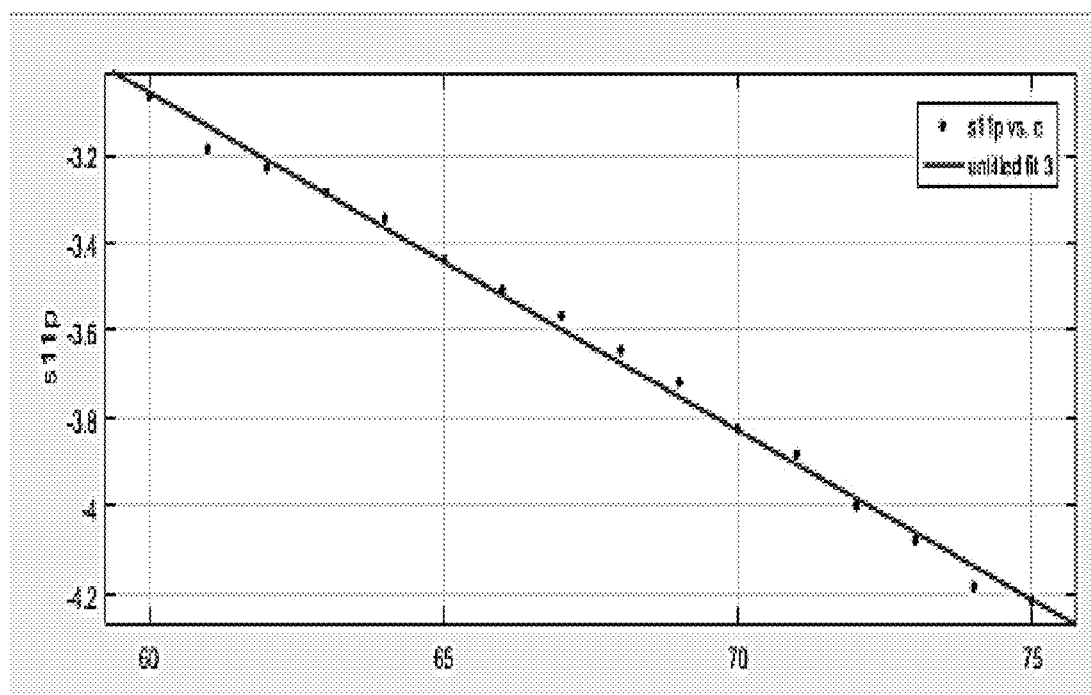
FIG. 16 is a graph showing the Curve fitting of the sample points using Matlab.

Example Sensitivity test—$S_{11}$ Magnitude is shown FIG. 11, which shows the change in the relative permittivity of blood (corresponding to varying the BGL). FIG. 12 is a zoom in on one linear region from FIG. 11. Example Sensitivity test—$S_{22}$ Magnitude is shown in FIG. 13, which shows the change in the relative permittivity of blood (corresponding to varying the BGL). FIG. 14 is a zoom in on one linear region from FIG. 13. The Relation between $S_{22}$ Magnitude and ε at 2 GHz is shown in FIG. 15, which shows the linear relation between the changes in permittivity and the corresponding shifts. And FIG. 16 shows the Curve fitting of the sample points using Matlab.

Figure 17:
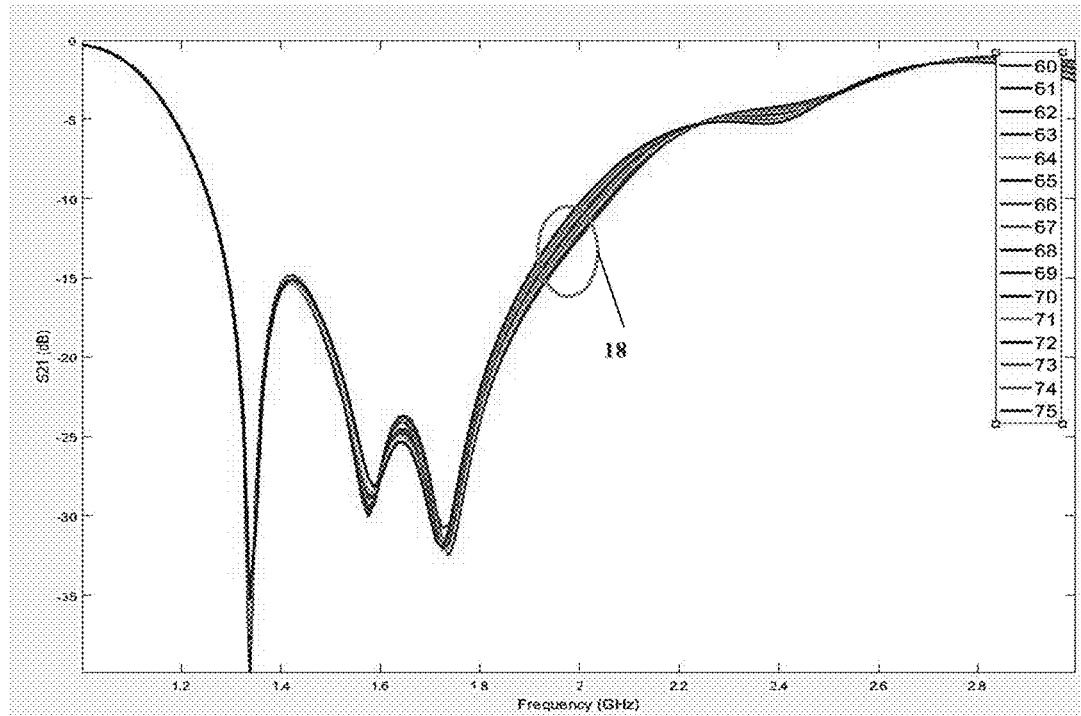
FIG. 17 is a graph showing the Sensitivity test for $S_{21}$ Magnitude, which shows the change in the relative permittivity of blood (corresponding to varying the BGL).
Figure 18:
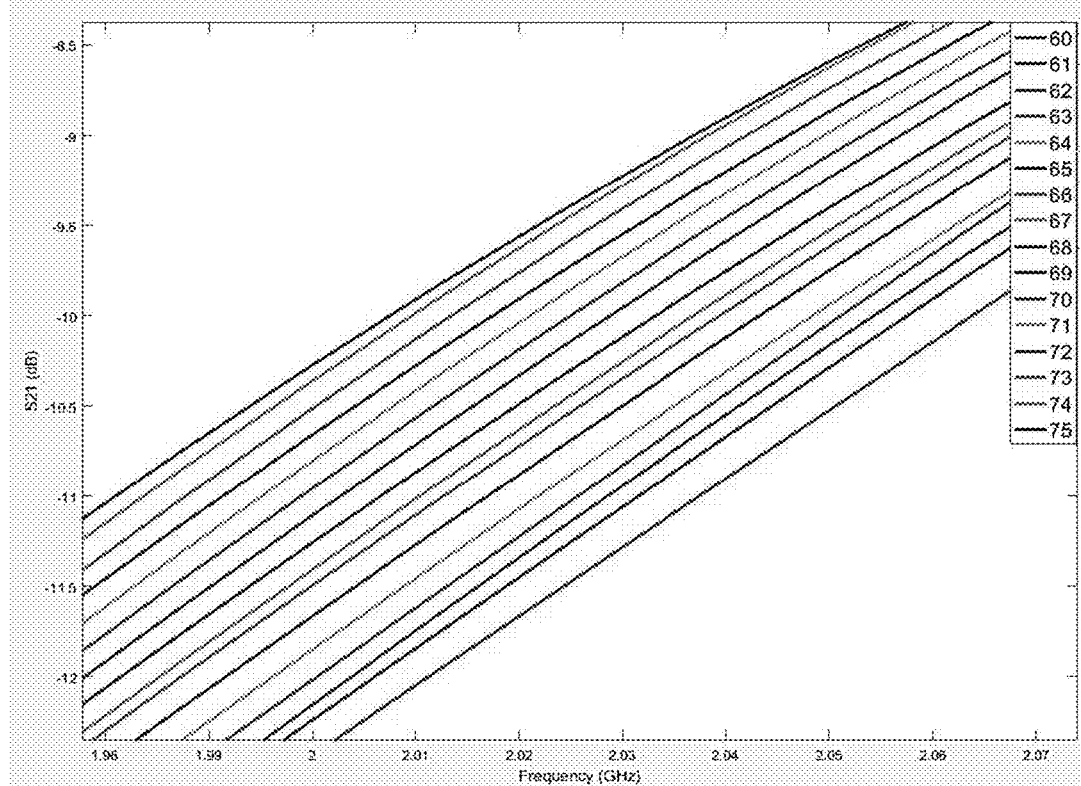
FIG. 18 is a graph showing one linear region from circle 18 in FIG. 17.
Figure 19:
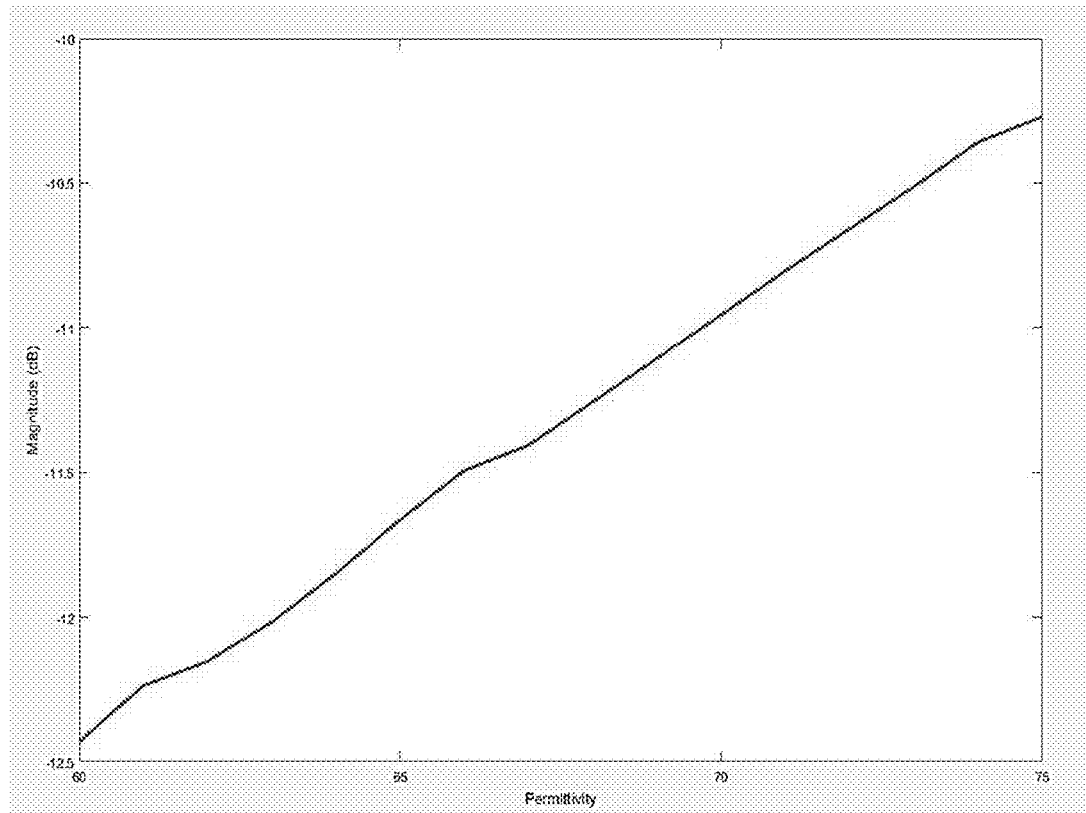
FIG. 19 is a graph showing the Relation between $S_{21}$ Magnitude and ε at 2 GHz, which shows the linear relation between the changes in permittivity and the corresponding shifts.
Figure 20:
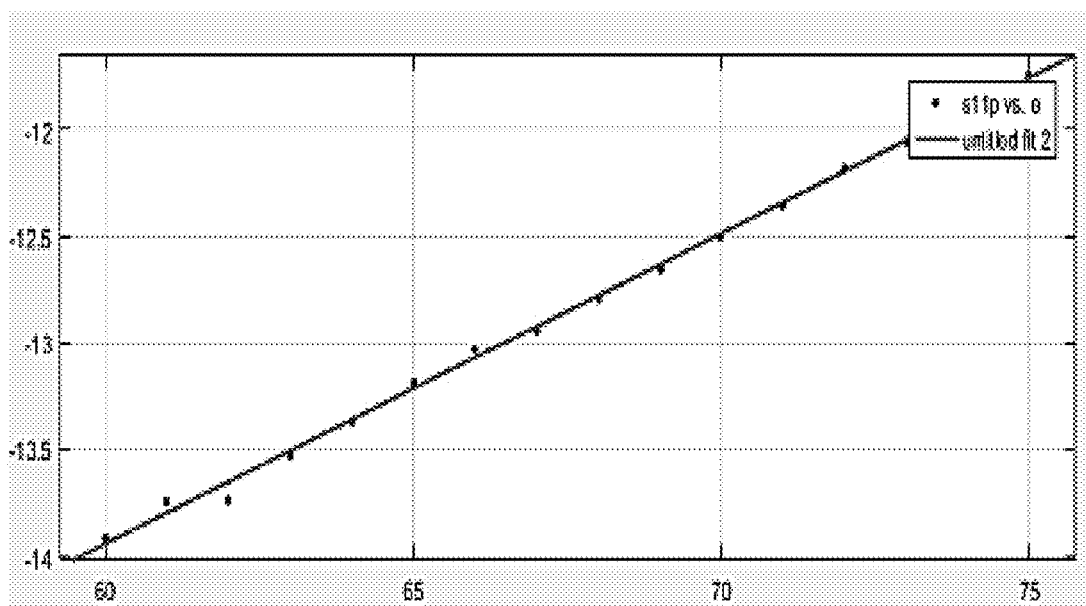
FIG. 20 is the Curve fitting of the sample points using Matlab from FIG. 19.

The Sensitivity test—$S_{21}$ Magnitude is shown in FIG. 17, which shows the change in the relative permittivity of blood (corresponding to varying the BGL). FIG. 18 is a Zoom in on one linear region in FIG. 17. The Relation between $S_{21}$ Magnitude and ε at 2 GHz is shown in FIG. 19, which shows the linear relation between the changes in permittivity and the corresponding shifts. FIG. 20 is the Curve fitting of the sample points using Matlab from FIG. 19.

Figure 21:
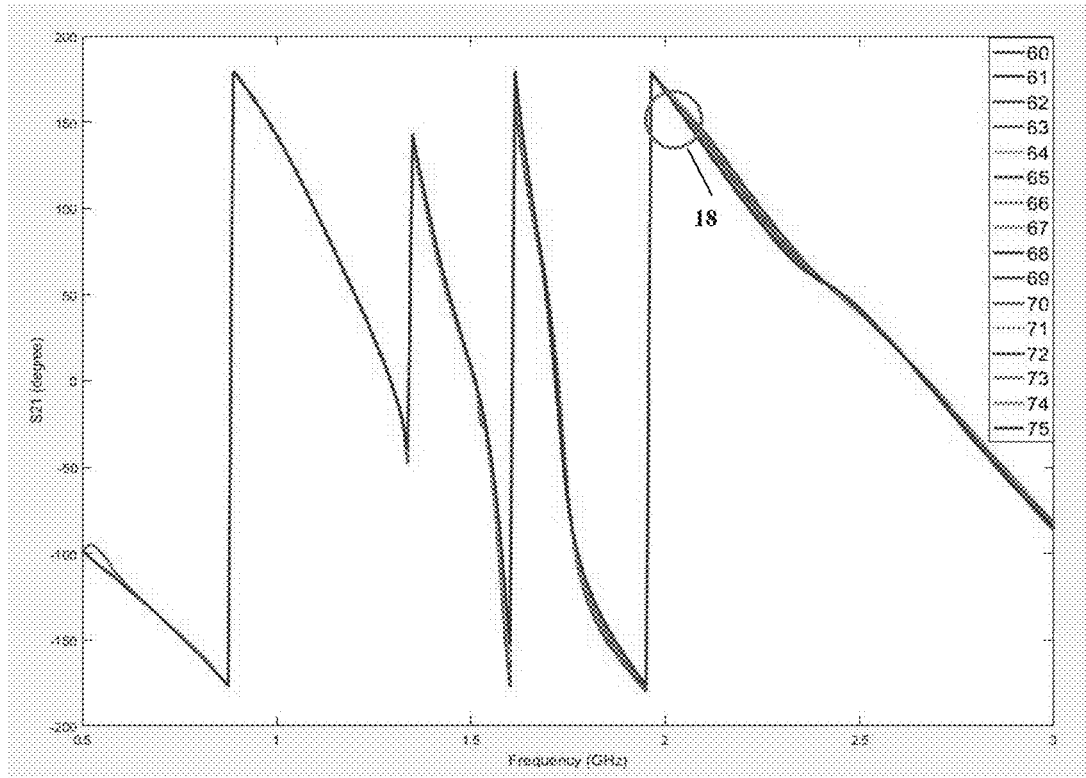
FIG. 21 is a graph showing the Sensitivity test for the $S_{21}$ Phase, which shows the change in the relative permittivity of blood (corresponding to varying the BGL).
Figure 22:
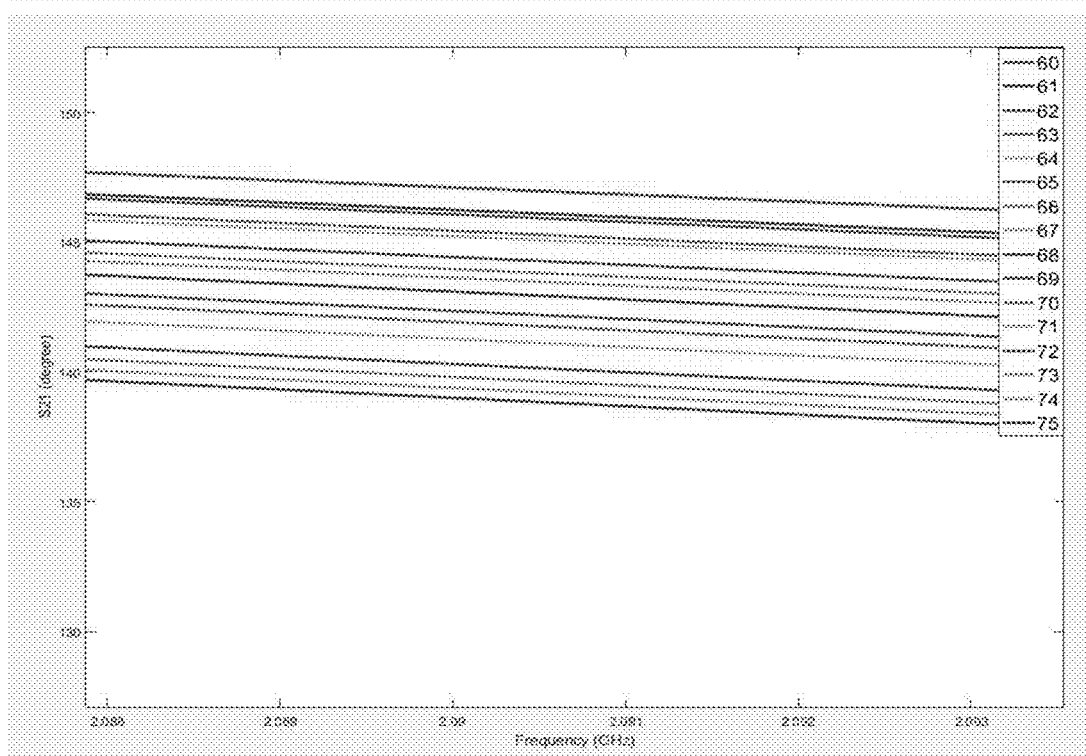
FIG. 22 is a graph showing one linear region from the circle 22 in FIG. 21.

Sensitivity test—$S_{21}$ Phase is shown in FIG. 21 shows the change in the relative permittivity of blood (corresponding to varying the BGL). FIG. 22 shows the Zoom in on one linear region from FIG. 21.

Figure 23:
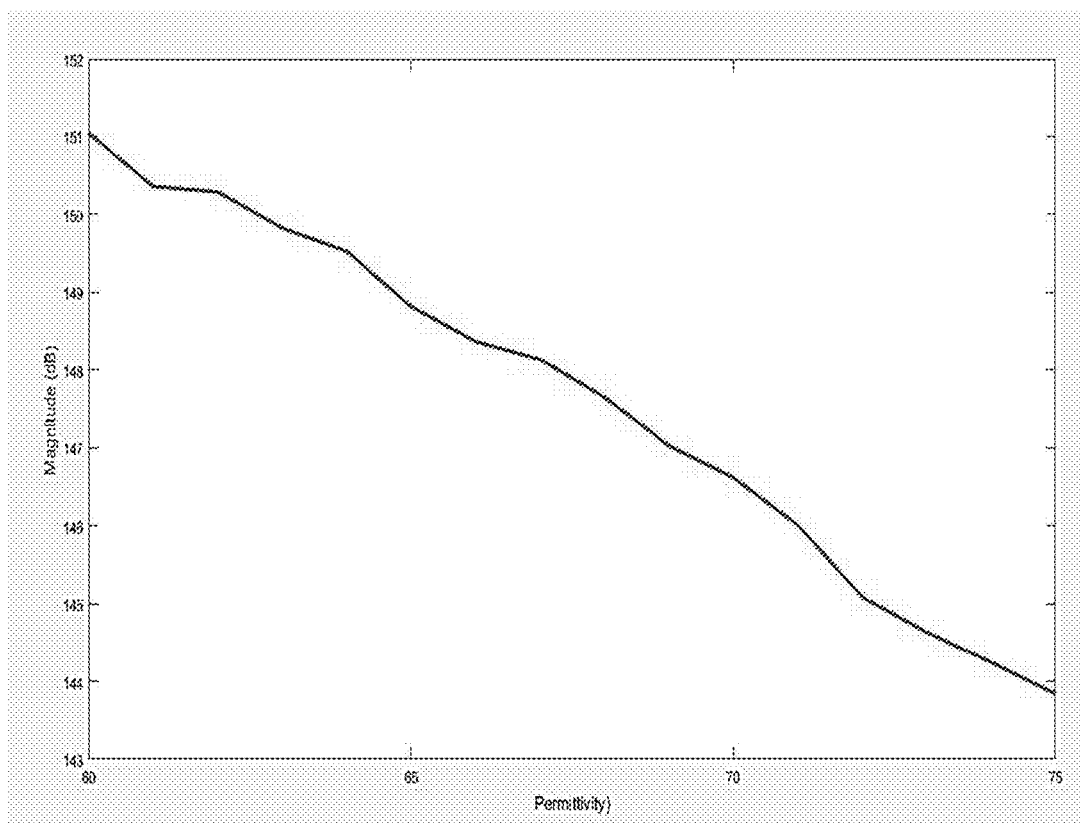
FIG. 23 is a graph showing the Relation between $S_{21}$ Phase and ε at 2.09 GHz, which shows the linear relation between the changes in permittivity and the corresponding shifts.
Figure 24:
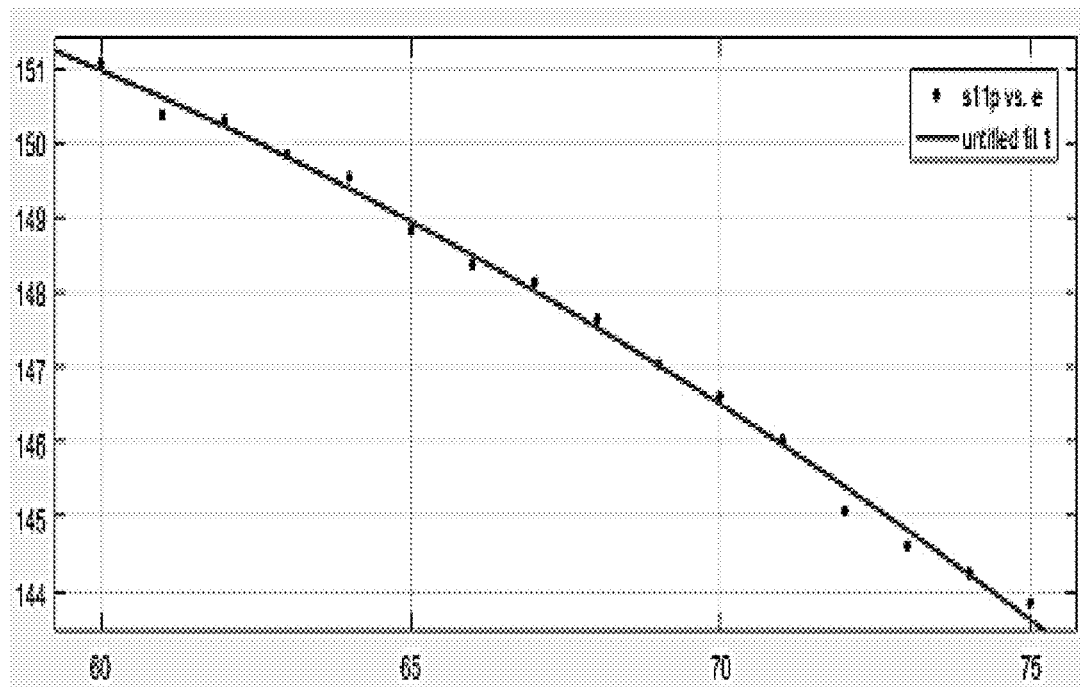
FIG. 24 is a graph showing the Curve fitting of the sample points using Matlab.

The Relation between $S_{21}$ Phase and ε at 2.09 GHz is shown in FIG. 23, which shows the linear relation between the changes in permittivity and the corresponding shifts. FIG. 24 shows the Curve fitting of the sample points using Matlab.

Fabrication—Rigid Antenna

Figures 25A, 25B:
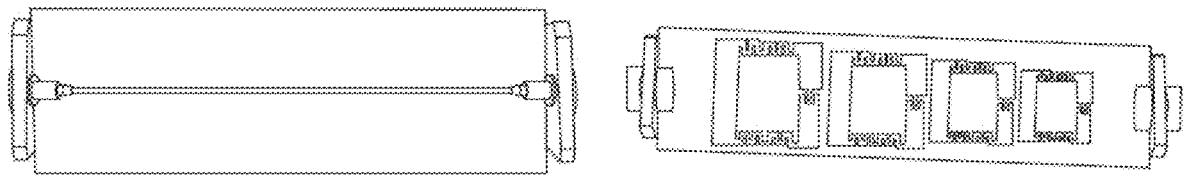
FIGS. 25A-25B are top views of the top layer and bottom layer fabricated on a 1.27 mm-thick Rogers 3006 substrate.
Figure 26A:
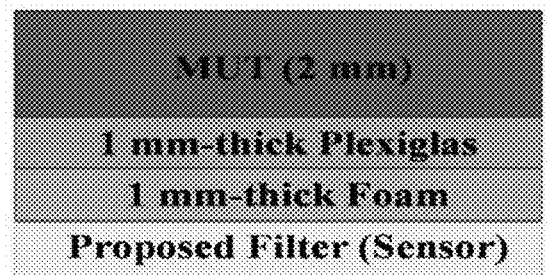
FIG. 26A is side view of a schematic diagram of a multi-layer system.
Figure 26B:
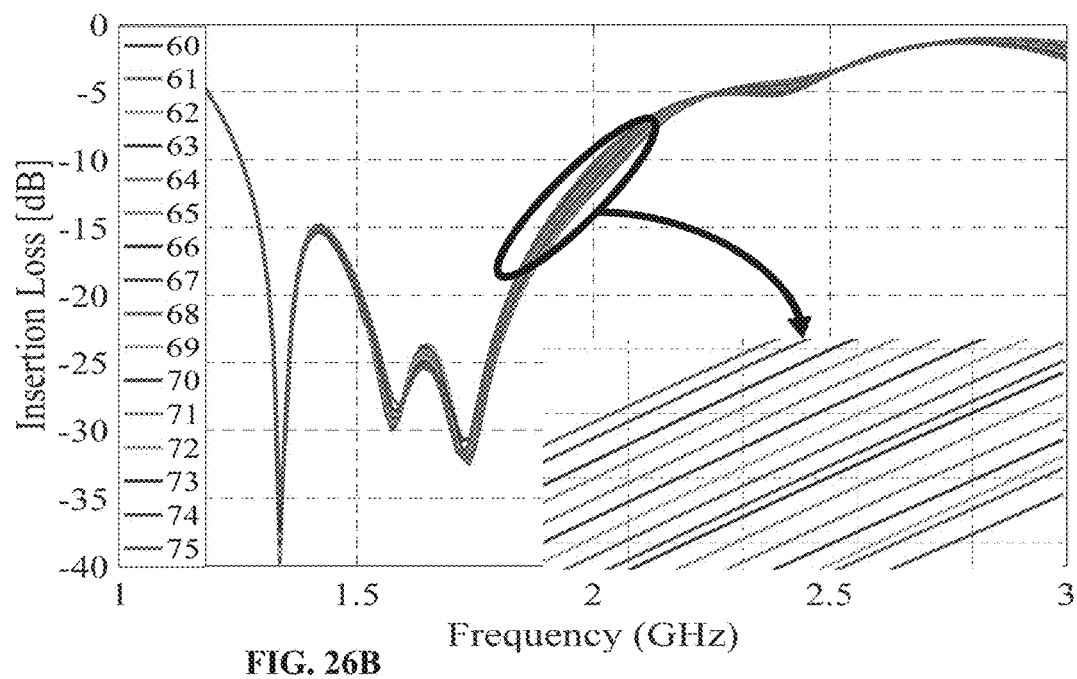
FIG. 26B is a graph of the insertion loss of the biomarker filter, where a clear broadband reject response is obvious in the 1.25-2.25 GHz frequency range.

To validate the performance of the proposed filter in carrying out dielectric constant characterization processes, a prototype is fabricated on a 1.27 mm-thick Rogers 3006 substrate as shown in FIGS. 25A-25B. A good agreement between the simulated and measured S-parameters of the fabricated filter is attained. The filter is then loaded by a multi-layer system as depicted in FIG. 26A. In addition, the dielectric constant of the MUT is swept from 60 to 75 to reflect some realistic dielectric values that relate to human organs or blood. The insertion loss of the proposed filter is shown in FIG. 26B, where a clear broadband reject response is obvious in the 1.25-2.25 GHz frequency range. Such performance is advantageous for the application of this filter in a sensor platform. This is due to the fact that its sensitivity can be sampled across a broad bandwidth in comparison to narrowband filters.

Figure 27A:
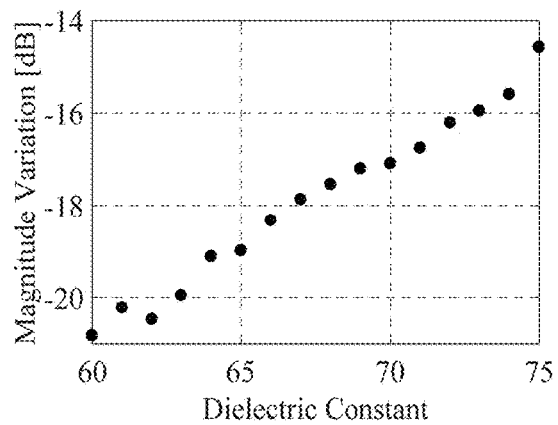
FIGS. 27A-27B are graphs of the magnitude and phase of the filters' reflection coefficient as a function of the corresponding values of dielectric constants at f=2.25 GHz.
Figure 27B:
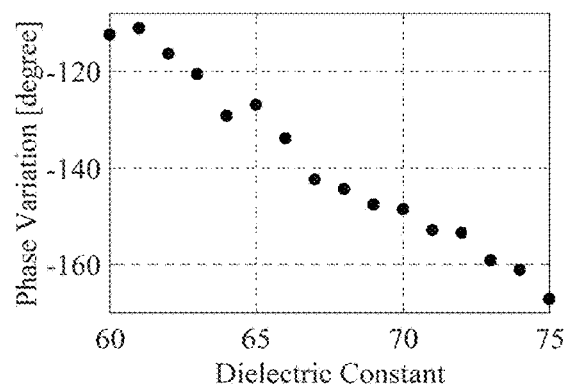

Furthermore, the magnitude and phase of the filters' reflection coefficient as a function of the corresponding values of dielectric constants at f=2.25 GHz are shown in FIGS. 27A-27B. Acting as a sensor, the filter is able to differentiate the variation of dielectric constant values. Its response exhibits a clear correlation with the material's dielectric constant as illustrated in FIG. 27a-27B at f=2.25 GHz. This is achieved with an average sensitivity of 0.42 dB/ε_(r) and 3.65°/ε_r at f=2.25 GHz. Similar values are recorded across the broad bandwidth.

Figure 27C:
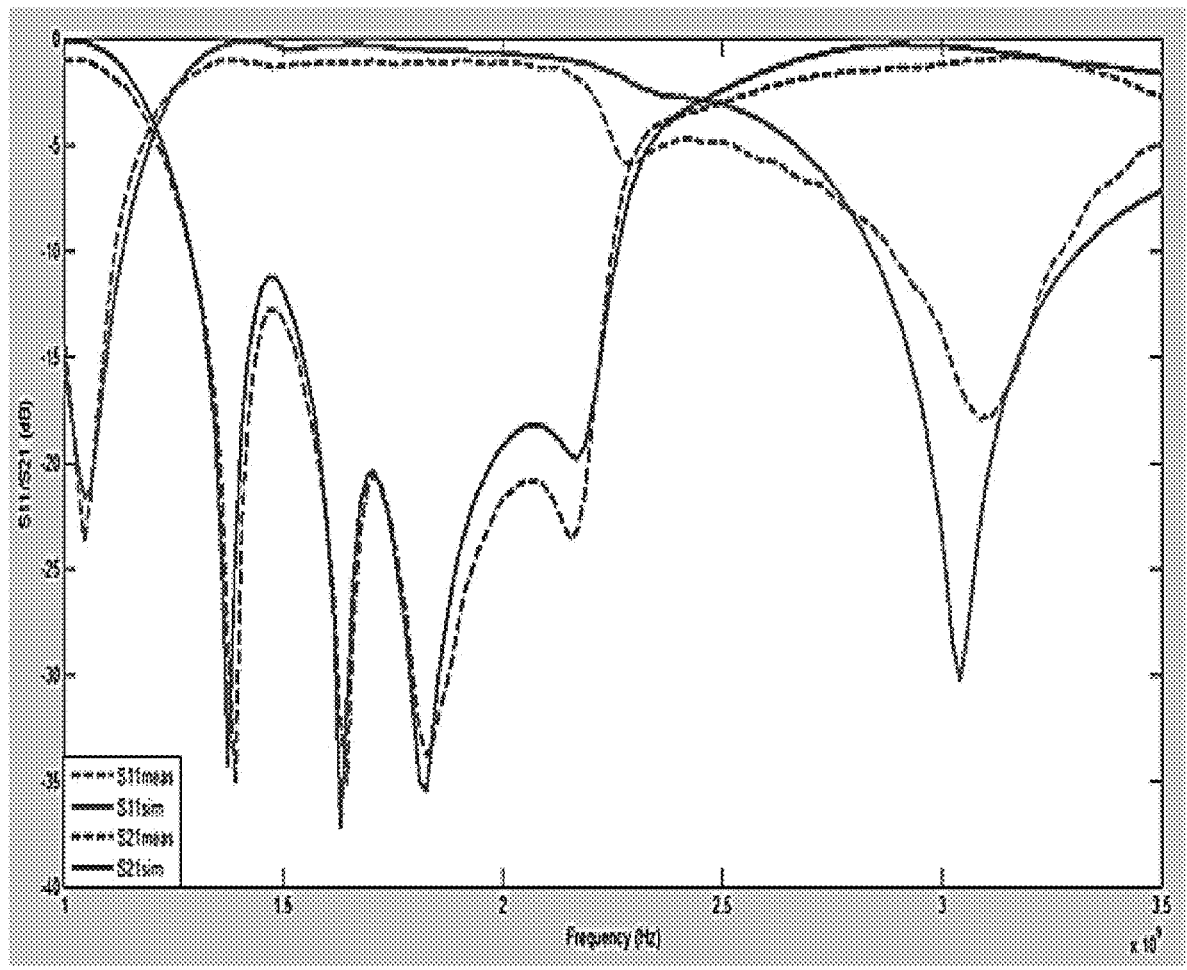
FIG. 27C is a graph showing the Measured and simulated results.

FIG. 27C shows the Measured and simulated results.

Sensitivity Test—Simulations Flexible Filter

Figure 28:
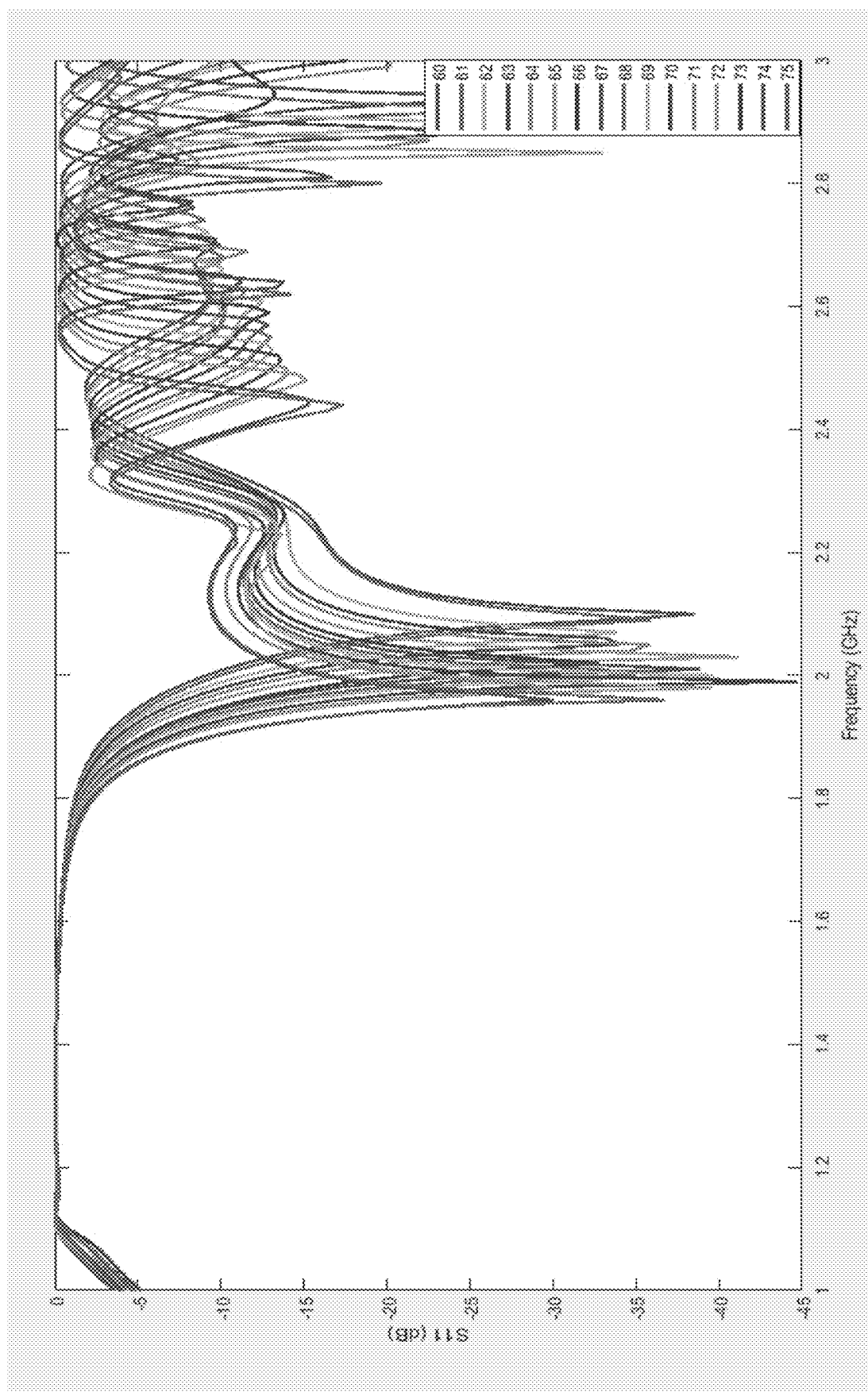
FIG. 28 is a graph showing the Example Sensitivity test—$S_{11}$ Magnitude.
Figure 29:
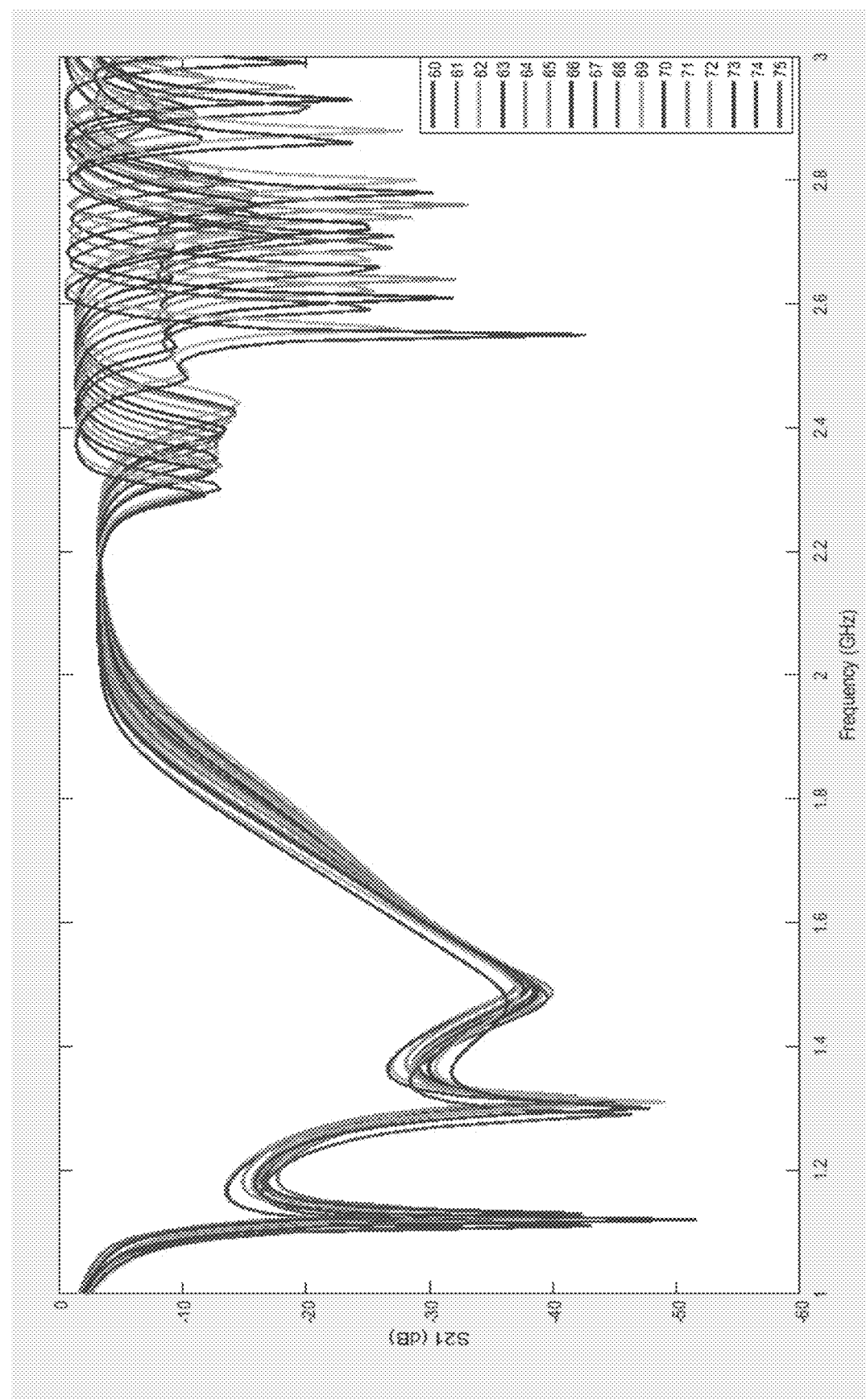
FIG. 29 is a graph showing the Example Sensitivity test—$S_{21}$ Magnitude.
Figure 30:
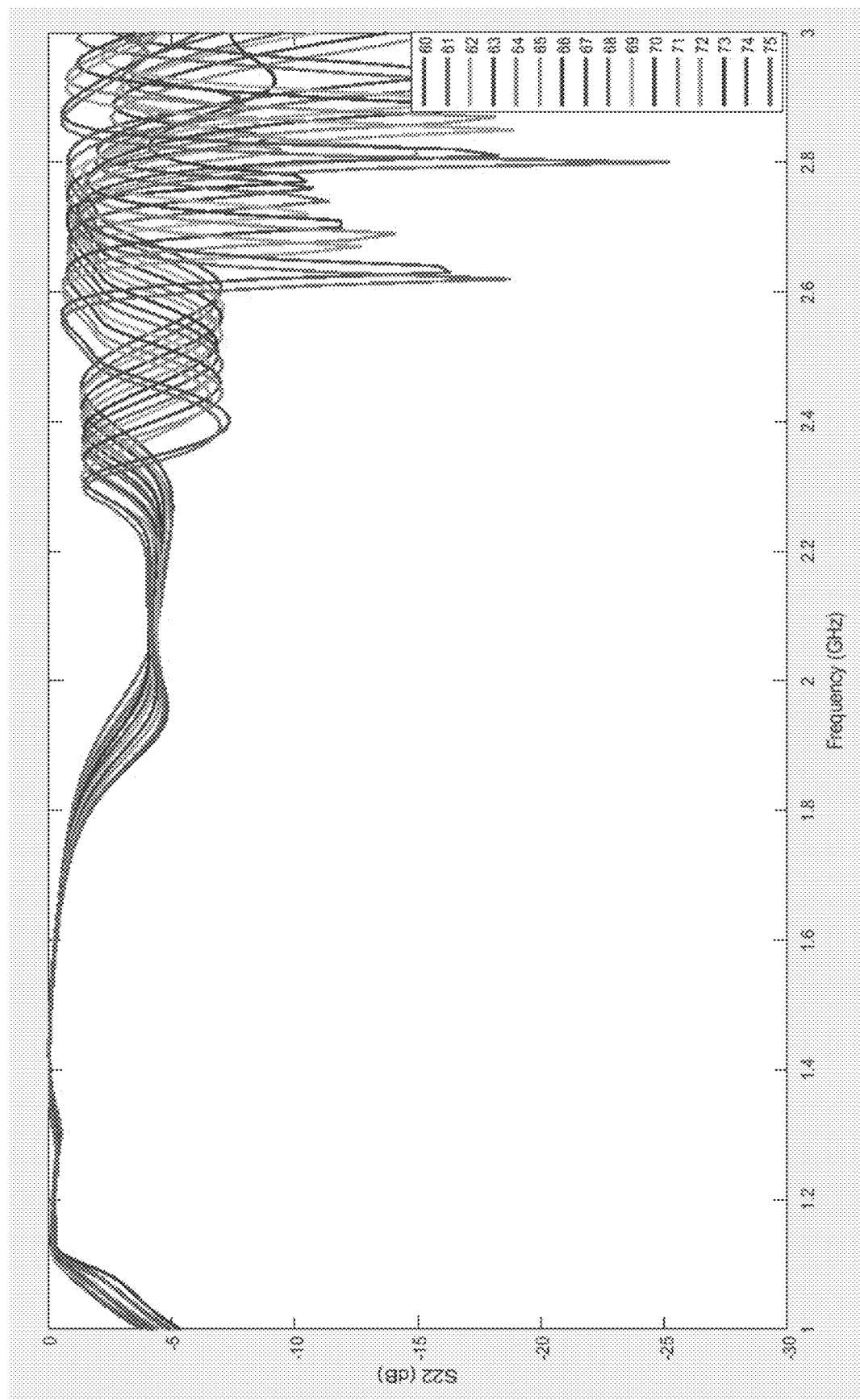
FIG. 30 is a graph showing the Example Sensitivity test—$S_{22}$ Magnitude.
Figure 31:
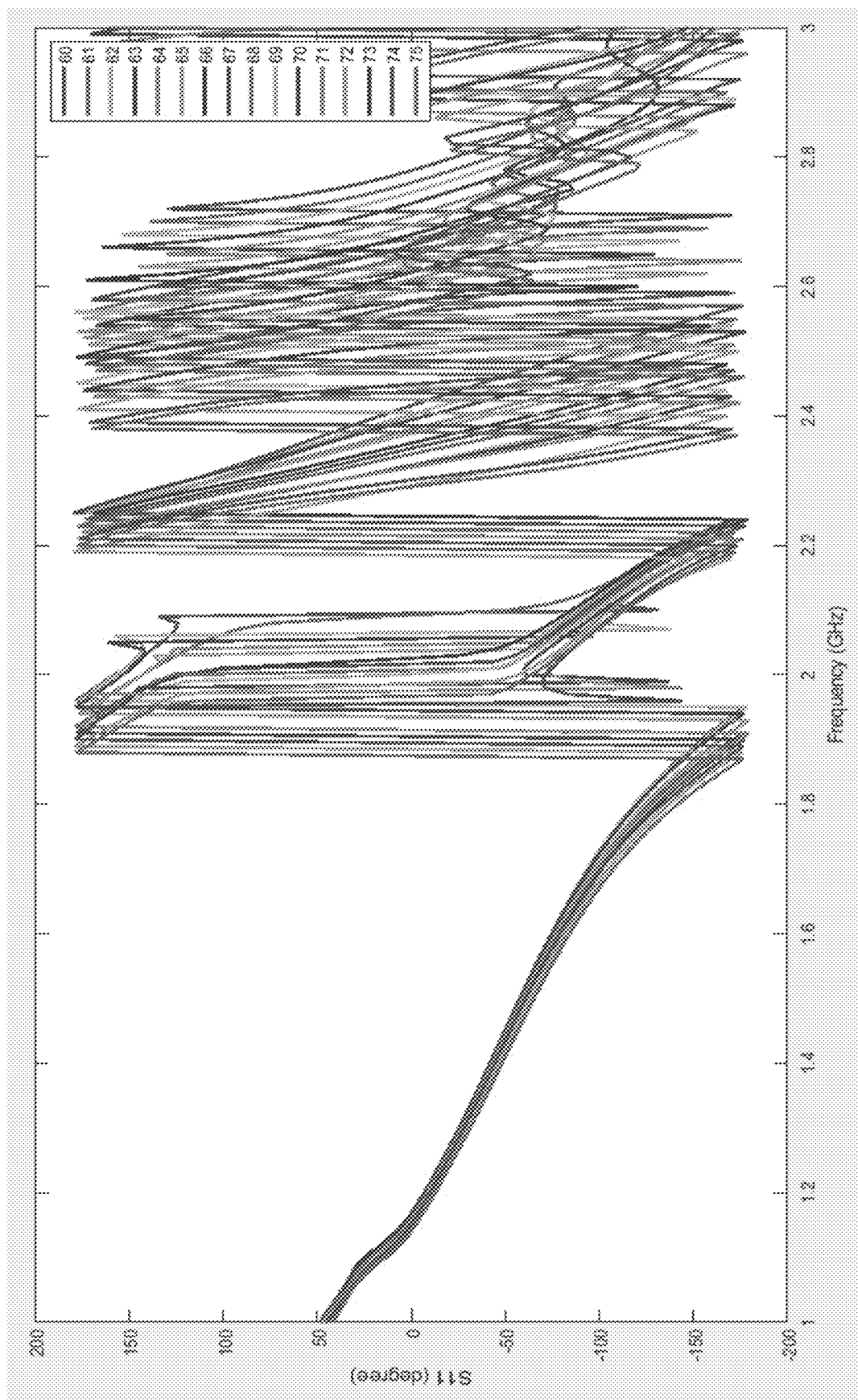
FIG. 31 is a graph showing the Sensitivity test—$S_{11}$ Phase.
Figure 32:
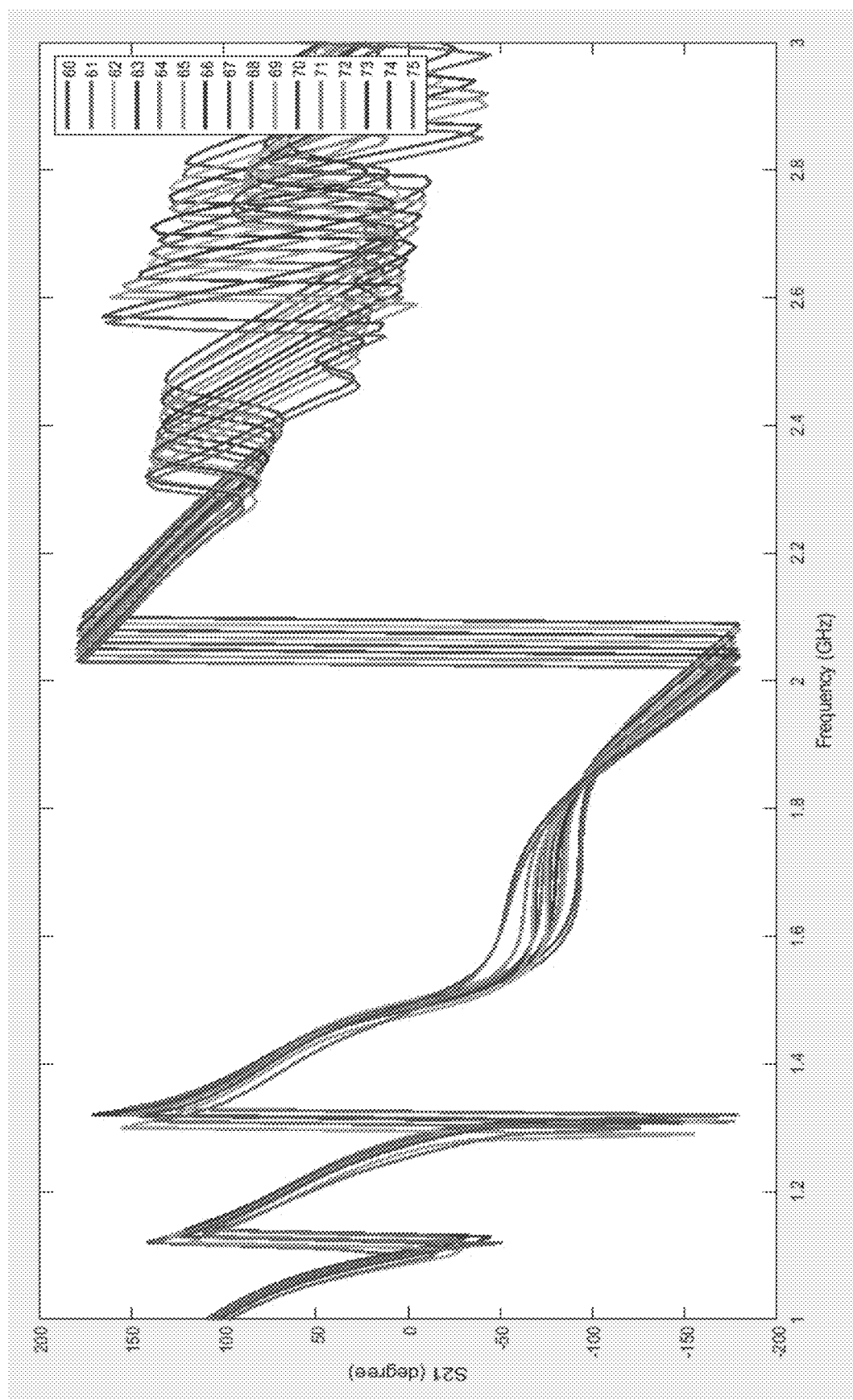
FIG. 32 is a graph showing the Sensitivity test—$S_{21}$ Phase.
Figure 33:
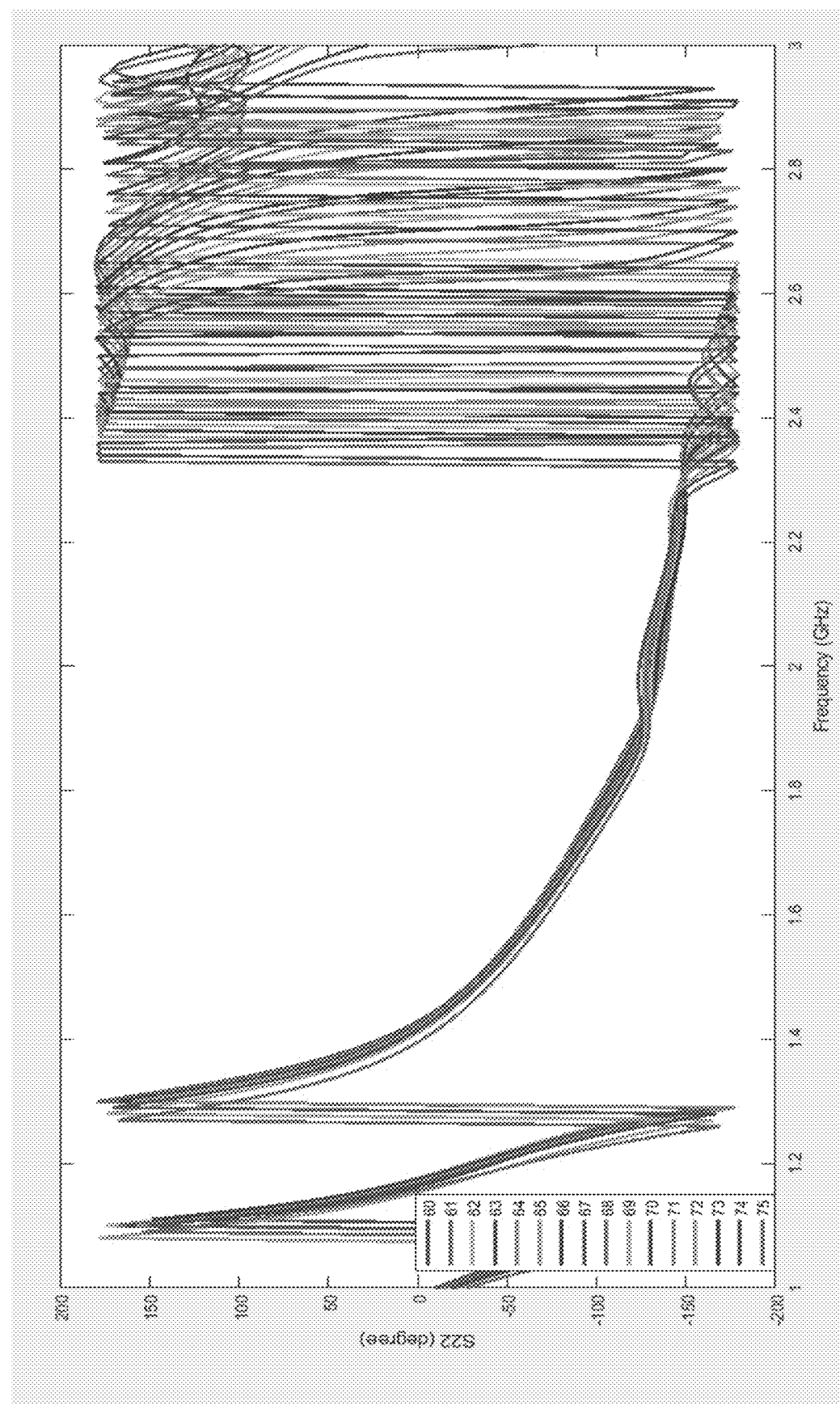
FIG. 33 is a graph showing the Sensitivity test—$S_{22}$ Phase
Figure 34A:
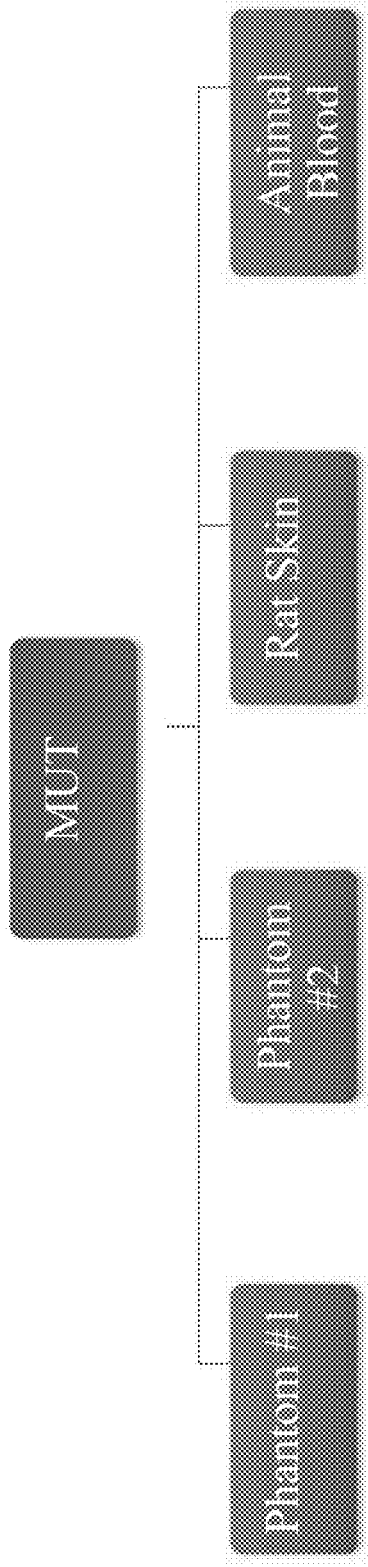
FIG. 34A is a schematic diagram showing the process to take the measurements of the rigid filter.
Figure 34B:
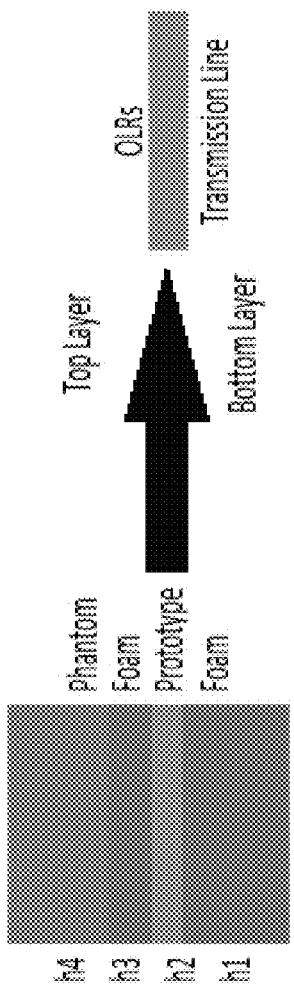
FIG. 34B is a schematic diagram showing the testing prototype setup.

Blood layer of thickness h=4 mm placed 2 mm beneath the filter, as shown previously in FIG. 10. Variations in the permittivity of blood is between 60<ε<75. Record S-parameters phase and magnitude. Example Sensitivity test—$S_{11}$ Magnitude is shown in FIG. 28. Example Sensitivity test—$S_{21}$ Magnitude is shown in FIG. 29. Example Sensitivity test—$S_{22}$ Magnitude is shown in FIG. 30. Sensitivity test—$S_{11}$ Phase is shown in FIG. 31. Sensitivity test—$S_{21}$ Phase is shown in FIG. 32. Sensitivity test—$S_{22}$ Phase is shown in FIG. 33. Measurements-Rigid Filter flow chart is shown in FIG. 34A-34B.

TABLE 3

| Parameter | Thickness (mm) |
| --- | --- |
| h4 | MUT dependent |
| h3 | 3 |
| h2 | 1.27 |
| h1 | 1.3 |

Figure 35:
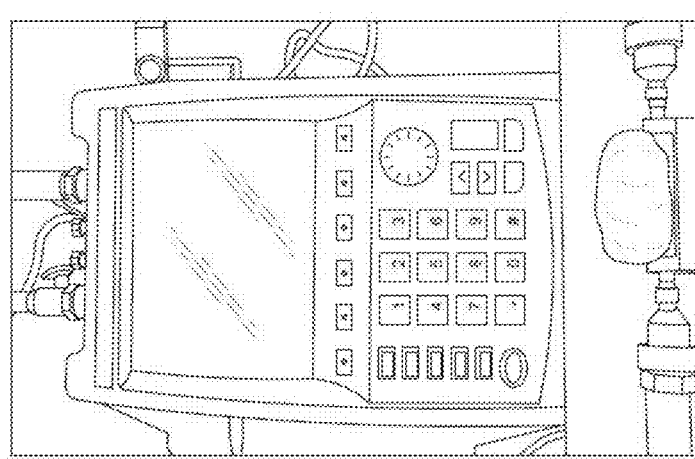
FIG. 35 is a graph showing the Measurements on Phantoms #1.
Figure 36:
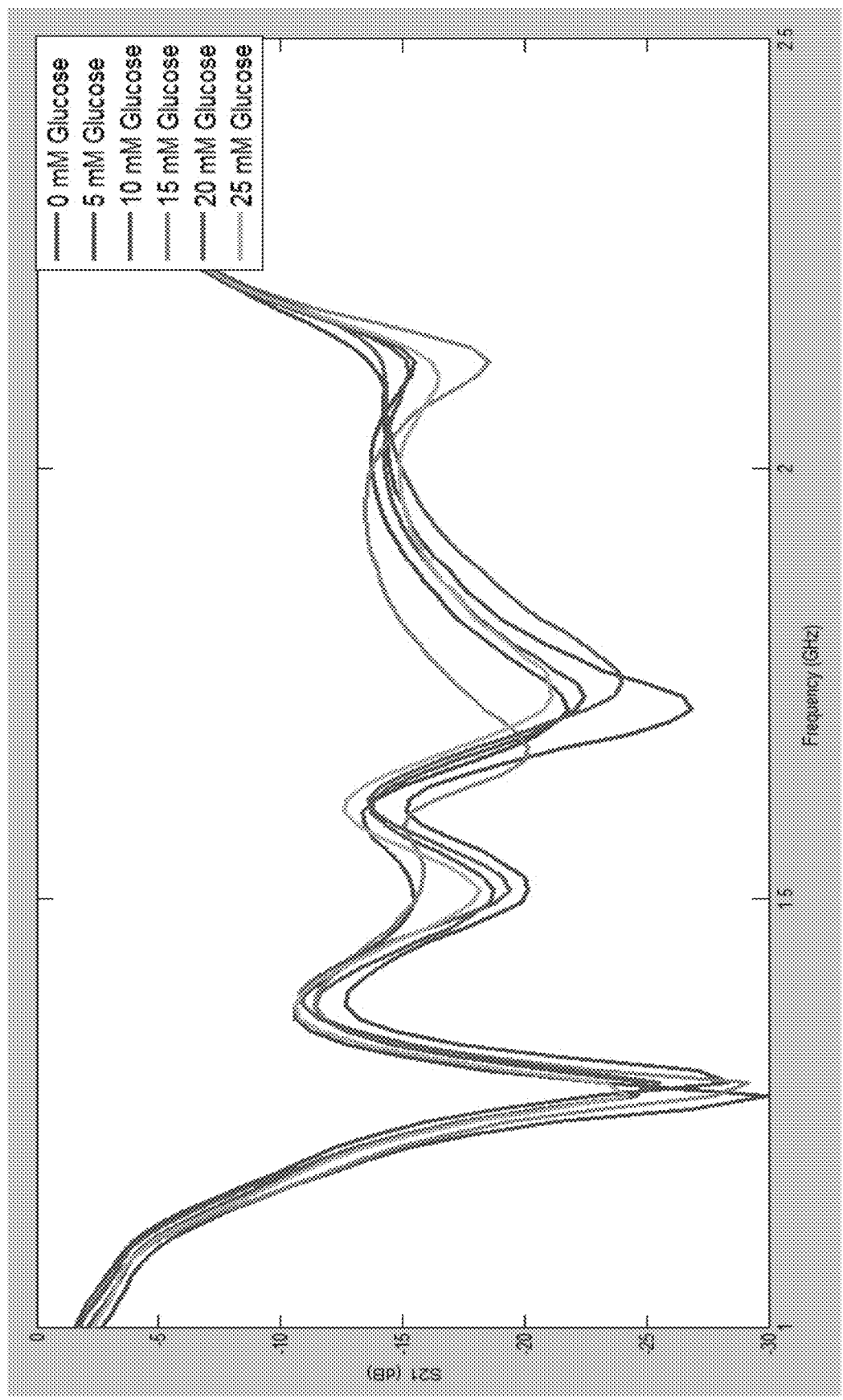
FIG. 36 is a graph showing the Measurements on Phantoms #1 for $S_{21}$ Magnitude—Rigid Filter and the Results for first set of phantoms.
Figure 37:
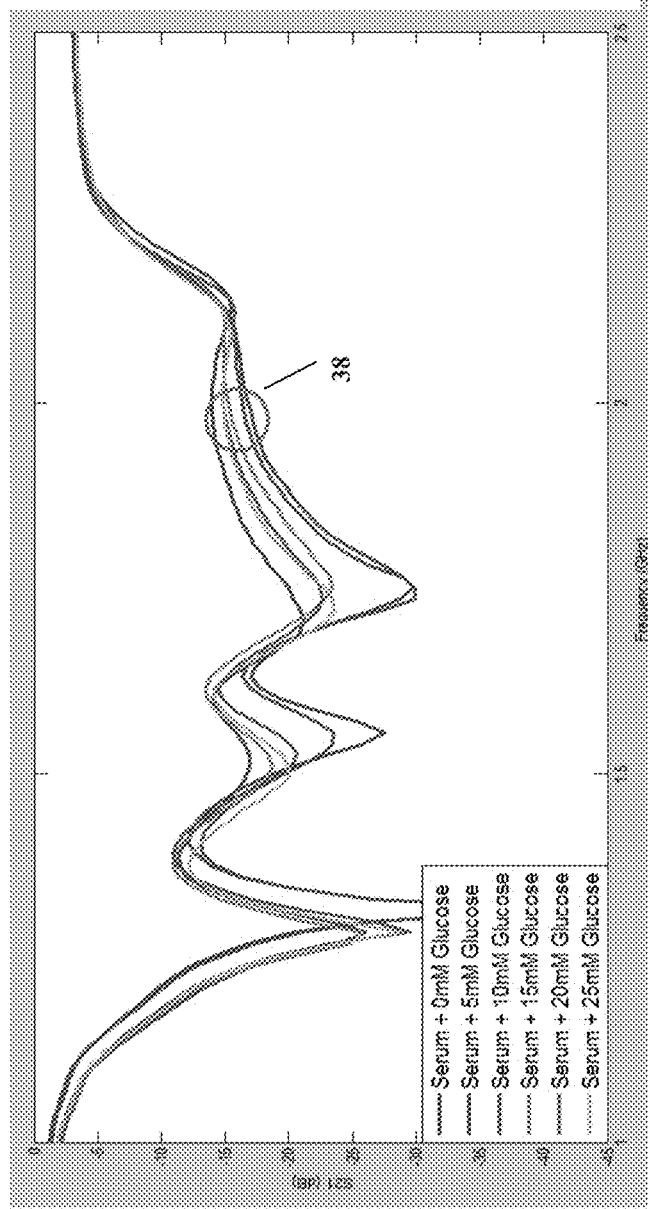
FIG. 37 is a graph showing the Measurements on Phantoms #1—$S_{21}$ Magnitude—Rigid Filter and the results for second set of phantoms (with serum).
Figure 38:
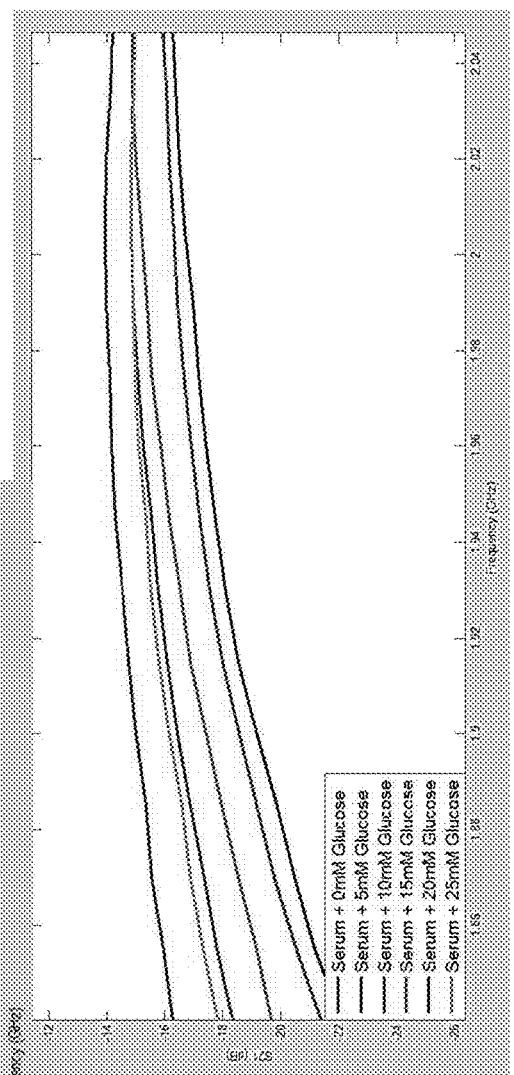
FIG. 38 is a graph showing the zoomed image from circle 38 in FIG. 37.
Figure 39:
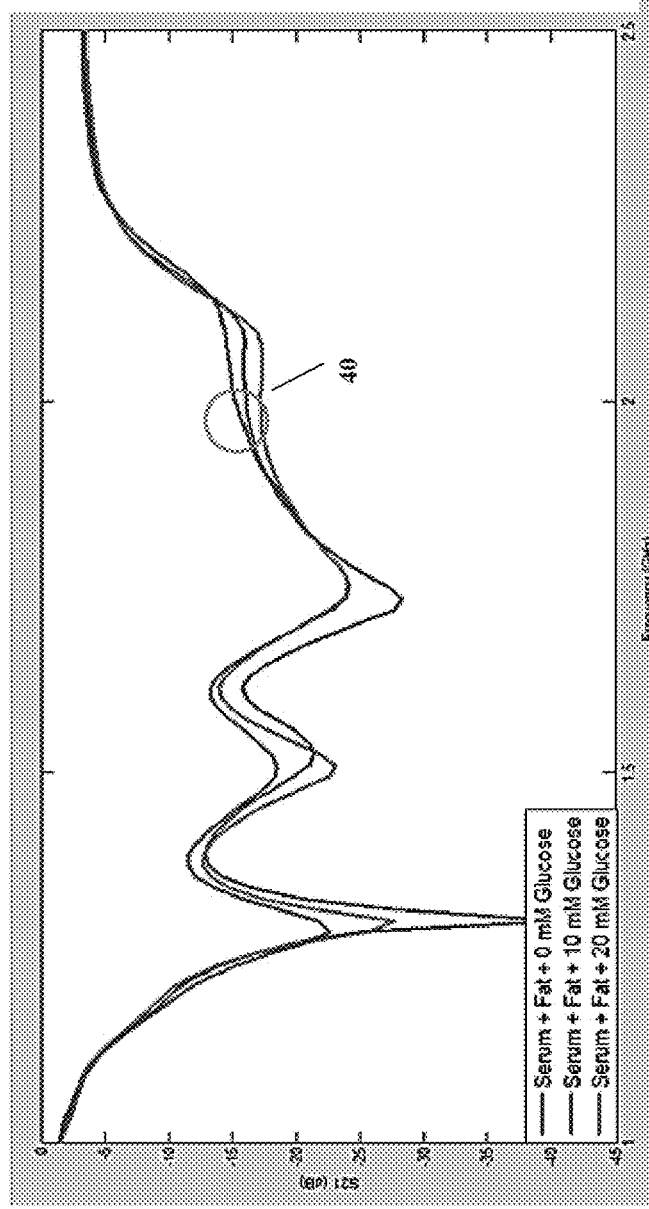
FIG. 39 is a graph showing the Measurements on Phantoms #1—$S_{21}$ Magnitude—Rigid Filter and the results for third set of phantoms (with serum and fat).
Figure 40:
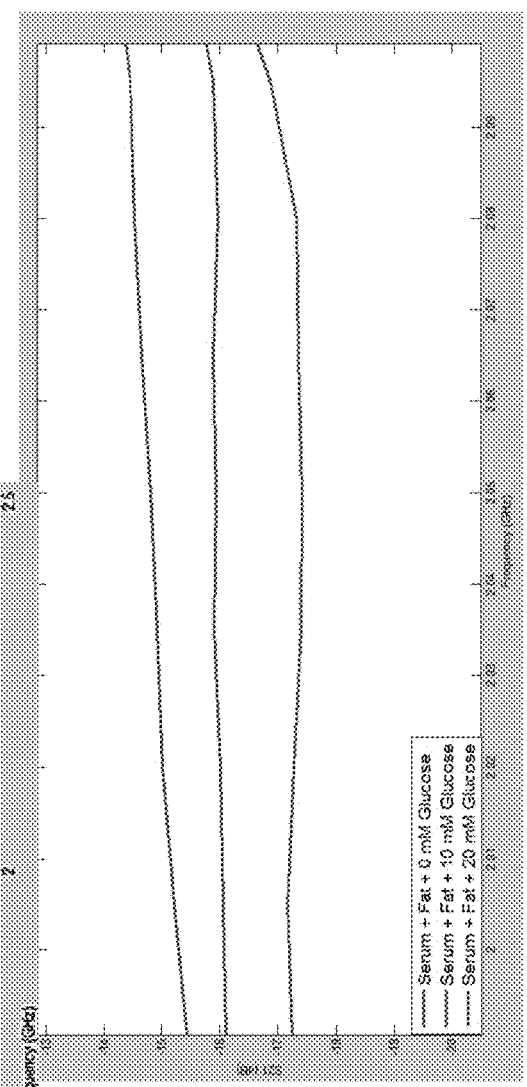
FIG. 40 is a graph showing the zoomed image from circle 40 in FIG. 39.
Figure 41:
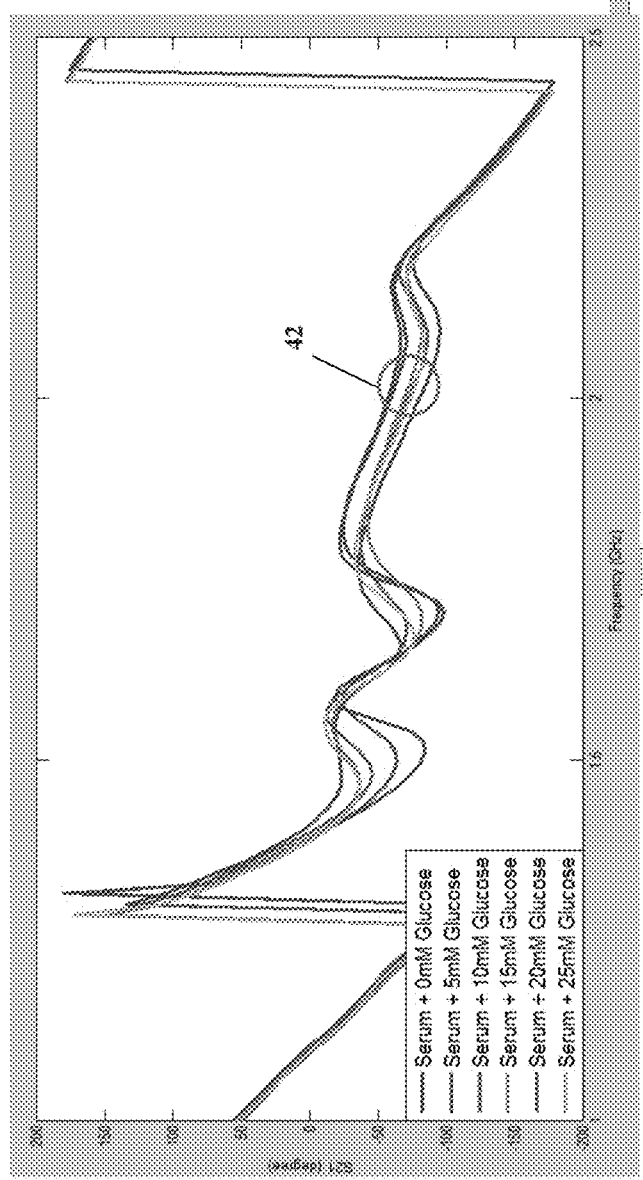
FIG. 41 is a graph showing the Measurements on Phantoms #1—$S_{21}$ Phase—Rigid Filter and the results for second set of phantoms (with serum).
Figure 42:
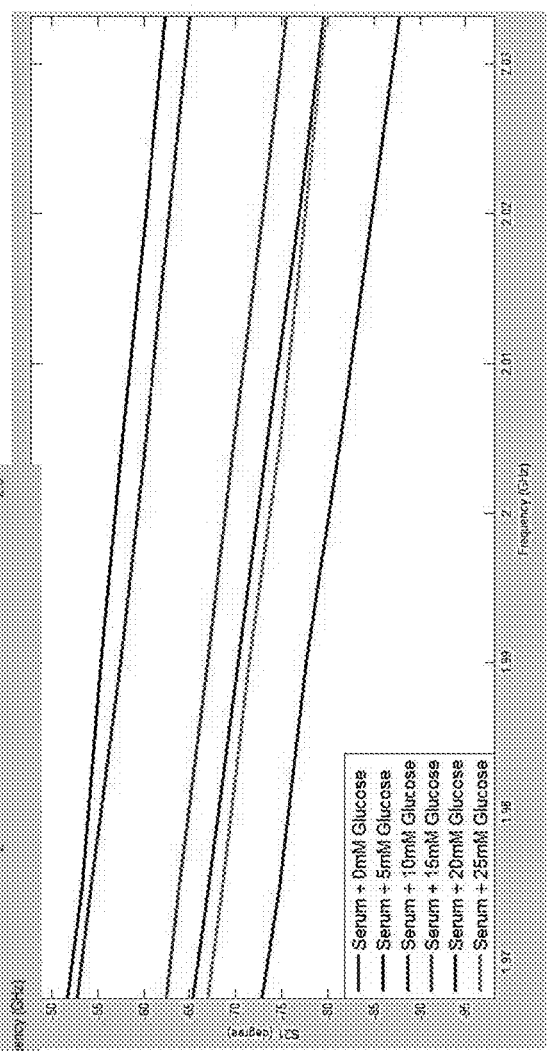
FIG. 42 is a graph showing the zoomed image from circle 42 in FIG. 41.
Figure 43:
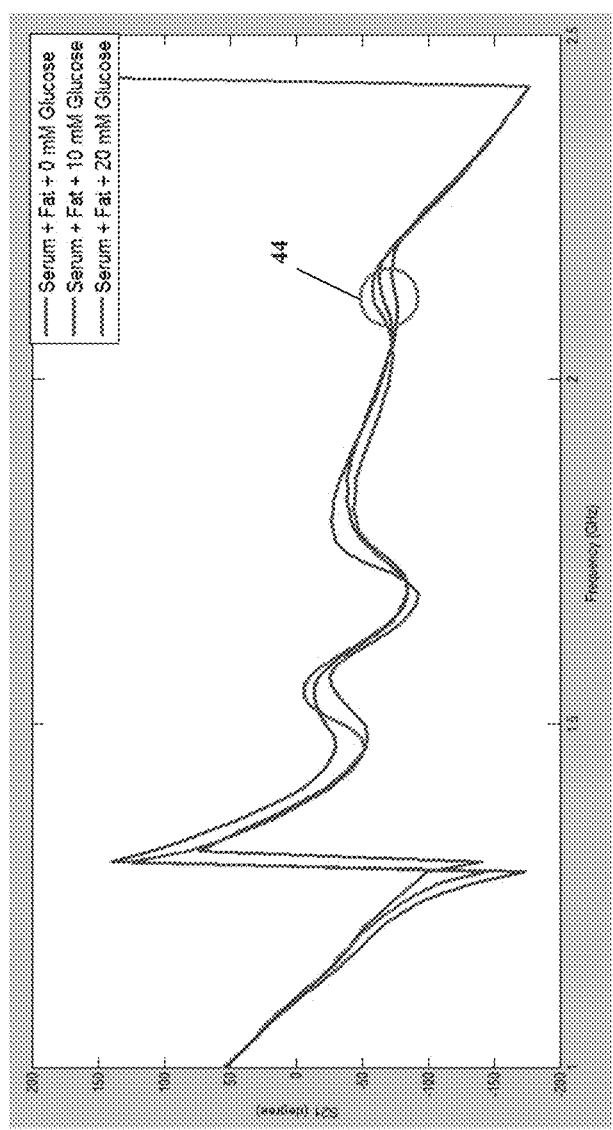
FIG. 43 is a graph showing the Measurements on Phantoms #1—$S_{21}$ Phase—Rigid Filter and results for third set of phantoms (with serum and fat).
Figure 44:
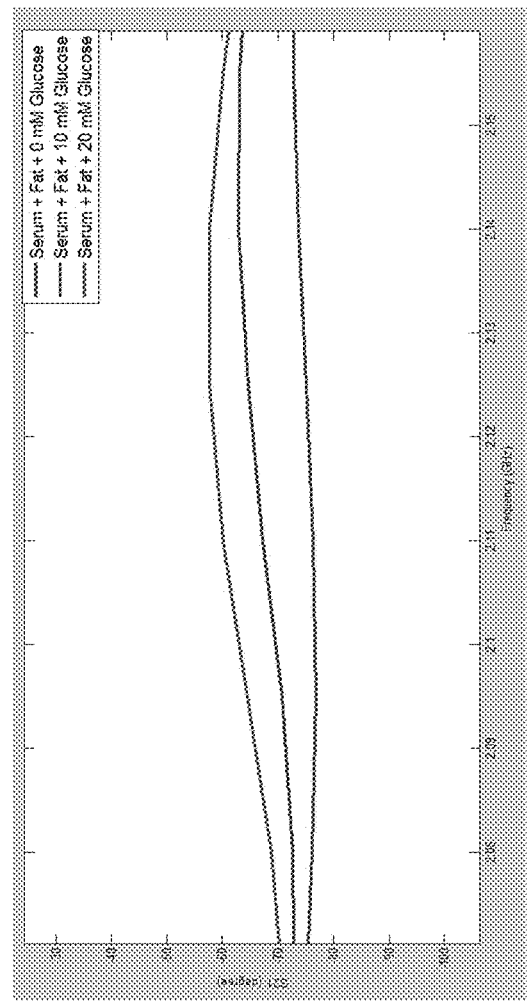
FIG. 44 is a graph showing the zoomed image from circle 44 in FIG. 43.

Measurements on Phantoms #1 is shown in FIG. 35. Solutions Composition is NaCl, Flour, Serum, Oil, Glucose in concentrations of 0 mM, 5 mM, 10 mM, 15 mM, 20 mM, and 25 mM. Measurements on Phantoms #1—$S_{21}$ Magnitude—Rigid Filter and the Results for first set of phantoms is shown in FIG. 36. Measurements on Phantoms #1—$S_{21}$ Magnitude—Rigid Filter and the results for second set of phantoms (with serum) is shown in FIG. 37, and the zoomed image in FIG. 38. Measurements on Phantoms #1—$S_{21}$ Magnitude—Rigid Filter and the results for third set of phantoms (with serum and fat) are shown in FIG. 39 and the zoomed image in FIG. 40. Measurements on Phantoms #1—$S_{21}$ Phase—Rigid Filter and the results for second set of phantoms (with serum) is shown in FIG. 41 and zoomed image in FIG. 42. Measurements on Phantoms #1—$S_{21}$ Phase—Rigid Filter and results for third set of phantoms (with serum and fat) is shown in FIG. 43 and the zoomed image in FIG. 44.

Figure 46:
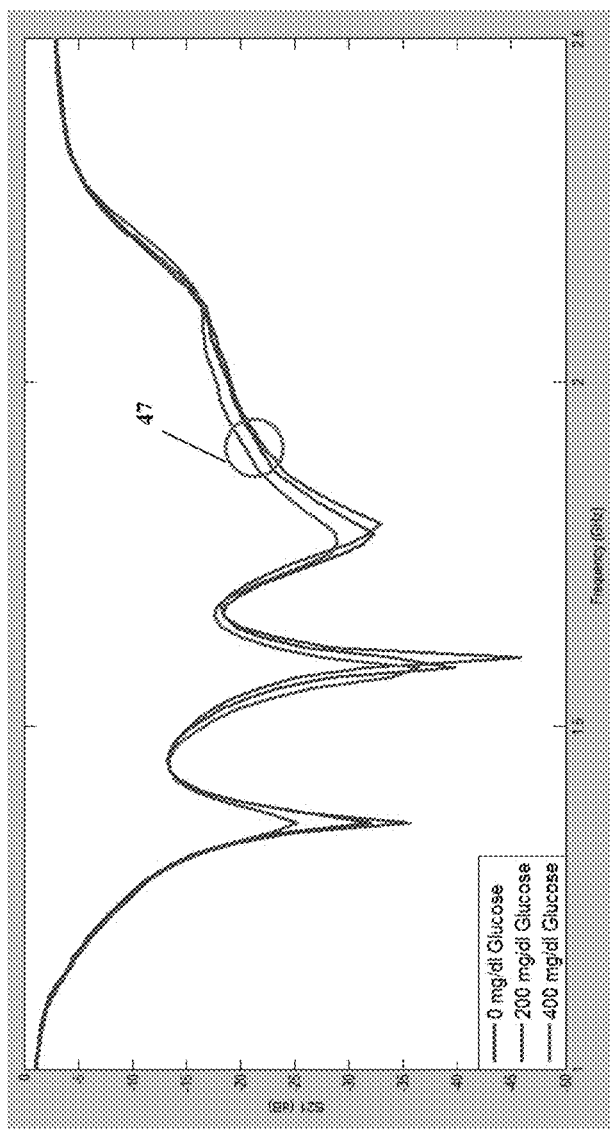
FIG. 46 is a graph showing the Measurements on Phantoms #2—$S_{21}$ Magnitude—Rigid Filter and Results for phantoms #2.
Figure 47:
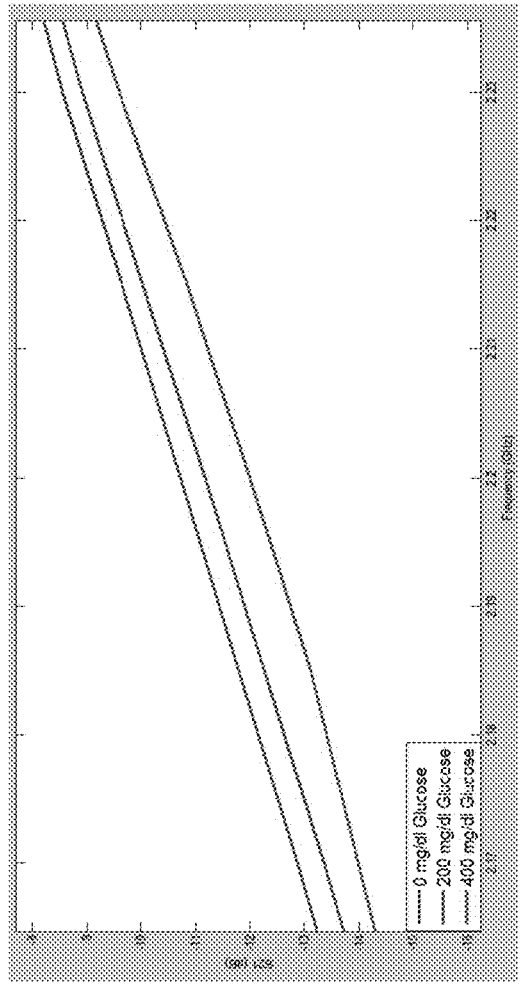
FIG. 47 is a graph showing the zoomed image of circle 47 in FIG. 46.
Figure 45:
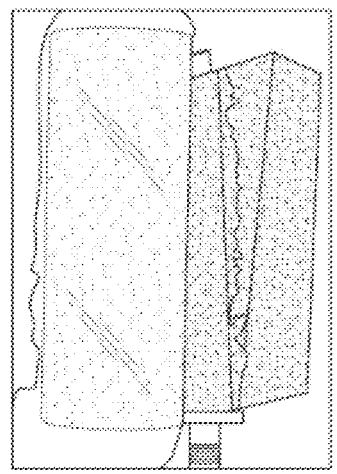
FIG. 45 is a photo for the Measurements on Phantoms #2 included Solutions Composition of Serum, Gelatin, Oil, NaCl, Detergent.

Measurements on Phantoms #2 included Solutions Composition of Serum, Gelatin, Oil, NaCl, Detergent as shown in FIG. 45. And Glucose concentrations of 0 mg/dl, 200 mg/dl, and 400 mg/dl. Measurements on Phantoms #2—$S_{21}$ Magnitude—Rigid. Filter and Results for phantoms #2 is shown in FIG. 46 and the zoomed image is shown in FIG. 47.

Figure 48B:
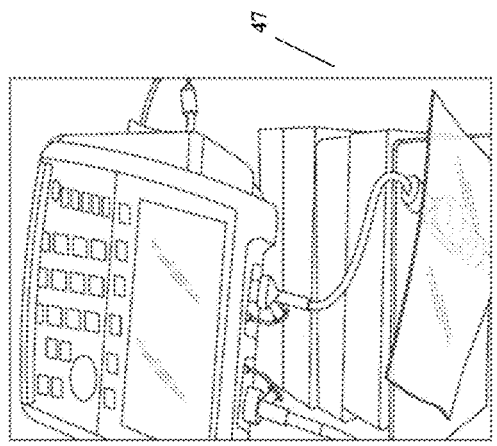
FIGS. 48A-48B are photos for the design for the Measurements on Rat Skin.
Figure 48A:
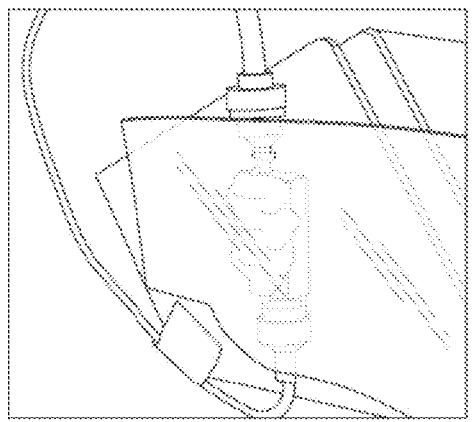
Figure 49:
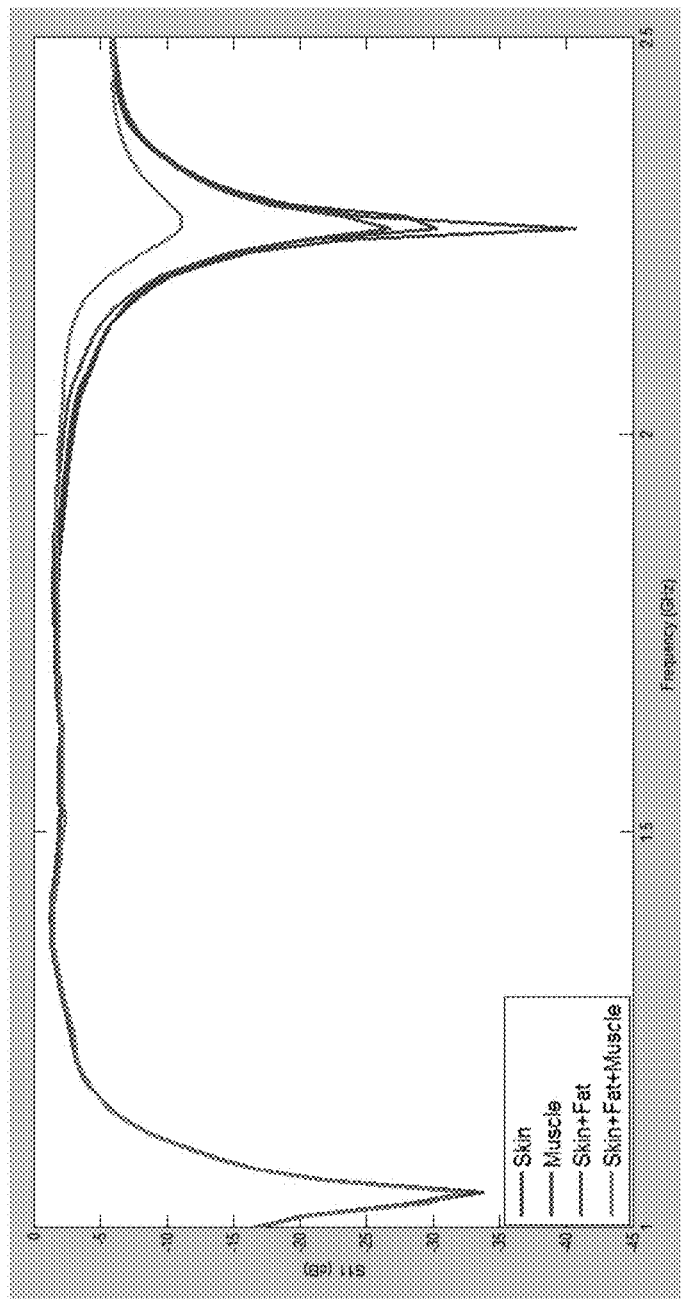
FIG. 49 is a graph showing the Measurements on Rat Skin—$S_{11}$ Magnitude—Rigid Filter and the Effect of layers on sensor.

Measurements on Rat Skin are shown in FIGS. 48A-48B. The steps proceeded as follows: Anesthetized rat dissected; Skin, fat and muscle placed on sensor; Various glucose concentrations injected; S-parameters recorded. Measurements on Rat Skin—$S_{11}$ Magnitude—Rigid Filter and the Effect of layers on sensor is shown in FIG. 49.

Figure 50:
FIG. 50 is a graph showing the Measurements on Rat Skin—$S_{21}$ Magnitude—Rigid Filter and the Results of measurements on real skin.
Figure 51:
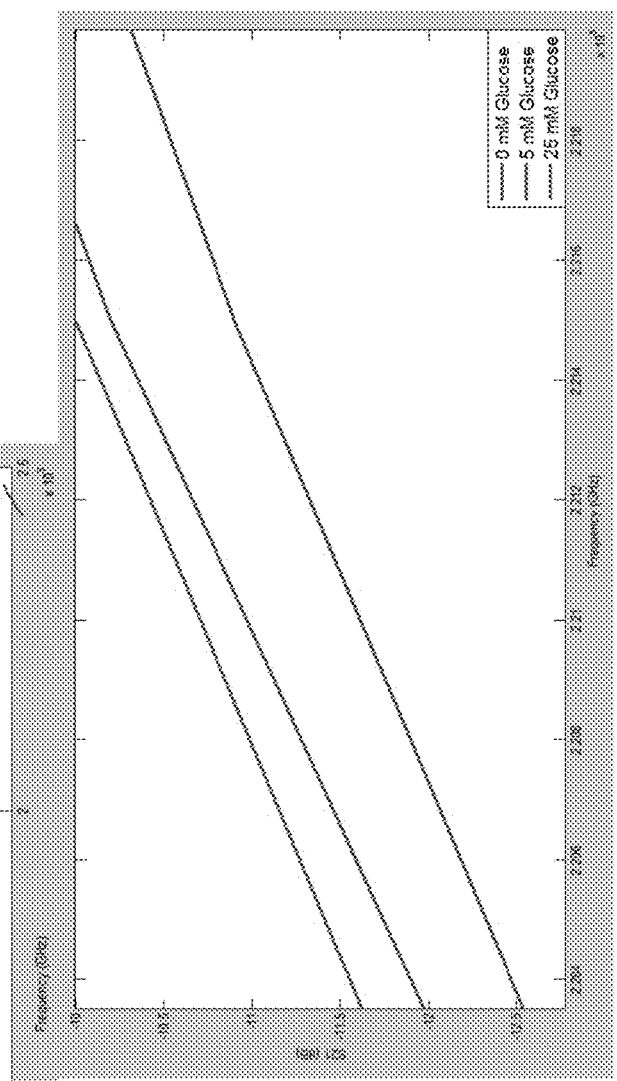
FIG. 51 is a graph showing the zoomed image of circle 51 in FIG. 50.
Figure 52A:
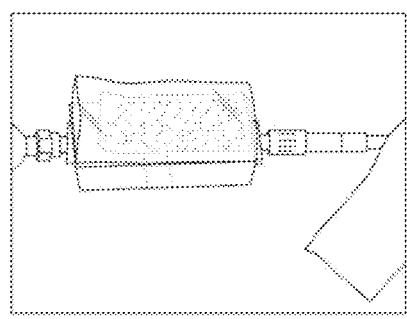
FIGS. 52A-52B are photos showing the setup for the Measurements on Blood.
Figure 52B:
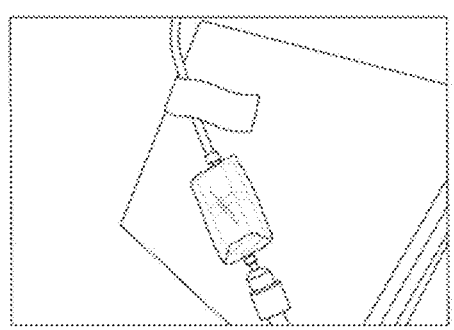

Measurements on Rat Skin—$S_{21}$ Magnitude—Rigid Filter and the Results of measurements on real skin is shown FIG. 50 and zoomed image in FIG. 51. Measurements on Blood is shown in FIGS. 52A-52B. The steps proceeded as follows: Draw blood from anesthetized rat; Add glucose to increase BGL; Place sample on sensor→Record S-parameters.

Figure 53:
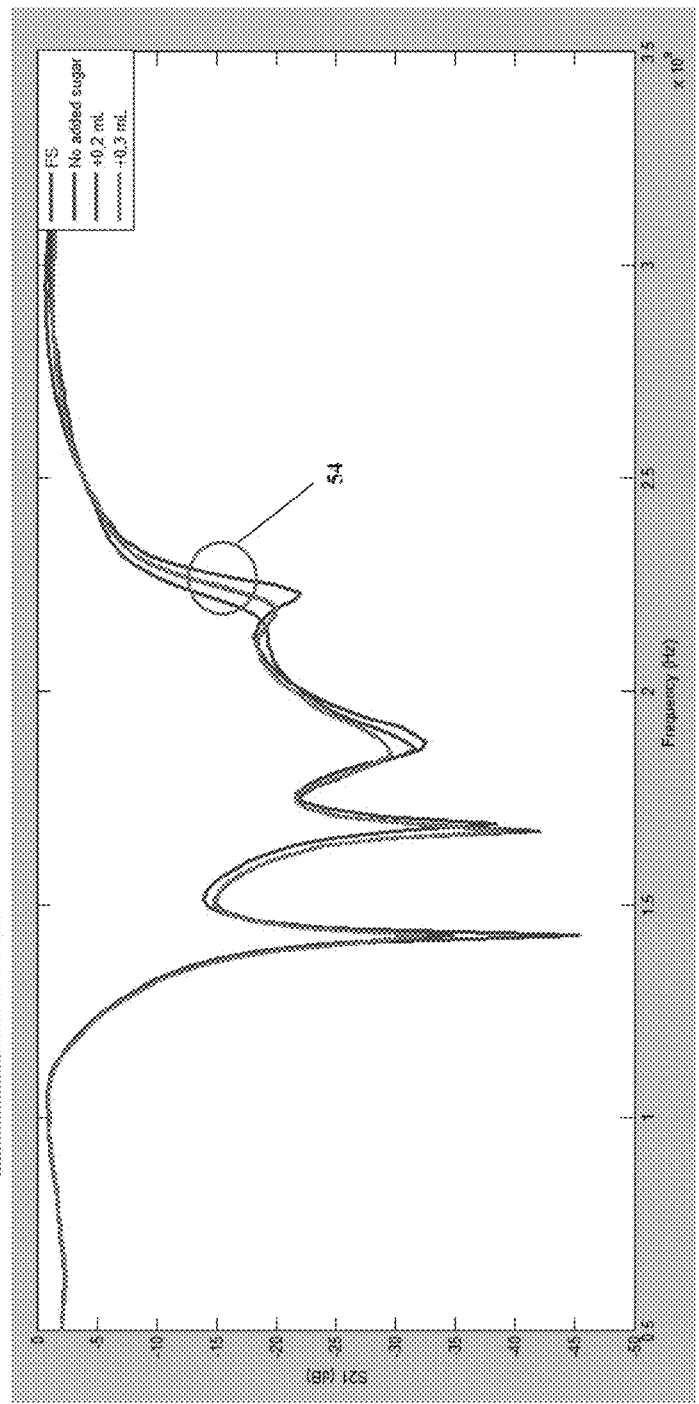
FIG. 53 is a graph showing the Results of measurements on rat blood.
Figure 54:
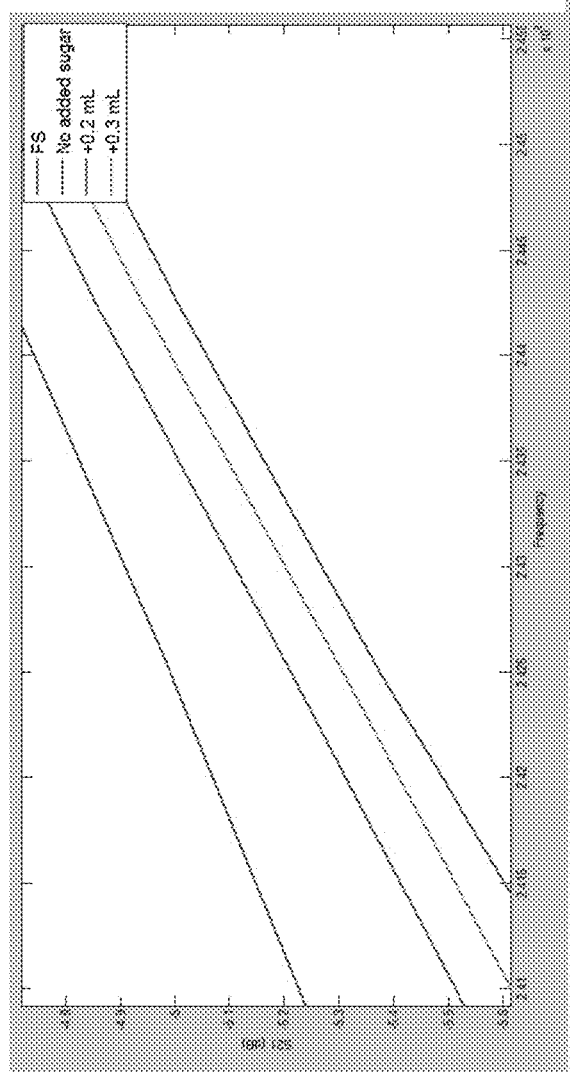
FIG. 54 is a graph showing the zoomed image of circle 54 is shown in FIG. 53.
Figure 55:
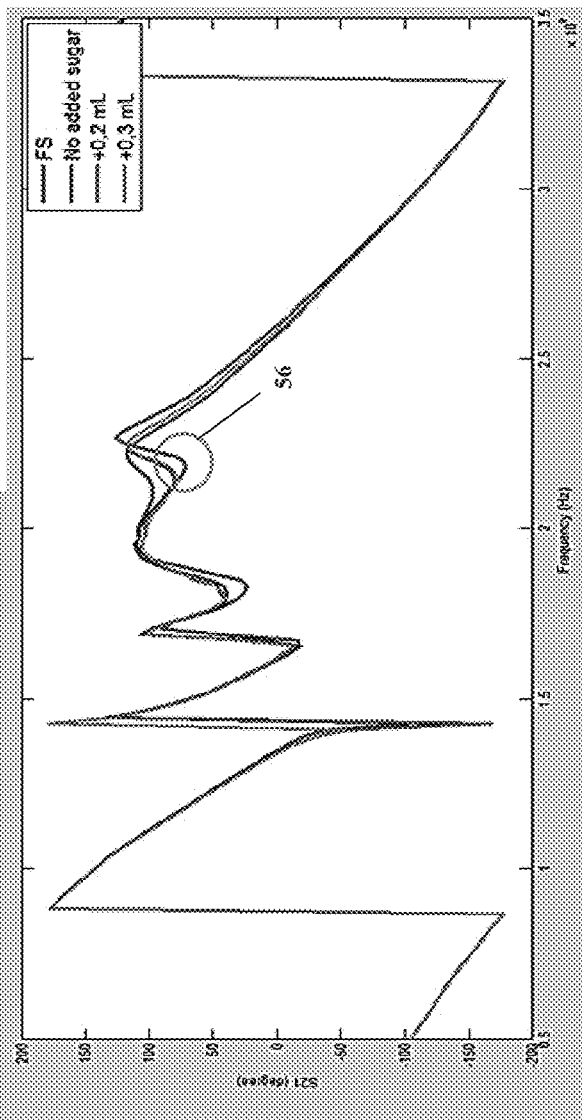
FIG. 55 is a graph showing the Measurements on Blood—$S_{21}$ Phase—Rigid Filter and Results of measurements on rat blood.
Figure 56:
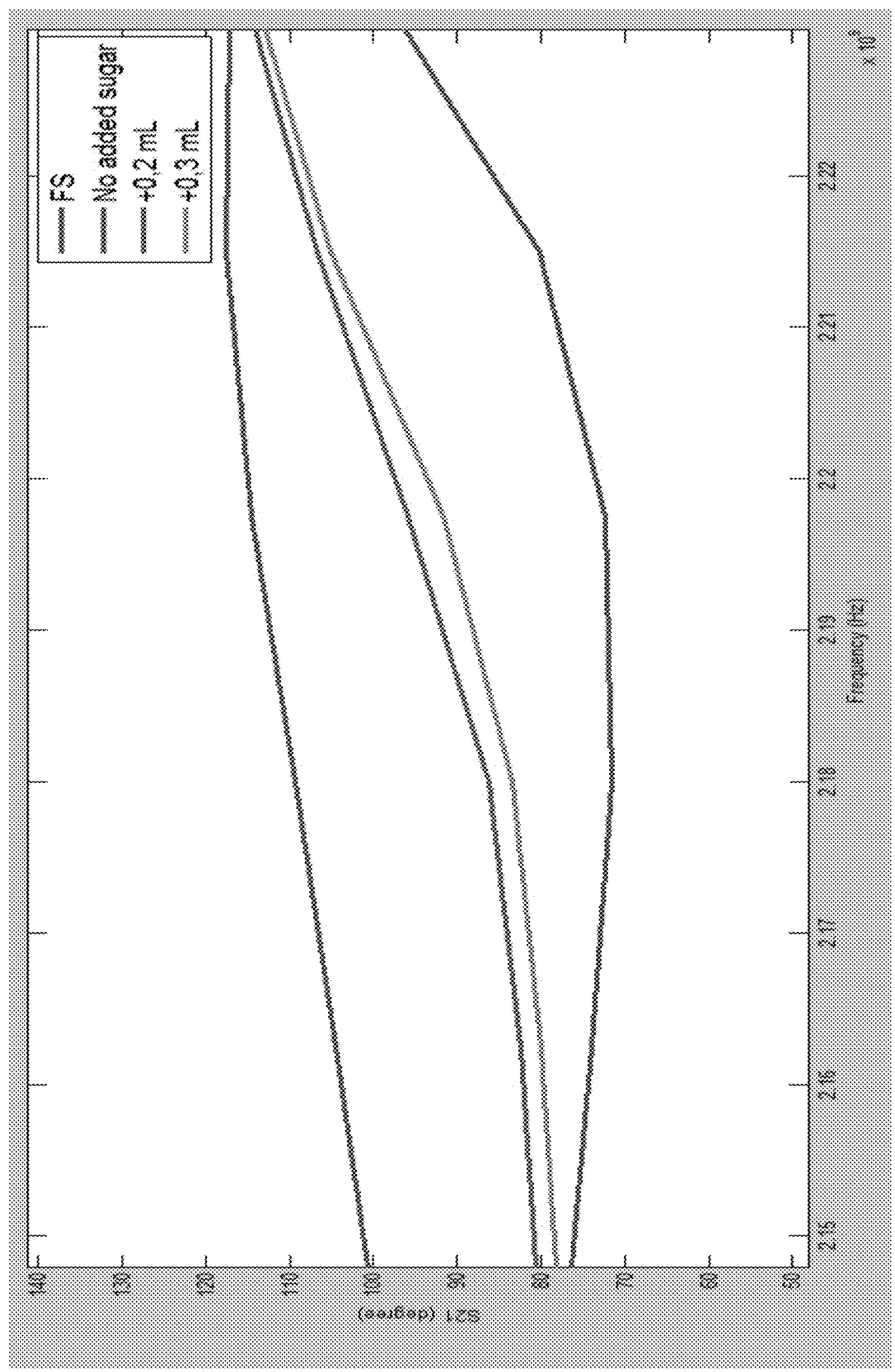
FIG. 56 is a graph showing the zoomed image of circle 56 in FIG. 55.

Results of measurements on rat blood is shown in FIG. 53 and the zoomed image is shown in FIG. 54. Measurements on Blood—$S_{21}$ Phase—Rigid Filter and Results of measurements on rat blood is shown in FIG. 55 and the zoomed image is shown in FIG. 56.

Serum Measurements—Rigid Filter

Experimental Setup and the following setup was conducted: Place 7 mL of serum in container; Vary glucose levels (around 40 observation points); Collect S-parameters; After collecting the data, the whole sets were independently inputted to the build the model. The Clarke error grid (in addition to the percentage error) were considered to compare the results.

Figures 57A, 57B:
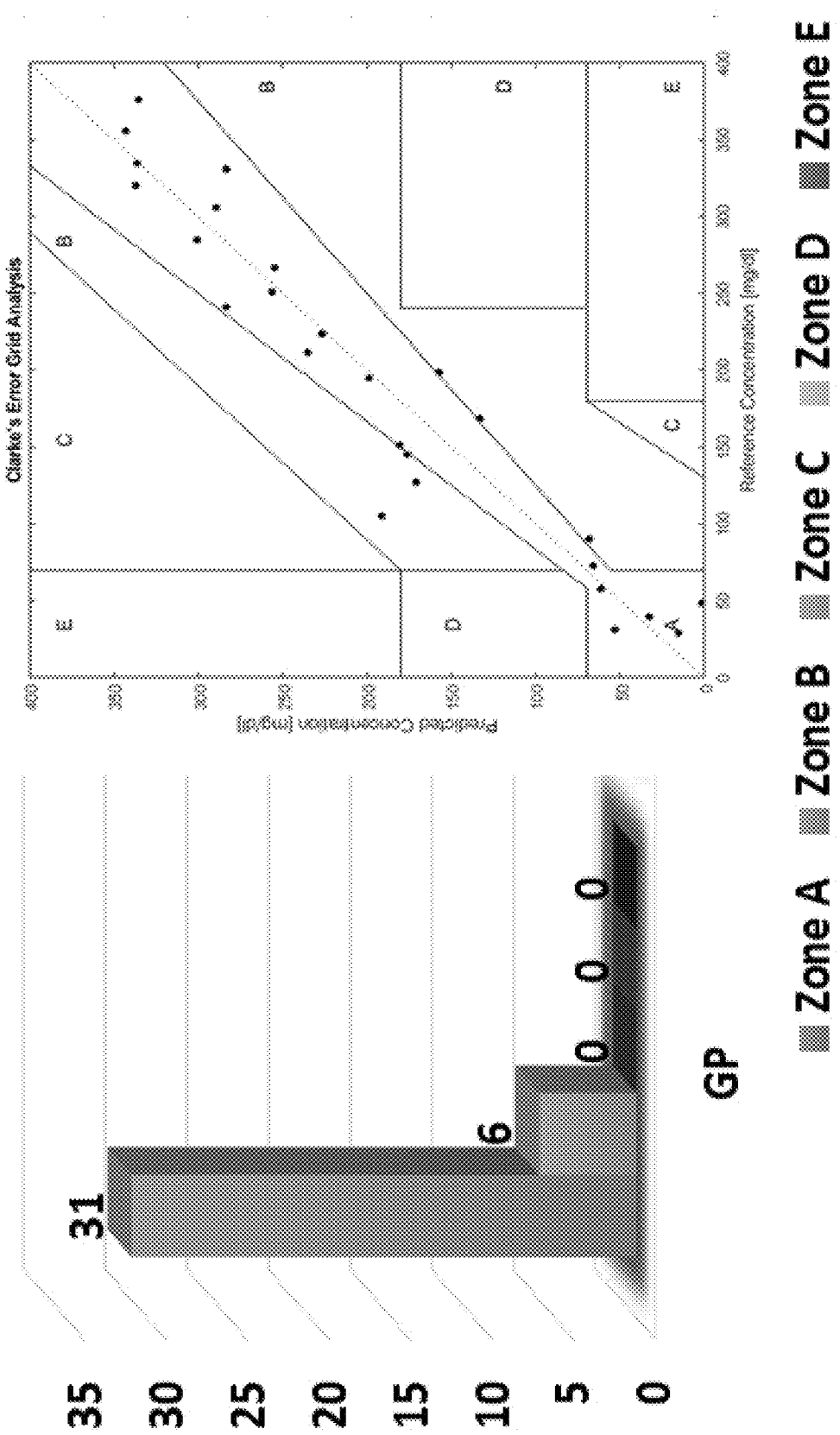
FIGS. 57A-57B are graphs showing the Broadband Rigid and the Clark Error Grid Output.
Figure 58A:
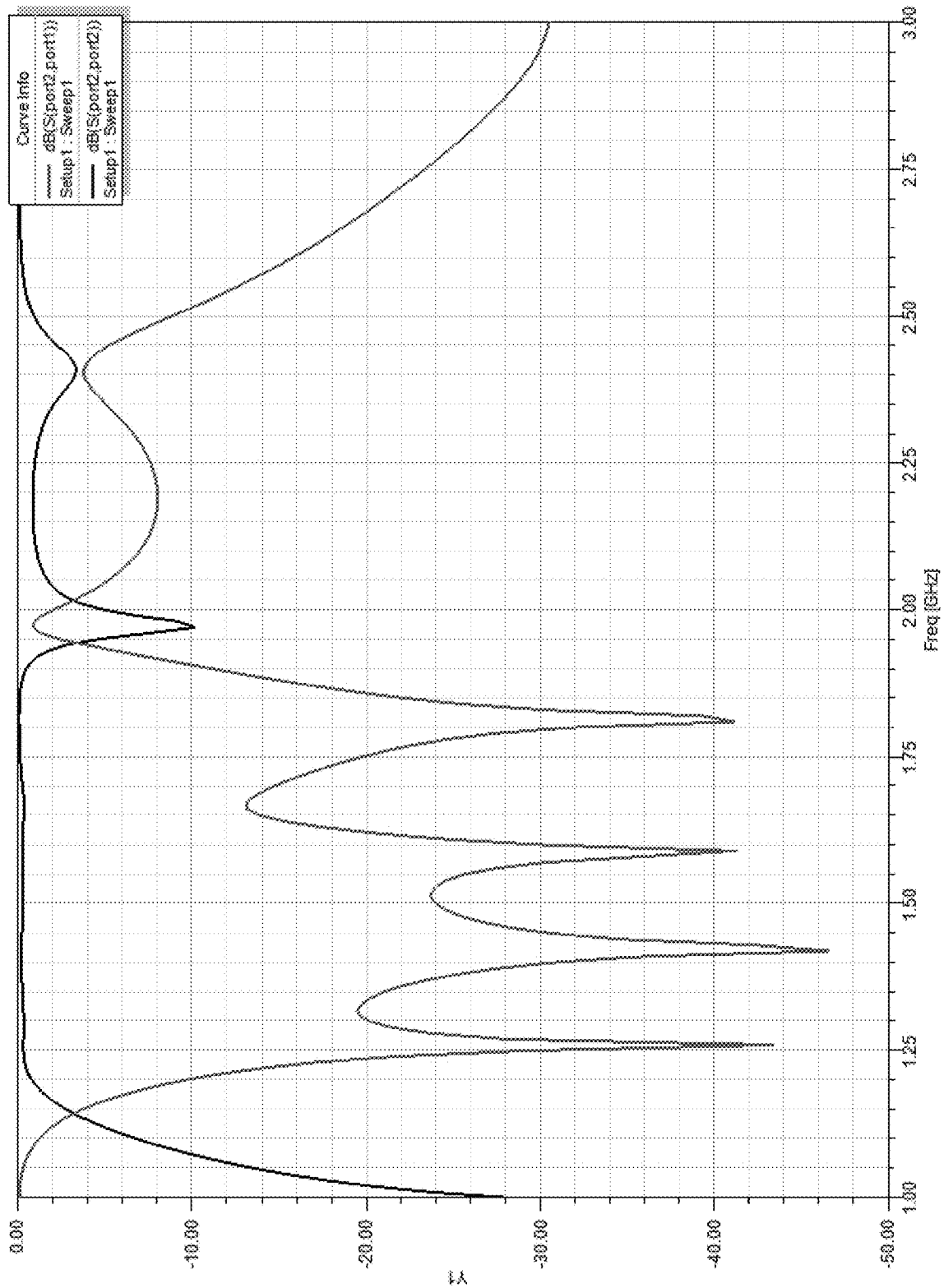
FIGS. 58A-58B are graphs of a switch used to bridge over a gap in the feeding line in order to allow switching between band reject and band pass operation.
Figure 58B:
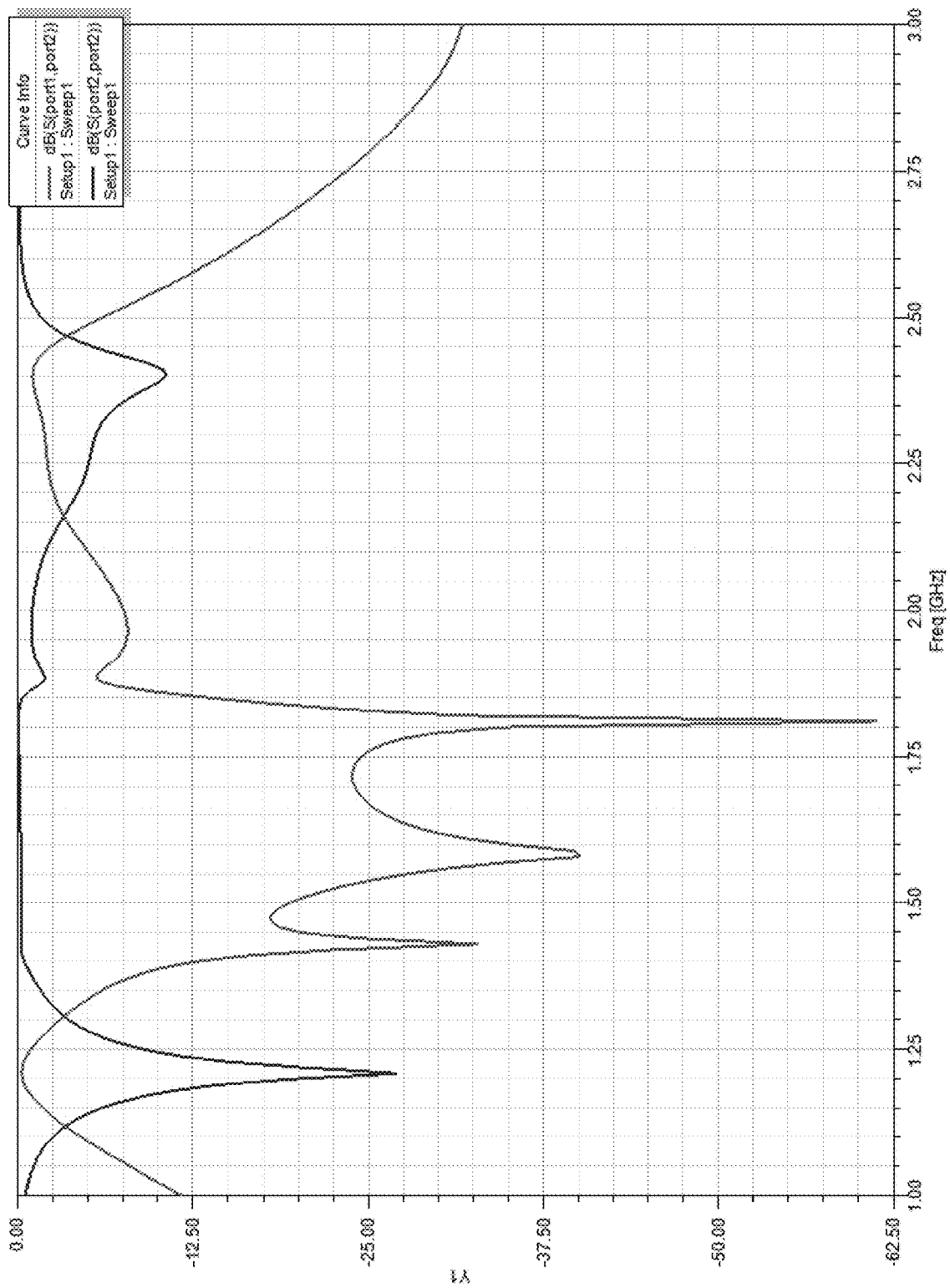
Figure 59A:
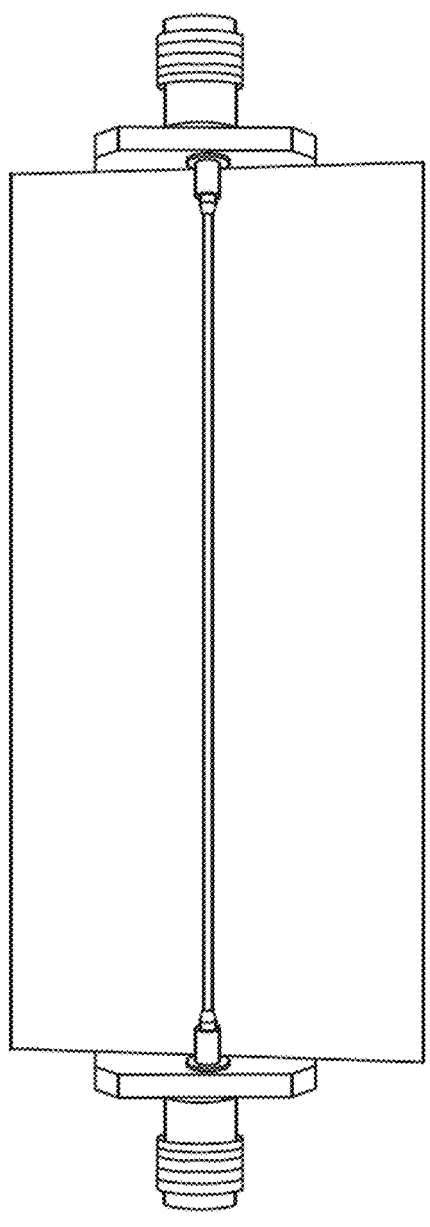
FIGS. 59A-59B are top views of photos of the flexible Filter top layer and bottom layer.
Figure 59B:
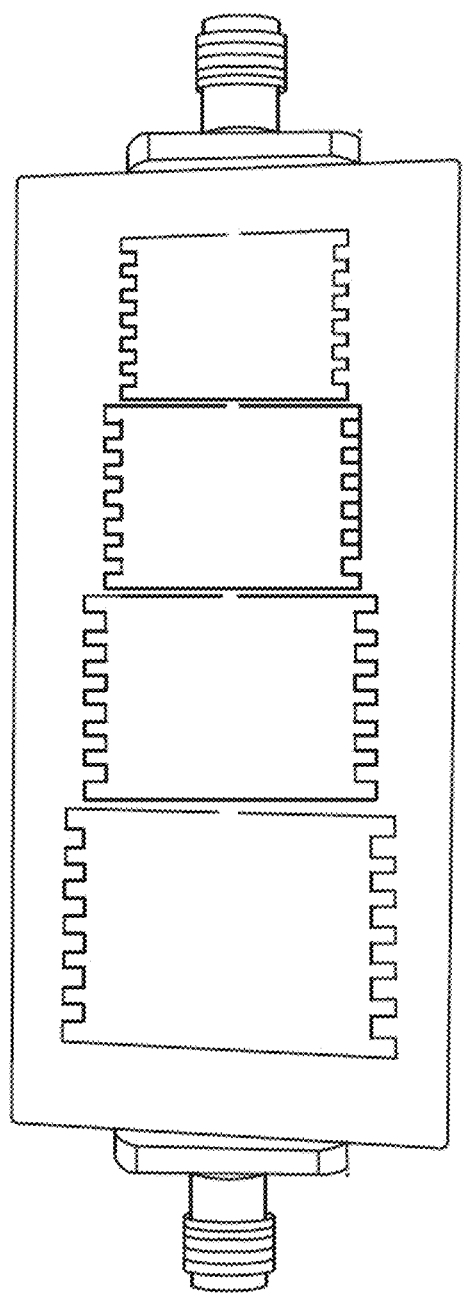
Figure 60:
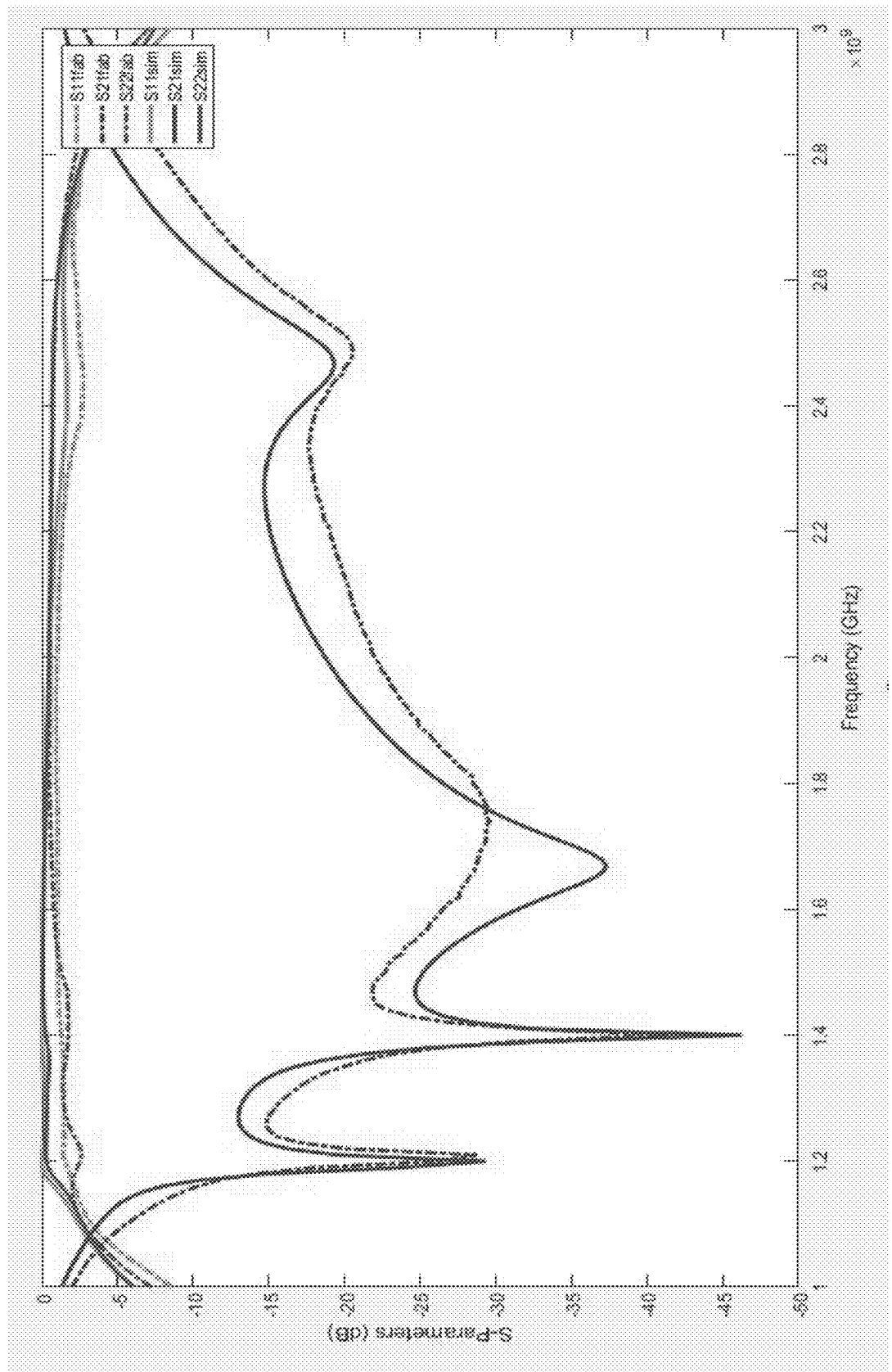
FIG. 60 is a graph showing Free space—Flexible Filter measurement versus simulations.

Broadband Rigid and the Clark Error Grid Output is shown in FIGS. 57A-57B. Relying on Gaussian Processes. Leave one out cross validation. Alternate embodiment—Band Reject to Band Pass switching. A switch can be used to bridge over a gap in the feeding line in order to allow switching between band reject and band pass operation, as shown in FIGS. 58A-58B. Flexible Filter measurements is shown in FIGS. 59A-59B. Free space—Flexible Filter measurement versus simulations is shown in FIG. 60.

Clinical Trials (Control Group)

In one example, a procedure included 6 volunteers are considered for the experiment. The experiment consists of performing the Oral Glucose Tolerance Test twice for each patient). Reference glucose levels are measured using the glucometer each 15 min, and readings from the sensor are performed every 5 min. Measurements taken using log-periodic filter, flexible antenna.

Results

Figure 61:
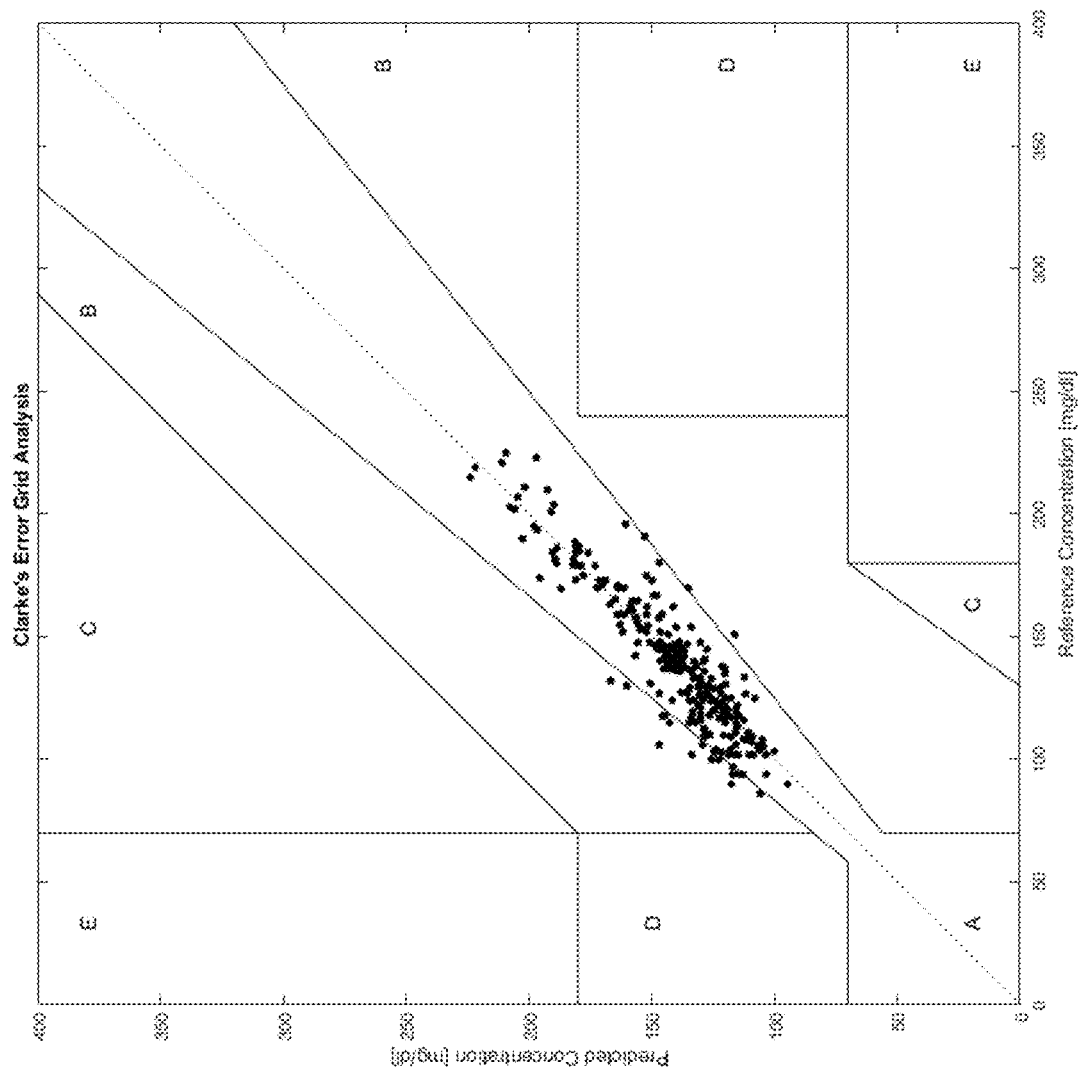
FIG. 61 is a graph of a Clarke error grid that illustrates the reference and predicted glucose levels using Gaussian Process.

A Clarke error grid that illustrates the reference and predicted glucose levels using Gaussian Process is shown in FIG. 61. All the 276 points lay in Zones A & B, with the majority (258 points, 93.5%) being in Zone A.

Sensor Substrate:

In one embodiment, the filter is mounted along with different sensors (humidity, sweat, temperature . . . ) inside an anti-sweat/gear or band typically placed on the fore arm between the elbow and the hand above the main veins. The sensor is designed on a dielectric substrate with a very thin height. The same sensor can be designed on a flexible substrate to take the shape of the patient's arm and properly cover the underlying veins. The flexible design can also be designed using an adhesive—flexible material such as silicon layers, skin-mounted adhesive and then fixed directly on the patient's hand.

Adjustment to Different Patients

The response of the filter is expected to change from one patient to another depending on many criteria including but not limited to: Skin thickness, color, type (hairy and glabrous skin); Skin perfusion, hydration; Sweating; Patient metabolism and body mass index; and other medical conditions such as cholesterol, diabetes.

In one embodiment, it is possible to further adjust the response of the filter, first the highly correlated regions during training to glucose levels are determined using signal processing techniques and then the band reject ranges of the filter can be adjusted to focus on this zone by relying on reconfiguration techniques. The reconfigurable band will improve the sensitivity of the sensor and make it more personalized for each patient.

Possible Alternate Implementations of the Design

This sensor can detect the variation of permittivity hence it can be used in different applications such as: Blood Glucose detection and any other blood Biomarkers, hydration monitoring/blood flow, Cholesterol, Bone fracture healing monitoring, cardiac activity: heart rate, blood pressure, and Material/liquid characterization. A similar design can be used to administer localized radiation-based treatment jointly with/without medication to specific underlying patterns/structures.

Metrics that are Measured:

The sensor is connected to a network analyzer to convert the detected energy into magnitude and phase. For the filter, S11, S21, S22, and S12 parameters are detected including, but not limited to: Magnitude, and Phase or impedance, and to derive the Power level.

Predictive Modeling for Selection of Critical Features:

The sensor is connected to a signal processing system to convert the magnitude and/or the phase into concentration of the blood constituents. The Predictive modeling for selection of critical features comprises 1) Measuring the different S parameters using the sensor; 2) Preprocessing of the data outlier and noise removal using different techniques (wavelet, moving average filters or other types of filters); 3) extracting feature; 4) Modeling, calibrating and tuning; and 5) recalibrating model for enhanced accuracy.

Preprocessing of the data comprises outlier and noise removal using different techniques (wavelet, moving average filters or other types of filters);

Extracting features comprise S parameter Magnitude, phase and/or impedance is sampled into different frequency components. The features are then normalized (between −1 and 1): Remove the reference value (equivalent to the values corresponding to a glucose concentration of 80 mg/dl for example); Remove the mean of each metric; Divide by the maximum of each metric.

Modeling, calibrating and tuning comprises regularized regression in one embodiment is used to predict the glucose concentrations (Lasso, PLS, Hybrid models, Gaussian Processes . . . ). Single feature model and multiple-feature models can be used. Time based models can be used.

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

REFERENCES

[1] L. F. Chen, C. K. Ong, C. P. Neo, V. V. Varadan, and V. K. Varadan, Microwave Electronics: Measurement and Materials Characterization, 1st ed. Chichester, U.K.: Wiley, 2004.

[2] M. S. Boybay and O. M. Ramahi, "Non-destructive thickness Measurement using quasi-static resonators," IEEE Microw. Wireless Compon. Lett., vol. 23, no. 4, pp, 217-219, April 2013.

[3] C. Hsu, K. Chen, C. Lee and C. Yang, "Improved approach using multiple planar complementary split-ring resonators for accurate measurement of permittivity," 2016 IEEE MTT-S International Wireless Symposium (IWS), Shanghai, 2016, pp. 1-4.

[4] D. M. Pozar, Microwave Engineering, 3rd ed. Hoboken, NJ: Wiley, 2005.

[5] C. A. Balanis, Antenna Theory: Analysis and Design. 4th ed. Hoboken, NJ: John Wiley, 2016.

[6] M. S. Boybay and O. M. Ramahi, "Material characterization using complementary split-ring resonators," IEEE Trans. Instrum. Meas., vol. 61, no. 11, pp. 3039-3046, November 2012.

[7] Y. Liu X. Tang Z. X. Zhang X. L. Huang "Novel Nested Split-Ring—Resonator (SRR) for Compact Filter Application", *Progress In Electromagnetics Research (PIER)* vol. 136 2013 pp. 765-773.

[8] Rusni, I. M.; Ismail, A.; Alhawari, A. R. H.; Hamidon, M. N.; Yusof, N. A. An Aligned-Gap and Centered-Gap Rectangular Multiple Split Ring Resonator for Dielectric Sensing Applications. *Sensors* 2014, 14, 13134-13148.

[9]. A. Bahar, Z. Zakaria, E. Ruslan, A. Isa and R. Alahnomi "Analysis of enhanced coupling peripheral type ring resonator sensor for liquid.", *ARPN Journal of Engineering and Applied Sciences*, vol. 11, no. 6, 2016.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A sensor to non-invasively detect a concentration of biomarkers comprising: a miniaturized electromagnetic based passive microwave circuitry to extract an electrical property of a body constituent the miniaturized electromagnetic based passive microwave circuitry targeting at least one of radial, median, cephalic, or ulnar arteries comprising, a sensing device to be placed near the body; an RF energy source; an RF energy converter to convert RF energy into phase and magnitude parameters; a phase and magnitude converter to provide concentration information of the body constituent; wherein the microwave circuitry covers a microwave spectrum and the microwave circuitry reacts to loading by the body constituent; wherein the microwave circuitry is reconfigurable to allow frequency tuning, the microwave circuitry includes a plurality of open loop resonators ranging between 1.5 GHZ and 2.5 GHz to operate as a multiband and reconfigurable filter; the microwave circuitry attains a high sensitivity to lossy material over a 1.25 and 2.25 GHz frequency span; eight stop bands ranging between 1.5 GHz and 2.5 GHz and the eight stop bands are separated by seven pass bands.

2. The sensor as claimed in claim 1, further comprising a flexible substrate and a perturbation of an electric field around the plurality of open loop resonators enhance the electric field locations above the radial artery; the plurality of open loop resonators and perturbations are aligned vertically with a feeding line and the radial artery, and meandered sidelines of the plurality of open loop resonators are optimized to concentrate the perturbated electric field on the median and cephalic arteries.

3. The sensor as claimed in claim 1, further comprising a tapered transmission line implemented to increase a bandwidth of the microwave circuitry wherein the tapered transmission line along with the plurality of open loop resonators in a bottom layer enforces a broadband rejection response of the sensor and increases a rejection bandwidth of the microwave circuit, which allows for a wide range of penetration depth to reach blood vessels, and captures characteristics at multiple frequencies and enhance accuracy.

4. The sensor as claimed in claim 3, wherein the plurality of open loop resonators are operated individually or collectively and the plurality of open loop resonators include a length equivalent to $\lambda/2$ at a resonance frequency.

5. The sensor as claimed in claim 4, wherein the plurality of open loop resonators are disposed in the bottom layer of the miniaturized electromagnetic based passive microwave circuitry and the sensitivity is 0.42 dB/$e_r$ and the sensitivity is 3.65°/$e_G$ at 2.25 GHz.

6. The sensor as claimed in claim 5, wherein the plurality of open loop resonators are disposed in a logarithmic periodic distribution and the microwave circuitry is reconfigurable to allow frequency tuning by reshaping the microwave circuit through different switching connections within its topology and the reconfiguration is based on individual feedback response based on an interaction with underlying tissue to enhance individual specific body sense operation.

7. The sensor as claimed in claim 6, wherein the plurality of open loop resonators comprise a plurality of meandered lines to decrease a size of the open loop resonators, wherein the RF energy includes an E field that is disturbed for enhanced sensitivity capabilities.

8. The sensor as claimed in claim 7, wherein the tapered transmission line is separated from a sensing surface by a dielectric material; wherein the sensor is connected to a wearable Vector Network Analyzer, a reflectometer, a transceiver, or any other two-port measuring device to detect the RF energy and convert the RF energy into S-parameters.

9. The sensor as claimed in claim 8, further comprising a signal processing system to convert the S-parameters into concentrations of the body constituent.

10. The sensor as claimed in claim 9, wherein the microwave circuitry includes an operating band that is reconfigurable.

11. The sensor as claimed in claim 10, wherein the sensor is a combination between a plurality of reconfigurable filters that can operate individually or as group in different combination of band pass and band stop filter behaviors.

12. The sensor in claim 1, further comprising an octa-band electromagnetic two port network composed of the plurality of open loop resonators comprising at least eight open loop resonators, wherein four resonators form a first set and another four resonators form a second set, wherein the first set and the second set include a generally hexagonal configuration following a distribution of arteries and veins.

13. The sensor as claimed in claim 12, wherein the plurality of open loop resonators include a length equivalent to $\lambda/2$ at a resonance frequency and the open loop resonators include eight stop bands ranging between about 1.5 GHz and about 2.5 GHz.

14. The sensor as claimed in claim 13, further comprising a top layer including of a feeding network, and a bottom layer including the plurality of open loop resonators; wherein the top layer and the bottom layer are conductive layers are separated by a dielectric material.

15. The sensor as claimed in claim 14, wherein the top layer comprises a conductive trace connecting a first port and a second port; and the conductive trace is a feeding line.

16. The sensor as claimed in claim 15, wherein the feeding line is tapered or a general rectangular network with an inner rectangular gap.

17. The sensor as claimed in claim 16, wherein the at least eight open loop resonators have different lengths, and operate at different frequencies for a multi-band response.

18. The sensor as claimed in claim 17, wherein the bottom layer is a sensing area near a material of interest or blood stream to cause a specific shift in frequency and quality factor, where the specific shift the frequency and quality factor enables the at least eight open loop resonators to monitor and detect a variation of the concentration of the blood constituent.

19. The sensor as claimed in claim 18, further comprising a reconfigurable frequency, which allows the sensor to continuously cover all the frequencies between about 1.5 GHz and about 2.5 GHz.

20. The sensor as claimed in claim 19, wherein the reconfigurable frequency is controlled by a plurality of varactors or a plurality of digitally tunable capacitors with a maximum applied voltage of about 5 volts.

* * * * *